US012779051B2

(12) United States Patent
Sweeney

(10) Patent No.: US 12,779,051 B2
(45) Date of Patent: Nov. 3, 2026

(54) AAV CARDIAC GENE THERAPY FOR CARDIOMYOPATHY IN HUMANS

(71) Applicant: University of Florida Research Foundation, Incorporated, Gainesville, FL (US)

(72) Inventor: Hugh Lee Sweeney, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1269 days.

(21) Appl. No.: 17/628,139

(22) PCT Filed: Jul. 17, 2020

(86) PCT No.: PCT/US2020/042663

§ 371 (c)(1),
(2) Date: Jan. 18, 2022

(87) PCT Pub. No.: WO2021/016126

PCT Pub. Date: Jan. 28, 2021

(65) Prior Publication Data

US 2022/0265858 A1 Aug. 25, 2022

Related U.S. Application Data

(60) Provisional application No. 62/876,540, filed on Jul. 19, 2019.

(51) Int. Cl.

| | |
|---|---|
| ***A61K 48/00*** | (2006.01) |
| ***A61K 38/17*** | (2006.01) |
| ***C07K 14/47*** | (2006.01) |
| ***C12N 9/64*** | (2006.01) |
| ***C12N 15/86*** | (2006.01) |

(52) U.S. Cl.

CPC ...... *A61K 48/0058* (2013.01); *A61K 38/1709* (2013.01); *C07K 14/4728* (2013.01); *C12N 9/6472* (2013.01); *C12N 15/86* (2013.01); *C12Y 304/22061* (2013.01); *C12N 2750/14143* (2013.01); *C12N 2840/203* (2013.01)

(58) Field of Classification Search

CPC ............ A61K 48/0058; A61K 38/1709; C07K 14/4728; C12N 9/6472; C12N 15/86

See application file for complete search history.

(56) References Cited

U.S. PATENT DOCUMENTS

| | | | | |
|---|---|---|---|---|
| 5,139,941 | A | 8/1992 | Muzyczka et al. | |
| 5,856,152 | A | 1/1999 | Wilson et al. | |
| 5,962,313 | A | 10/1999 | Podsakoff et al. | |
| 6,451,594 | B1 | 9/2002 | Chien et al. | |
| 7,588,756 | B1 * | 9/2009 | Katus | C07K 14/4728 424/93.2 |
| 8,153,376 | B2 | 4/2012 | Pinto et al. | |
| 8,383,601 | B2 * | 2/2013 | Koch | C07K 14/4728 435/325 |
| 9,220,755 | B2 | 12/2015 | Chackraborty et al. | |
| 2002/0164303 | A1 | 11/2002 | Finiels et al. | |
| 2003/0108524 | A1 | 6/2003 | Diagana et al. | |
| 2005/0014262 | A1 | 1/2005 | Gao et al. | |
| 2007/0015238 | A1 | 1/2007 | Snyder et al. | |
| 2007/0098690 | A1 | 5/2007 | Ostedgaard et al. | |
| 2009/0208563 | A1 | 8/2009 | Watkins et al. | |
| 2010/0190840 | A1 | 7/2010 | Koch et al. | |
| 2012/0322861 | A1 | 12/2012 | Byrne et al. | |
| 2013/0012455 | A1 * | 1/2013 | Donath | A61P 1/16 435/375 |
| 2014/0271550 | A1 | 9/2014 | Rabinowitz et al. | |
| 2015/0017205 | A1 | 1/2015 | Kawaoka et al. | |
| 2015/0111955 | A1 | 4/2015 | High et al. | |
| 2015/0374803 | A1 | 12/2015 | Wolfe | |
| 2016/0228504 | A1 | 8/2016 | Katus et al. | |
| 2016/0331846 | A1 | 11/2016 | Keimel et al. | |
| 2017/0348387 | A1 | 12/2017 | Aguirre et al. | |
| 2017/0360960 | A1 | 12/2017 | Gray et al. | |
| 2021/0260215 | A1 | 8/2021 | Sweeney et al. | |
| 2024/0139343 | A1 | 5/2024 | Sweeney et al. | |

FOREIGN PATENT DOCUMENTS

| | | | | |
|---|---|---|---|---|
| CN | 105164264 A | 12/2015 | | |
| EP | 1308517 A1 | 5/2003 | | |
| EP | 3221453 A1 | 5/2016 | | |
| JP | 2016-521708 A | 7/2016 | | |
| JP | 2016-534029 A | 11/2016 | | |
| WO | WO 2002/02148 A2 | 1/2002 | | |
| WO | WO-0202148 A2 * | 1/2002 | A61K 33/26 | |
| WO | WO 2014/093622 A2 | 6/2014 | | |
| WO | WO 2014/197624 A1 | 12/2014 | | |
| WO | WO 2017/127565 A1 | 7/2017 | | |
| WO | WO-2017191274 A2 * | 11/2017 | A61K 48/005 | |
| WO | WO 2019/073058 A1 | 4/2019 | | |
| WO | WO 2019/237067 A1 | 12/2019 | | |
| WO | WO 2020/176896 A1 | 9/2020 | | |
| WO | WO 2021/016126 A1 | 1/2021 | | |

OTHER PUBLICATIONS

Chatterjee et al. (J Thorac Cardiovasc Surg. Jun. 2003;125(6):1461-9. doi: 10.1016/s0022-5223(02)73229-7.) (Year: 2003).*

Sweeny et al. (J Vet Cardiol. Jun. 2011;13(2):131-40. doi: 10.1016/j.jvc.2011.04.001. Epub Jun. 2011) (Year: 2011).*

(Continued)

*Primary Examiner* — Fereydoun G Sajjadi
*Assistant Examiner* — Joel D Levin
(74) *Attorney, Agent, or Firm* — Wolf, Greenfield & Sacks, P.C.

(57) ABSTRACT

The present disclosure provides compositions and methods useful in treating heart conditions. The disclosed compositions and methods encompass gene therapies including a recombinant AAV vector for delivering two or more transgenes into the heart of a human subject. The two or more transgenes comprise an S100A1 protein and a cardiac Apoptosis Repressor with Caspase Recruitment Domain (cARC) apoptotic inhibitor. The disclosure also provides vectors comprising S100A1 and/or cARC cDNA sequences that are codon-optimized for expression in humans.

11 Claims, 23 Drawing Sheets

Specification includes a Sequence Listing.

(56) References Cited

OTHER PUBLICATIONS

Sleeper et al. (Vet Clin North Am Small Anim Pract. Sep. 2017;47(5):1113-1121. doi: 10.1016/j.cvsm.2017.04.005. Epub Jun. 21, 2017., see IDS) (Year: 2017).*
Extended European Search Report in connection with Application No. EP20844818.3 mailed Jul. 17, 2023.
International Search Report and Written Opinion for Application No. PCT/US2021/064637, mailed May 11, 2022.
International Preliminary Report on Patentability for Application No. PCT/US2021/064637, mailed Jul. 6, 2023.
[No Author Listed] Akc Canine Health Foundation, Therapeutic gene transfer abrogates canine dilated cardiomyopathy, [online], Internet, Wayback Machine, Apr. 4, 2019: https://web.archive.org/web/20190404023143/https://www.akcchf.org/research/participate-in-research/Therapeutic-gene-transfer-abrogates-canine-dilated-cardiomyopathy.html, [Date of Search: Jun. 20, 2024].
Ai et al., Adeno-associated virus serotype rh. 10 displays strong muscle tropism following intraperitoneal delivery. Sci Rep. Jan. 9, 2017;7:40336. doi: 10.1038/srep40336.
Asokan et al., The AAV vector toolkit: poised at the clinical crossroads. Mol Ther. Apr. 2012;20(4):699-708. doi: 10.1038/mt.2011.287. Epub Jan. 24, 2012.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Bish et al., Cardiac gene transfer of short hairpin RNA directed against phospholamban effectively knocks down gene expression but causes cellular toxicity in canines. Hum Gene Ther. Aug. 2011;22(8):969-77. doi: 10.1089/hum.2011.035. Epub Jun. 8, 2011.
Bish et al., Percutaneous transendocardial delivery of self-complementary adeno-associated virus 6 achieves global cardiac gene transfer in canines. Mol Ther. Dec. 2008;16(12):1953-9. doi: 10.1038/mt.2008.202. Epub Sep. 23, 2008.
Brutlag et al., Improved sensitivity of biological sequence database searches. Comput Appl Biosci. Jul. 1990;6(3):237-45. doi: 10.1093/bioinformatics/6.3.237.
Donato, Intracellular and extracellular roles of S100 proteins. Microsc Res Tech. Apr. 15, 2003;60(6):540-51. doi: 10.1002/jemt.10296.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Ennis et al. Dual gene therapy with SERCA1 and Kir2.1 abbreviates excitation without suppressing contractility. J Clin Invest. Feb. 2002;109(3):393-400. doi: 10.1172/JCI13359.
Flotte, Gene therapy: the first two decades and the current state-of-the-art. J Cell Physiol. Nov. 2007;213(2):301-5. doi: 10.1002/jcp.21173.
Foti et al., Delivering multiple gene products in the brain from a single adeno-associated virus vector. Gene Ther. Nov. 2009;16(11):1314-9. doi: 10.1038/gt.2009.106. Epub Sep. 3, 2009. Author Manuscript, 13 pages.
GenBank Submission; NCBI Reference Accession No. NM_001048121.1, Oct. 11, 2020, 3 pages.
GenBank Submission; NCBI Reference Accession No. XM_003999773.3, Dec. 12, 2017, 1 page.
GenBank Submission; NCBI Reference Accession No. XM_005622816.2 (replaced by Accession No. NM_001362601.1), Jul. 2, 2020, 3 pages.
GenBank Submission; NCBI Reference Accession No. XM_006941587.2, Dec. 12, 2017, 2 pages.
Gustafsson et al., Apoptosis repressor with caspase recruitment domain protects against cell death by interfering with Bax activation. J Biol Chem. May 14, 2004;279(20):21233-8. doi: 10.1074/jbc.M400695200. Epub Mar. 5, 2004.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Kawamoto et al., Widespread and early myocardial gene expression by adeno-associated virus vector type 6 with a beta-actin hybrid promoter. Mol Ther. Jun. 2005;11(6):980-5. doi: 10.1016/j.ymthe.2005.02.009.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Levitt et al., Definition of an efficient synthetic poly(A) site. Genes Dev. Jul. 1989;3(7):1019-25. doi: 10.1101/gad.3.7.1019.
Li et al., Engineering adeno-associated virus vectors for gene therapy. Nat Rev Genet. Apr. 2020;21(4):255-272. doi: 10.1038/s41576-019-0205-4. Epub Feb. 10, 2020.
Mcclements et al., Adeno-associated Virus (AAV) Dual Vector Strategies for Gene Therapy Encoding Large Transgenes. Yale J Biol Med. Dec. 19, 2017;90(4):611-623.
Mroske et al., A capillary electrophoresis sequencing method for the identification of mutations in the inverted terminal repeats of adeno-associated virus. Hum Gene Ther Methods. Apr. 2012;23(2):128-36. doi: 10.1089/hgtb.2011.231. Epub May 21, 2012.
Muller et al., Augmentation of AAV-mediated cardiac gene transfer after systemic administration in adult rats. Gene Ther. Dec. 2008;15(23):1558-65. doi: 10.1038/gt.2008.111. Epub Jul. 10, 2008.
Muller et al., Improved cardiac gene transfer by transcriptional and transductional targeting of adeno-associated viral vectors. Cardiovasc Res. Apr. 1, 2006;70(1):70-8. doi: 10.1016/j.cardiores.2005.12.017. Epub Jan. 31, 2006.
Muller et al., Targeting the heart with gene therapy-optimized gene delivery methods. Cardiovasc Res. Feb. 1, 2007;73(3):453-62. doi: 10.1016/j.cardiores.2006.09.021. Epub Oct. 3, 2006.
Naso et al., Adeno-Associated Virus (AAV) as a Vector for Gene Therapy. BioDrugs. Aug. 2017;31(4):317-334. doi: 10.1007/s40259-017-0234-5.
Nicklin et al., Efficient and selective AAV2-mediated gene transfer directed to human vascular endothelial cells. Mol Ther. Sep. 2001;4(3):174-81. doi: 10.1006/mthe.2001.0424.
Pacak et al., AAV vectors for cardiac gene transfer: experimental tools and clinical opportunities. Mol Ther. Sep. 2011;19(9):1582-90. doi: 10.1038/mt.2011.124. Epub Jul. 26, 2011.
Pacak et al., Tissue specific promoters improve specificity of AAV9 mediated transgene expression following intra-vascular gene delivery in neonatal mice. Genet Vaccines Ther. Sep. 23, 2008;6:13. doi: 10.1186/1479-0556-6-13.
Raake et al., Cardio-specific long-term gene expression in a porcine model after selective pressure-regulated retroinfusion of adeno-associated viral (AAV) vectors. Gene Ther. Jan. 2008;15(1):12-7. doi: 10.1038/sj.gt.3303035. Epub Oct. 18, 2007.
Shen et al., Inhibition of pathological brain angiogenesis through systemic delivery of AAV vector expressing soluble FLT1. Gene Ther. Nov. 2015;22(11):893-900. doi: 10.1038/gt.2015.57. Epub Jun. 19, 2015. Author Manuscript, 19 pages.
Shen et al., Intravenous delivery of adeno-associated viral vector serotype 9 mediates effective gene expression in ischemic stroke lesion and brain angiogenic foci. Stroke. Jan. 2013;44(1):252-4. doi: 10.1161/STROKEAHA.112.662965. Epub Dec. 18, 2012.
Sleeper, Status of Therapeutic Gene Transfer to Treat Cardiovascular Disease in Dogs and Cats. Vet Clin North Am Small Anim Pract. Sep. 2017;47(5):1113-1121. doi: 10.1016/j.cvsm.2017.04.005. Epub Jun. 21, 2017.
Strausberg, et al., *Homo sapiens* S100 calcium binding protein Al, mRNA (cDNA clone MGC:1324 DE Image:3543900), complete eds., Database EMBL [Online] EBI; Database accession No. BC014392, Sep. 23, 2001. 3 pages.
Su et al., AAV serotype-1 mediates early onset of gene expression in mouse hearts and results in better therapeutic effect. Gene Ther. Nov. 2006;13(21):1495-502. doi: 10.1038/sj.gt.3302787. Epub Jun. 15, 2006.
Tanguy et al., Systemic AAVrh10 provides higher transgene expression than AAV9 in the brain and the spinal cord of neonatal mice. Front Mol Neurosci. Jul. 28, 2015;8:36. doi: 10.3389/fnmol.2015.00036.

(56) References Cited

OTHER PUBLICATIONS

Urabe et al., A novel dicistronic AAV vector using a short IRES segment derived from hepatitis C virus genome. Gene. Oct. 24, 1997;200(1-2):157-62. doi: 10.1016/s0378-1119(97)00412-5.
Van Vliet et al., The role of the adeno-associated virus capsid in gene transfer. Methods Mol Biol. 2008;437:51-91. doi: 10.1007/978-1-59745-210-6_2.
Wang et al., Construction of recombinant adeno-associated virus vector expressing hs100al gene. Chinese Journal of Clinical Pharmacology and Therapeutics. Aug. 26, 2013;18(8):853.
Weitzman et al., Targeted integration by adeno-associated virus. Methods Mol Med. 2003;76:201-19. doi: 10.1385/1-59259-304-6:201.
Wu et al., Effect of genome size on AAV vector packaging. Mol Ther. Jan. 2010;18(1):80-6. doi: 10.1038/mt.2009.255. Epub Nov. 10, 2009.
Yan et al., Trans-splicing vectors expand the utility of adeno-associated virus for gene therapy. Proc Natl Acad Sci U S A. Jun. 6, 2000;97(12):6716-21. doi: 10.1073/pnas.97.12.6716.
Zacchigna et al., Adeno-associated virus vectors as therapeutic and investigational tools in the cardiovascular system. Circ Res. May 23, 2014;114(11):1827-46. doi: 10.1161/CIRCRESAHA.114.302331.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.
Extended European Search Report in connection with Application No. EP19815084.9 mailed Feb. 9, 2022.
International Search Report and Written Opinion in connection with Application No. PCT/US2019/36157 mailed Aug. 28, 2019.
International Preliminary Report on Patentability in connection with Application No. PCT/US2019/36157 mailed Dec. 17, 2020.
International Search Report and Written Opinion in connection with Application No. PCT/US2020/042663 mailed Oct. 28, 2020.
International Preliminary Report on Patentability in connection with Application No. PCT/US2020/042663 mailed Feb. 3, 2022.
Chamberlain et al., A Calsequestrin Cis-Regulatory Motif Coupled to a Cardiac Troponin T Promoter Improves Cardiac Adeno-Associated Virus Serotype 9 Transduction Specificity. Hum Gene Ther. Aug. 2018;29(8):927-937. doi: 10.1089/hum.2017.188. Epub May 9, 2018.
Chatterjee et al., Blocking the development of postischemic cardiomyopathy with viral gene transfer of the apoptosis repressor with caspase recruitment domain. J Thorac Cardiovasc Surg. Jun. 2003;125(6):1461-9. doi: 10.1016/s0022-5223(02)73229-7.
Donath et al., Apoptosis repressor with caspase recruitment domain is required for cardioprotection in response to biomechanical and ischemic stress. Circulation. Mar. 7, 2006;113(9):1203-12. doi: 10.1161/CIRCULATIONAHA.105.576785. Epub Feb. 27, 2006.
Pleger et al., Cardiac AAV9-S100A1 gene therapy rescues post-ischemic heart failure in a preclinical large animal model. Sci Transl Med. Jul. 20, 2011;3(92):92ra64. doi: 10.1126/scitranslmed.3002097. Author Manuscript, 20 pages.
Ruan et al., A hypoxia-regulated adeno-associated virus vector for cancer-specific gene therapy. Neoplasia. May-Jun. 2001;3(3):255-63. doi: 10.1038/sj.neo.7900157.
Xia et al., S100 Proteins as an Important Regulator of Macrophage Inflammation. Front Immunol. Jan. 5, 2018;8:1908. doi: 10.3389/fimmu.2017.01908.
GenBank Submission; NCBI Reference Accession No. AK126904.1, Jan. 9, 2008, 2 pages.
GenBank Submission; NCBI Reference Accession No. AK312152.1, May 24, 2008, 2 pages.
Inouye et al., Codon optimization of genes for efficient protein expression in mammalian cells by selection of only preferred human codons. Protein Expr Purif. May 2015;109:47-54. doi: 10.1016/j.pep.2015.02.002. Epub Feb. 7, 2015.
Jazwa et al., Arteriogenic therapy based on simultaneous delivery of VEGF-A and FGF4 genes improves the recovery from acute limb ischemia. Vasc Cell. Jul. 1, 2013;5:13. doi: 10.1186/2045-824X-5-13.
Mauro et al., A critical analysis of codon optimization in human therapeutics. Trends Mol Med. Nov. 2014;20(11):604-13. doi: 10.1016/j.molmed.2014.09.003. Epub Sep. 25, 2014.
Prasad et al., A single direct injection into the left ventricular wall of an adeno-associated virus 9 (AAV9) vector expressing extracellular superoxide dismutase from the cardiac troponin-T promoter protects mice against myocardial infarction. J Gene Med. Jun. 2011;13(6):333-41. doi: 10.1002/jgm.1576.
Renaud-Gabardos et al., Internal ribosome entry site-based vectors for combined gene therapy. World J Exp Med. Feb. 20, 2015;5(1):11-20. doi: 10.5493/wjem.v5.i1.11.

* cited by examiner

Calvin WnM3

Diastole

Time 1

Calvin WnM3
Systole
Time 1
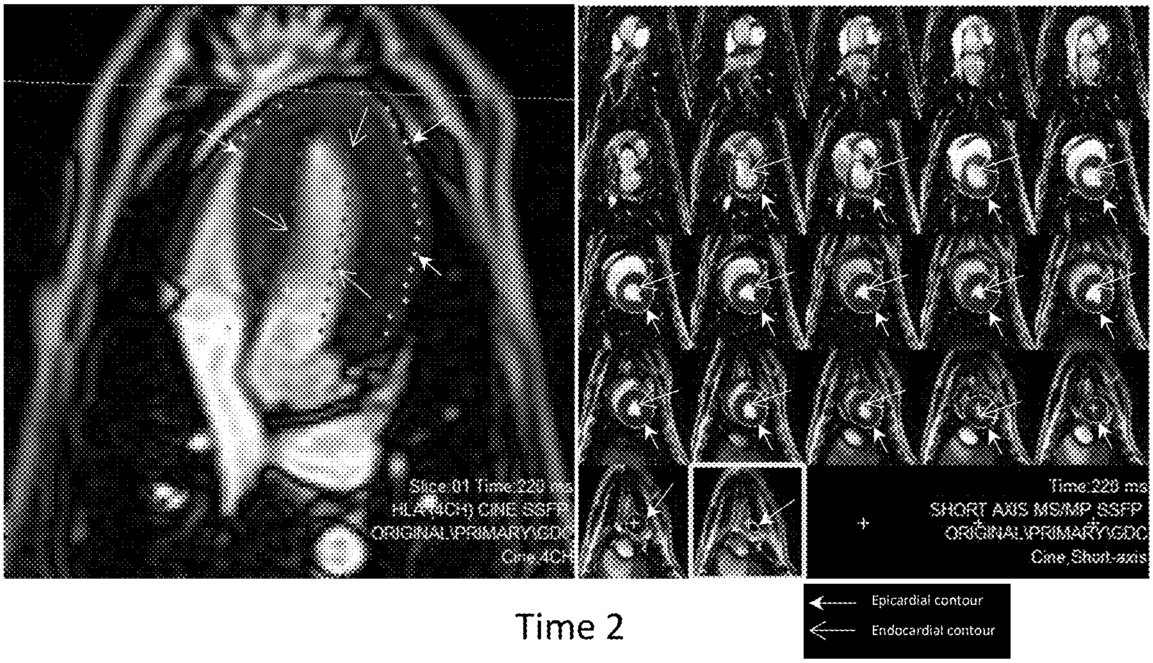
Time 2
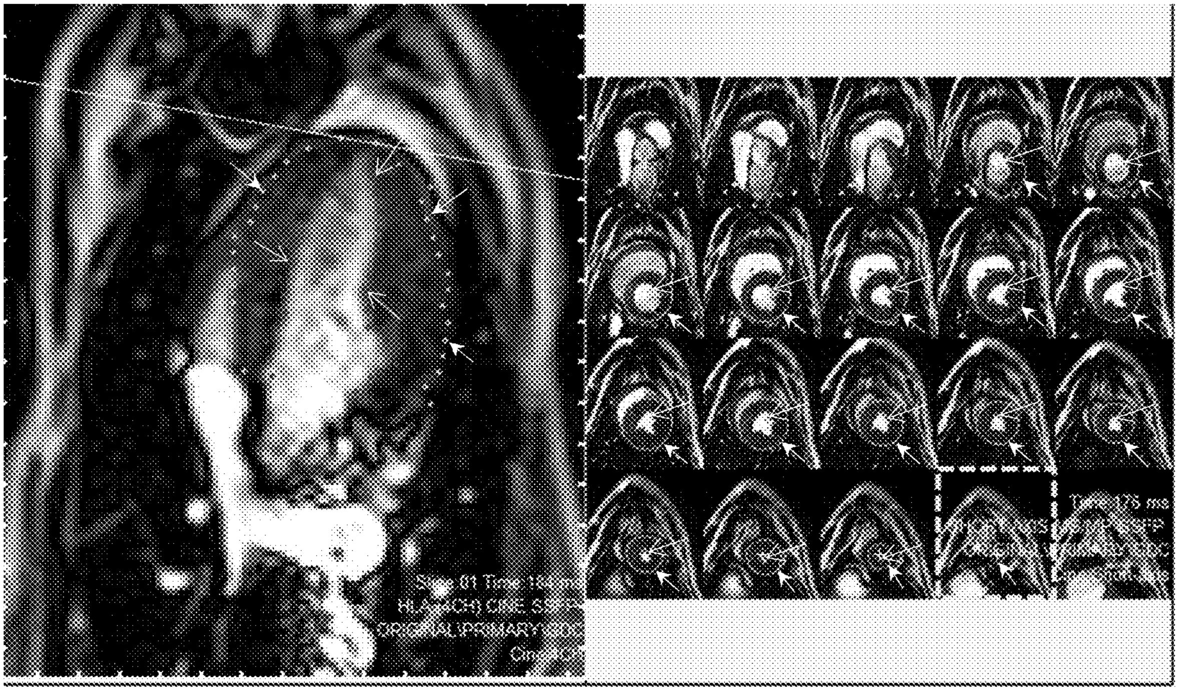
FIG. 3

ATGGGCXXXGAGCTGGAGACXGCXATGGAGACCCTXATCA
10 20 30 40
Native hS100A1 DNA ATGGGCTCTGAGCTGGAGACGGCGATGGAGACCCTCATCA 40
Optimized hS100A1 D ATGGGCAGCGAGCTGGAGACCGCCATGGAGACCCTGATCA 40

ACGTGTTCCACGCCCACXXXGGCAAXGAGGGXGACAAGTA
50 60 70 80
Native hS100A1 DNA ACGTGTTCCACGCCCACTCGGGCAAAGAGGGGGACAAGTA 80
Optimized hS100A1 D ACGTGTTCCACGCCCACAGCGGCAAGGAGGGCGACAAGTA 80

CAAGCTGAGCAAGAAGGAGCTGAAXGAGCTGCTGCAGACX
90 100 110 120
Native hS100A1 DNA CAAGCTGAGCAAGAAGGAGCTGAAAGAGCTGCTGCAGACG 120
Optimized hS100A1 D CAAGCTGAGCAAGAAGGAGCTGAAGGAGCTGCTGCAGACC 120

GAGCTXXXXGGCTTCCTGGAXGCCCAGAAGGAXGTGGAXG
130 140 150 160
Native hS100A1 DNA GAGCTCTCTGGCTTCCTGGATGCCCAGAAGGATGTGGATG 160
Optimized hS100A1 D GAGCTGAGCGGCTTCCTGGACGCCCAGAAGGACGTGGACG 160

CXGTGGACAAGGTGATGAAGGAGCTXGACGAGAAXGGXGA
170 180 190 200
Native hS100A1 DNA CTGTGGACAAGGTGATGAAGGAGCTAGACGAGAATGGAGA 200
Optimized hS100A1 D CCGTGGACAAGGTGATGAAGGAGCTGGACGAGAACGGCGA 200

CGGXGAGGTGGACTTCCAGGAGTAXGTGGTGCTXGTGGCX
210 220 230 240
Native hS100A1 DNA CGGGGAGGTGGACTTCCAGGAGTATGTGGTGCTTGTGGCT 240
Optimized hS100A1 D CGGCGAGGTGGACTTCCAGGAGTACGTGGTGCTGGTGGCC 240

GCXCTXACXGTGGCCTGXAACAAXTTCTTCTGGGAGAACA
250 260 270 280
Native hS100A1 DNA GCTCTCACAGTGGCCTGTAACAATTTCTTCTGGGAGAACA 280
Optimized hS100A1 D GCCCTGACCGTGGCCTGCAACAACTTCTTCTGGGAGAACA 280

GXTGA
Native hS100A1 DNA GTTGA 285
Optimized hS100A1 D GCTGA 285

FIG. 13

```
                         ATGGGCAGCGAGCTGGAGACCGCCATGGAGACCCTGATCA
                                  10        20        30        40
Optimized hS100A1 D      ATGGGCAGCGAGCTGGAGACCGCCATGGAGACCCTGATCA  40
Optimized cS100A1 D      ATGGGCAGCGAGCTGGAGACCGCCATGGAGACCCTGATCA  40

                         ACGTGTTCCACGCCCACAGCGGCAAGGAGGGCXACAAGTA
                                  50        60        70        80
Optimized hS100A1 D      ACGTGTTCCACGCCCACAGCGGCAAGGAGGGCGACAAGTA  80
Optimized cS100A1 D      ACGTGTTCCACGCCCACAGCGGCAAGGAGGGCAACAAGTA  80

                         CAAGCTGAGCAAGAAGGAGCTGAAGGAGCTGCTGCAGACC
                                  90       100       110       120
Optimized hS100A1 D      CAAGCTGAGCAAGAAGGAGCTGAAGGAGCTGCTGCAGACC  120
Optimized cS100A1 D      CAAGCTGAGCAAGAAGGAGCTGAAGGAGCTGCTGCAGACC  120

                         GAGCTGAGCGGCTTCCTGGACGCCCAGAAGGACGXXGACG
                                 130       140       150       160
Optimized hS100A1 D      GAGCTGAGCGGCTTCCTGGACGCCCAGAAGGACGTGGACG  160
Optimized cS100A1 D      GAGCTGAGCGGCTTCCTGGACGCCCAGAAGGACGCCGACG  160

                         CCGTGGACAAGGTGATGAAGGAGCTGGACGAGAACGGCGA
                                 170       180       190       200
Optimized hS100A1 D      CCGTGGACAAGGTGATGAAGGAGCTGGACGAGAACGGCGA  200
Optimized cS100A1 D      CCGTGGACAAGGTGATGAAGGAGCTGGACGAGAACGGCGA  200

                         CGGCGAGGTGGACTTCCAGGAGTACGTGGTGCTGGTGGCC
                                 210       220       230       240
Optimized hS100A1 D      CGGCGAGGTGGACTTCCAGGAGTACGTGGTGCTGGTGGCC  240
Optimized cS100A1 D      CGGCGAGGTGGACTTCCAGGAGTACGTGGTGCTGGTGGCC  240

                         GCCCTGACCGTGGCCTGCAACAACTTCTTCTGGGAGAACA
                                 250       260       270       280
Optimized hS100A1 D      GCCCTGACCGTGGCCTGCAACAACTTCTTCTGGGAGAACA  280
Optimized cS100A1 D      GCCCTGACCGTGGCCTGCAACAACTTCTTCTGGGAGAACA  280

                         GCTGA

Optimized hS100A1 D      GCTGA                                     285
Optimized cS100A1 D      GCTGA                                     285
```

FIG. 14

SEQUENCE LISTING

<160> NUMBER OF SEQ ID NOS: 21

<210> SEQ ID NO 1
<211> LENGTH: 285
<212> TYPE: DNA
<213> ORGANISM: Canis lupus

<400> SEQUENCE: 1

```
atgggctctg agctggagac agcgatggag actctcatca atgtgttcca tgcccactcg     60

ggcaaggagg gaaacaagta caagctgagc aagaaggagc taaaggagct gctgcagact    120

gagctctccg gcttcctgga cgcccagaag gatgcggatg ctgtggacaa ggtgatgaaa    180

gagctagatg agaatggaga tggggaggtg gacttccagg agtatgtggt gctggtggct    240

gccctcacag tggcctgtaa caacttcttc tgggaaaaca gttga                    285
```

<210> SEQ ID NO 2
<211> LENGTH: 285
<212> TYPE: DNA
<213> ORGANISM: Felis catus

<400> SEQUENCE: 2

```
atgggctcag agctggagac ggcgatggag actctcatca acgtgttcca cgcccactcg     60

ggcaaggagg gagacaagta caagctgagc aagaaggagc taaaagagct gctgcagacc    120

gagctctctg gcttcctgga cgcccagaag gatgccgacg ctgtggacaa ggtgatgaaa    180

gagctagacg agaatggaga tggggaggtg gacttccaag agtatgtggt gctggtggct    240

gccctcacag tggcctgtaa caactttttc tgggagaaca gttga                    285
```

<210> SEQ ID NO 3
<211> LENGTH: 1479
<212> TYPE: DNA
<213> ORGANISM: Canis lupus

<400> SEQUENCE: 3

```
atgcaggaag cgccagccgc gctgcccacg gagccgggcc ccagccccgt gcctgccttc     60
```

```
ctcggcaagc tgtgggcgct ggtgggcgac ccggggaccg accacctcat ccgctggagc    120
ccgagcggga ccagtttcct cgtcagcgac cagagccgct tcgccaagga agtgctgccc    180
cagtacttca agcacagcaa catggcgagc ttcgtgcggc agctcaacat gtacggtttt    240
cggaaggtgg tgagcatcga gcagggcggc ctgctcaggc cggagcgcga ccacgtcgag    300
ttccagcacc cgagcttcgt ccgcggccga gagcaactcc tggagcgcgt gcggcgcaag    360
gtgcccgcgc tgcgcagcga cgacggccgc tggcgccccg aggacctggg ccggctgctg    420
ggcgaggtgc aggctttgcg gggagtgcag gagatcaccg aggcgcggct gcgggagctc    480
aggcagcaga acgagatctt atggagggag gtggtgactc tgcggcagag ccacggtcag    540
cagcatcgcg tcattggcaa gctgatccag tgcctctttg ggccacttca gacagggtcc    600
agcggcgcag gagctaagag aaagctgtct ctgatgctgg atgaggggag ctcatgccca    660
acaccggcca aattcaacac ctgtccttta cctggtgccc tcttgcagga tccctacttt    720
atccagtcgc ccctcccaga gaccaccttg ggcctcagca gctctcatag gaccaggggc    780
cctatcatct ctgacatcca tgaagactct ccctcccctg atgggaccag gctttctcct    840
tccagtggtg gcaggaggga gaagggcctg gcactgctca aagaagagcc ggccagccca    900
gggggggaag gcgaggccgg gctggccctg gccccaaacg agtgtgactt ctgcgtgaca    960
gccccccccc cactgtccgt ggctgtggtg caggccatcc tggaagggaa ggggaacttc   1020
agccccgagg ggcccaggaa tgcccaacag cctgaaccaa ggggtcccag ggaggtacct   1080
gacaggggga ctctgggcct ggacaggggg gcacgaagcc cagagaatct gctgcctccc   1140
atgctgcttc gggccccccc tgaaagtgtg gagcctgcag ggcccctgga tgtgctgggc   1200
cccagccatc aagggcgaga atggaccctg atggacttgg acatggagct gtccctgatg   1260
cagcccttgg gtccagagag gagtgagact gagctggcgg tcaaggggtt aaattctccg   1320
gggccaggga aggactccac acttggggca ccactcctgc tcgatgtcca agcggctttg   1380
ggaggcccag ctctcagcct tcctggagct ttaaccattt acagcacccc tgagagccga   1440
gccaactacc taggcccagg ggccaatccc tcccccctga                         1479
```

<210> SEQ ID NO 4
<211> LENGTH: 549
<212> TYPE: DNA
<213> ORGANISM: Felis catus

<400> SEQUENCE: 4

```
atgggcaatg cgcaggagcg gccctcagag acgatcgatc gcgagcggaa acgcctagtg     60
gagacgctgc aggacgactc cgggctgctg ctggatgcac tgctggcgcg cggcgtgctc    120
accgggcctg agtatgaggc gttggacgcg ctgcctgatg ccgagcgcag ggtgcgtcgc    180
ctgctgctgc tggtacaaag caagggcgag gccgcctgcc aggagctgct gcactgcgcc    240
cagcgtacta cgcgcgcgcc agacccggcc tgggactggc agcacgtggg cactggctac    300
cgggaacgca gctacgactc tccatgccct ggccactgga cgcctgaggc acctgacttg    360
aggaccgctt gccccgaaac gcccagagct tcagactgcg acgaggctgg ggtttcaggg    420
ggctcggagg cagtatccgg aaccctcgag gaactcgatc cggaagtgga agctgaagtc    480
tctgaagggg ctgagccaga gccagagcca gagcccgact ttgaggcggg tgatgagtct    540
gaagattcc                                                            549
```

<210> SEQ ID NO 5

<211> LENGTH: 285
<212> TYPE: DNA
<213> ORGANISM: Homo sapiens

<400> SEQUENCE: 5
atgggctctg agctggagac ggcgatggag accctcatca acgtgttcca cgcccactcg 60
ggcaaagagg gggacaagta caagctgagc aagaaggagc tgaaagagct gctgcagacg 120
gagctctctg gcttcctgga tgcccagaag gatgtggatg ctgtggacaa ggtgatgaag 180
gagctagacg agaatggaga cggggaggtg gacttccagg agtatgtggt gcttgtggct 240
gctctcacag tggcctgtaa caatttcttc tgggagaaca gttga 285

<210> SEQ ID NO 6
<211> LENGTH: 627
<212> TYPE: DNA
<213> ORGANISM: Homo sapiens

<400> SEQUENCE: 6
atgggcaacg cccaggagcg gcccagcgag accatcgacc gggagcggaa gcggctggtg 60
gagaccctgc aggccgacag cggcctgctg ctggacgccc tgctggcccg gggcgtgctg 120
accggccccg agtacgaggc cctggacgcc ctgcccgacg ccgagcggcg ggtgcggcgg 180
ctgctgctgc tggtgcaggg caagggcgag gccgcctgcc aggagctgct gcggtgcgcc 240
cagcggaccg ccggcgcccc cgaccccgcc tgggactggc agcacgtggg ccccggctac 300
cgggaccgga gctacgaccc cccctgcccc ggccactgga cccccgaggc ccccggcagc 360
ggcaccacct gccccggcct gccccgggcc agcgaccccg acgaggccgg cggccccgag 420
ggcagcgagg ccgtgcagag cggcaccccc gaggagcccg agcccgagct ggaggccgag 480
gccagcaagg aggccgagcc cgagcccgag cccgagcccg agctggagcc cgaggccgag 540
gccgagcccg agcccgagct ggagcccgag cccgaccccg agcccgagcc cgacttcgag 600
gagcgggacg agagcgagga cagctga 627

<210> SEQ ID NO 7
<211> LENGTH: 627
<212> TYPE: DNA
<213> ORGANISM: Homo sapiens

<400> SEQUENCE: 7
atggggaatg cccaagaaag gccttctgag actatagacc gcgagcgcaa gaggcttgta 60
gaaaccttgc aggcggactc tggtctcttg ctggacgctc tgcttgcgcg gggtgttctg 120
actggaccgg agtacgaagc attggatgcc cttcctgatg cagagagacg agttagacgc 180
ctgttgcttc ttgtgcaagg caagggtgaa gccgcctgtc aagagctcct gaggtgtgct 240
caacgaaccg ccggggcgcc agatccggca tgggattggc aacatgtggg gcccggctat 300
cgggaccgga gctacgatcc accatgcccg ggtcattgga cgccggaggc tccaggatct 360
ggtacaacat gcccaggact cccaagagcc agtgaccccg atgaagctgg aggccccgag 420
ggcagtgaag ccgtacagag cggtacccca gaagaaccag aaccggagct ggaggctgaa 480
gctagtaaag aggcggaacc tgaacccgaa ccggagcctg agctcgagcc agaggctgag 540
gccgagccag agcctgaact cgaacccgaa cctgatccag aaccagagcc cgacttcgag 600
gaacgggatg agtcagagga ttcttga 627

<210> SEQ ID NO 8
<211> LENGTH: 285

<212> TYPE: DNA
<213> ORGANISM: Homo sapiens

<400> SEQUENCE: 8
atgggcagcg agctggagac cgccatggag accctgatca acgtgttcca cgcccacagc 60
ggcaaggagg gcgacaagta caagctgagc aagaaggagc tgaaggagct gctgcagacc 120
gagctgagcg gcttcctgga cgcccagaag gacgtggacg ccgtggacaa ggtgatgaag 180
gagctggacg agaacggcga cggcgaggtg gacttccagg agtacgtggt gctggtggcc 240
gccctgaccg tggcctgcaa caacttcttc tgggagaaca gctga 285

<210> SEQ ID NO 9
<211> LENGTH: 2628
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1949)..(1949)
<223> OTHER INFORMATION: n is a, c, g, or t
<220> FEATURE:
<221> NAME/KEY: misc_feature
<222> LOCATION: (2060)..(2060)
<223> OTHER INFORMATION: n is a, c, g, or t
<220> FEATURE:
<221> NAME/KEY: misc_feature
<222> LOCATION: (2069)..(2069)
<223> OTHER INFORMATION: n is a, c, g, or t
<220> FEATURE:
<221> NAME/KEY: misc_feature
<222> LOCATION: (2078)..(2078)
<223> OTHER INFORMATION: n is a, c, g, or t
<220> FEATURE:
<221> NAME/KEY: misc_feature
<222> LOCATION: (2114)..(2114)
<223> OTHER INFORMATION: n is a, c, g, or t
<220> FEATURE:
<221> NAME/KEY: misc_feature
<222> LOCATION: (2132)..(2132)
<223> OTHER INFORMATION: n is a, c, g, or t
<220> FEATURE:
<221> NAME/KEY: misc_feature
<222> LOCATION: (2135)..(2135)
<223> OTHER INFORMATION: n is a, c, g, or t
<220> FEATURE:
<221> NAME/KEY: misc_feature
<222> LOCATION: (2141)..(2141)
<223> OTHER INFORMATION: n is a, c, g, or t
<220> FEATURE:
<221> NAME/KEY: misc_feature
<222> LOCATION: (2156)..(2156)
<223> OTHER INFORMATION: n is a, c, g, or t

<400> SEQUENCE: 9
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt caattcacgc gtggaattcg cccttaacgg gcccccccctc gaggtcggga 180 taaaagcagt ctgggctttc acatgacagc atctggggct gcggcagagg gtcgggtccg 240
aagcgctgcc ttatcagcgt ccccagccct gggaggtgac agctggctgg cttgtgtcag 300
cccctcgggc actcacgtat ctccgtccga cgggtttaaa atagcaaaac tctgaggcca 360
cacaatagct tgggcttata tgggctcctg tgggggaagg gggagcacgg agggggccgg 420
ggccgctgct gccaaaatag cagctcacaa gtgttgcatt cctctctggg cgccgggcac 480
attcctgctg gctctgcccg ccccggggtg ggcgccgggg ggaccttaaa gcctctgccc 540

-continued

```
cccaaggagc ccttcccaga cagccgccgg cacccaccgc tccgtgggac gatccccgaa    600
gctctagagg atccagcctt aaggctagag tacttaatac gactcactat aggctagcgc    660
caccatgggg aatgcccaag aaaggccttc tgagactata gaccgcgagc gcaagaggct    720
tgtagaaacc ttgcaggcgg actctggtct cttgctggac gctctgcttg cgcggggtgt    780
tctgactgga ccggagtacg aagcattgga tgcccttcct gatgcagaga gacgagttag    840
acgcctgttg cttcttgtgc aaggcaaggg tgaagccgcc tgtcaagagc tcctgaggtg    900
tgctcaacga accgccgggg cgccagatcc ggcatgggat tggcaacatg tggggcccgg    960
ctatcgggac cggagctacg atccaccatg cccgggtcat tggacgccgg aggctccagg   1020
atctggtaca acatgcccag gactcccaag agccagtgac cccgatgaag ctggaggccc   1080
cgagggcagt gaagccgtac agagcggtac cccagaagaa ccagaaccgg agctggaggc   1140
tgaagctagt aaagaggcgg aacctgaacc cgaaccggag cctgagctcg agccagaggc   1200
tgaggccgag ccagagcctg aactcgaacc cgaacctgat ccagaaccag agcccgactt   1260
cgaggaacgg gatgagtcag aggattcttg aactagtgcg taccaggtcc cctctccctc   1320
cccccccct aacgttactg gccgaagccg cttggaataa ggccggtgtg cgtttgtcta   1380
tatgttattt tccaccatat tgccgtcttt tggcaatgtg agggcccgga aacctggccc   1440
tgtcttcttg acgagcattc ctaggggtct ttcccctctc gccaaaggaa tgcaaggtct   1500
gttgaatgtc gtgaaggaag cagttcctct ggaagcttct tgaagacaaa caacgtctgt   1560
agcgaccctt tgcaggcagc ggaacccccc acctggcgac aggtgcctct gcggccaaaa   1620
gccacgtgta taagatacac ctgcaaaggc ggcacaaccc cagtgccacg ttgtgagttg   1680
gatagttgtg gaaagagtca aatggctctc ctcaagcgta ttcaacaagg ggctgaagga   1740
tgcccagaag gtaccccatt gtatgggatc tgatctgggg cctcggtgca catgctttac   1800
atgtgtttag tcgaggttaa aaaacgtcta ggccccccga accacgggga cgtggttttc   1860
ctttgaaaaa cacgatgata agcttgccac aaccttgggc caccatgggc agcgagctgg   1920
agaccgccat ggagaccctg atcaacgtnt tccacgccca cagcggcaag gagggcgaca   1980
agtacaagct gagcaagaag gagctgaagg agctgctgca gaccgagctg agcggcttcc   2040
tggacgccca gaaggacgtn gacgccgtng acaaggtnat gaaggagctg gacgagaacg   2100
gcgacggcga ggtngacttc caggagtacg tngtnctggt ngccgccctg accgtngcct   2160
gcaacaactt cttctgggag aacagctgag cggccgcatc gataccgtcg actagagctc   2220
gctgatcagc ctcgactgtg ccttctagtt gccagccatc tgttgtttgc ccctcccccg   2280
tgccttcctt gaccctggaa ggtgccactc ccactgtcct ttcctaataa aatgaggaaa   2340
ttgcatcgca ttgtctgagt aggtgtcatt ctattctggg gggtggggtg gggcaggaca   2400
gcaaggggga ggattgggaa gacaatagca ggcgataagg atcttcctag agcatggcta   2460
cgtagataag tagcatggcg ggttaatcat taactacaag gaacccctag tgatggagtt   2520
ggccactccc tctctgcgcg ctcgctcgct cactgaggcc gggcgaccaa aggtcgcccg   2580
acgcccgggc tttgcccggg cggcctcagt gagcgagcga gcgcgcag                2628
```

<210> SEQ ID NO 10
<211> LENGTH: 2628
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t

<400> SEQUENCE: 10
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt caattcacgc gtggaattcg cccttaacgg gcccccctc gaggtcggga 180 taaaagcagt ctgggctttc acatgacagc atctggggct gcggcagagg gtcgggtccg 240
aagcgctgcc ttatcagcgt ccccagccct gggaggtgac agctggctgg cttgtgtcag 300
cccctcgggc actcacgtat ctccgtccga cgggtttaaa atagcaaaac tctgaggcca 360
cacaatagct tgggcttata tgggctcctg tgggggaagg gggagcacgg agggggccgg 420
ggccgctgct gccaaaatag cagctcacaa gtgttgcatt cctctctggg cgccgggcac 480
attcctgctg gctctgcccg ccccggggtg ggcgccgggg ggaccttaaa gcctctgccc 540
cccaaggagc ccttcccaga cagccgccgg cacccaccgc tccgtgggac gatccccgaa 600
gctctagagg atccagcctt aaggctagag tacttaatac gactcactat aggctagcgc 660
caccatgggc agcgagctgg agaccgccat ggagaccctg atcaacgtnt tccacgccca 720
cagcggcaag gagggcgaca agtacaagct gagcaagaag gagctgaagg agctgctgca 780
gaccgagctg agcggcttcc tggacgccca gaaggacgtn gacgccgtng acaaggtnat 840
gaaggagctg gacgagaacg gcgacggcga ggtngacttc caggagtacg tngtnctggt 900
ngccgccctg accgtngcct gcaacaactt cttctgggag aacagctgaa ctagtgcgta 960
ccaggtcccc tctccctccc ccccccctaa cgttactggc cgaagccgct tggaataagg 1020
ccggtgtgcg tttgtctata tgttattttc caccatattg ccgtcttttg gcaatgtgag 1080
ggcccggaaa cctggccctg tcttcttgac gagcattcct aggggtcttt cccctctcgc 1140
caaaggaatg caaggtctgt tgaatgtcgt gaaggaagca gttcctctgg aagcttcttg 1200
aagacaaaca acgtctgtag cgaccctttg caggcagcgg aacccccac ctggcgacag 1260

-continued gtgcctctgc ggccaaaagc cacgtgtata agatacacct gcaaaggcgg cacaacccca 1320
gtgccacgtt gtgagttgga tagttgtgga aagagtcaaa tggctctcct caagcgtatt 1380
caacaagggg ctgaaggatg cccagaaggt accccattgt atgggatctg atctggggcc 1440
tcggtgcaca tgctttacat gtgtttagtc gaggttaaaa aacgtctagg ccccccgaac 1500
cacggggacg tggttttcct ttgaaaaaca cgatgataag cttgccacaa ccttgggcca 1560
ccatggggaa tgcccaagaa aggccttctg agactataga ccgcgagcgc aagaggcttg 1620
tagaaacctt gcaggcggac tctggtctct tgctggacgc tctgcttgcg cggggtgttc 1680
tgactggacc ggagtacgaa gcattggatg cccttcctga tgcagagaga cgagttagac 1740
gcctgttgct tcttgtgcaa ggcaagggtg aagccgcctg tcaagagctc ctgaggtgtg 1800
ctcaacgaac cgccggggcg ccagatccgg catgggattg gcaacatgtg ggcccggct 1860 atcgggaccg gagctacgat ccaccatgcc cgggtcattg gacgccggag gctccaggat 1920
ctggtacaac atgcccagga ctcccaagag ccagtgaccc cgatgaagct ggaggccccg 1980
agggcagtga agccgtacag agcggtaccc cagaagaacc agaaccggag ctggaggctg 2040
aagctagtaa agaggcggaa cctgaacccg aaccggagcc tgagctcgag ccagaggctg 2100
aggccgagcc agagcctgaa ctcgaacccg aacctgatcc agaaccagag cccgacttcg 2160
aggaacggga tgagtcagag gattcttgag cggccgcatc gataccgtcg actagagctc 2220
gctgatcagc ctcgactgtg ccttctagtt gccagccatc tgttgtttgc ccctcccccg 2280
tgccttcctt gaccctggaa ggtgccactc ccactgtcct ttcctaataa aatgaggaaa 2340
ttgcatcgca ttgtctgagt aggtgtcatt ctattctggg gggtggggtg gggcaggaca 2400
gcaaggggga ggattgggaa gacaatagca ggcgataagg atcttcctag agcatggcta 2460
cgtagataag tagcatggcg ggttaatcat taactacaag gaacccctag tgatggagtt 2520
ggccactccc tctctgcgcg ctcgctcgct cactgaggcc gggcgaccaa aggtcgcccg 2580
acgcccgggc tttgcccggg cggcctcagt gagcgagcga gcgcgcag 2628

<210> SEQ ID NO 11
<211> LENGTH: 2628
<212> TYPE: DNA
<213> ORGANISM: Artificial Sequence
<220> FEATURE:
<223> OTHER INFORMATION: Synthetic

<400> SEQUENCE: 11
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt caattcacgc gtggaattcg cccttaacgg gccccccctc gaggtcggga 180
taaaagcagt ctgggctttc acatgacagc atctggggct gcggcagagg gtcgggtccg 240
aagcgctgcc ttatcagcgt ccccagccct gggaggtgac agctggctgg cttgtgtcag 300
cccctcgggc actcacgtat ctccgtccga cgggtttaaa atagcaaaac tctgaggcca 360
cacaatagct tgggcttata tgggctcctg tgggggaagg gggagcacgg agggggccgg 420
ggccgctgct gccaaaatag cagctcacaa gtgttgcatt cctctctggg cgccgggcac 480
attcctgctg gctctgcccg ccccggggtg ggcgccgggg ggaccttaaa gcctctgccc 540
cccaaggagc ccttcccaga cagccgccgg cacccaccgc tccgtgggac gatccccgaa 600
gctctagagg atccagcctt aaggctagag tacttaatac gactcactat aggctagcgc 660
caccatgggc tctgagctgg agacggcgat ggagaccctc atcaacgtgt tccacgccca 720

```
ctcgggcaaa gagggggaca agtacaagct gagcaagaag gagctgaaag agctgctgca    780
gacggagctc tctggcttcc tggatgccca gaaggatgtg gatgctgtgg acaaggtgat    840
gaaggagcta gacgagaatg gagacgggga ggtggacttc caggagtatg tggtgcttgt    900
ggctgctctc acagtggcct gtaacaattt cttctgggag aacagttgaa ctagtgcgta    960
ccaggtcccc tctccctccc ccccccctaa cgttactggc cgaagccgct tggaataagg   1020
ccggtgtgcg tttgtctata tgttattttc caccatattg ccgtcttttg gcaatgtgag   1080
ggcccggaaa cctggccctg tcttcttgac gagcattcct aggggtcttt cccctctcgc   1140
caaaggaatg caaggtctgt tgaatgtcgt gaaggaagca gttcctctgg aagcttcttg   1200
aagacaaaca acgtctgtag cgaccctttg caggcagcgg aaccccccac ctggcgacag   1260
gtgcctctgc ggccaaaagc cacgtgtata agatacacct gcaaaggcgg cacaacccca   1320
gtgccacgtt gtgagttgga tagttgtgga aagagtcaaa tggctctcct caagcgtatt   1380
caacaagggg ctgaaggatg cccagaaggt accccattgt atgggatctg atctggggcc   1440
tcggtgcaca tgctttacat gtgtttagtc gaggttaaaa aacgtctagg ccccccgaac   1500
cacggggacg tggttttcct ttgaaaaaca cgatgataag cttgccacaa ccttgggcca   1560
ccatggggaa tgcccaagaa aggccttctg agactataga ccgcgagcgc aagaggcttg   1620
tagaaacctt gcaggcggac tctggtctct tgctggacgc tctgcttgcg cggggtgttc   1680
tgactggacc ggagtacgaa gcattggatg cccttcctga tgcagagaga cgagttagac   1740
gcctgttgct tcttgtgcaa ggcaagggtg aagccgcctg tcaagagctc ctgaggtgtg   1800
ctcaacgaac cgccggggcg ccagatccgg catgggattg gcaacatgtg ggcccggct    1860
atcgggaccg gagctacgat ccaccatgcc cgggtcattg gacgccggag gctccaggat   1920
ctggtacaac atgcccagga ctcccaagag ccagtgaccc cgatgaagct ggaggccccg   1980
agggcagtga agccgtacag agcggtaccc cagaagaacc agaaccggag ctggaggctg   2040
aagctagtaa agaggcggaa cctgaacccg aaccggagcc tgagctcgag ccagaggctg   2100
aggccgagcc agagcctgaa ctcgaacccg aacctgatcc agaaccagag cccgacttcg   2160
aggaacggga tgagtcagag gattcttgag cggccgcatc gataccgtcg actagagctc   2220
gctgatcagc ctcgactgtg ccttctagtt gccagccatc tgttgtttgc ccctcccccg   2280
tgccttcctt gaccctggaa ggtgccactc ccactgtcct ttcctaataa aatgaggaaa   2340
ttgcatcgca ttgtctgagt aggtgtcatt ctattctggg gggtggggtg gggcaggaca   2400
gcaaggggga ggattgggaa gacaatagca ggcgataagg atcttcctag agcatggcta   2460
cgtagataag tagcatggcg ggttaatcat taactacaag gaacccctag tgatggagtt   2520
ggccactccc tctctgcgcg ctcgctcgct cactgaggcc gggcgaccaa aggtcgcccg   2580
acgcccgggc tttgcccggg cggcctcagt gagcgagcga gcgcgcag                2628
```

<210> SEQ ID NO 12
<211> LENGTH: 2628
<212> TYPE: DNA
<213> ORGANISM: Artificial Sequence
<220> FEATURE:
<223> OTHER INFORMATION: Synthetic

<400> SEQUENCE: 12

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
```

-continued

```
aagatcaatt caattcacgc gtggaattcg cccttaacgg gcccccccc gaggtcggga    180
taaaagcagt ctgggctttc acatgacagc atctggggct gcggcagagg gtcgggtccg    240
aagcgctgcc ttatcagcgt ccccagccct gggaggtgac agctggctgg cttgtgtcag    300
cccctcgggc actcacgtat ctccgtccga cgggtttaaa atagcaaaac tctgaggcca    360
cacaatagct tgggcttata tggctcctg tgggggaagg gggagcacgg agggggccgg    420
ggccgctgct gccaaaatag cagctcacaa gtgttgcatt cctctctggg cgccgggcac    480
attcctgctg gctctgcccg ccccggggtg ggcgccgggg ggaccttaaa gcctctgccc    540
cccaaggagc ccttcccaga cagccgccgg cacccaccgc tccgtgggac gatccccgaa    600
gctctagagg atccagcctt aaggctagag tacttaatac gactcactat aggctagcgc    660
caccatgggg aatgcccaag aaaggccttc tgagactata gaccgcgagc gcaagaggct    720
tgtagaaacc ttgcaggcgg actctggtct cttgctggac gctctgcttg cgcggggtgt    780
tctgactgga ccggagtacg aagcattgga tgcccttcct gatgcagaga gacgagttag    840
acgcctgttg cttcttgtgc aaggcaaggg tgaagccgcc tgtcaagagc tcctgaggtg    900
tgctcaacga accgccgggg cgccagatcc ggcatgggat tggcaacatg tggggcccgg    960
ctatcgggac cggagctacg atccaccatg cccgggtcat tggacgccgg aggctccagg   1020
atctggtaca acatgcccag gactcccaag agccagtgac cccgatgaag ctggaggccc   1080
cgagggcagt gaagccgtac agagcggtac cccagaagaa ccagaaccgg agctggaggc   1140
tgaagctagt aaagaggcgg aacctgaacc cgaaccggag cctgagctcg agccagaggc   1200
tgaggccgag ccagagcctg aactcgaacc cgaacctgat ccagaaccag agcccgactt   1260
cgaggaacgg gatgagtcag aggattcttg aactagtgcg taccaggtcc cctctccctc   1320
cccccccct aacgttactg gccgaagccg cttggaataa ggccggtgtg cgtttgtcta   1380
tatgttattt tccaccatat tgccgtcttt tggcaatgtg agggcccgga aacctggccc   1440
tgtcttcttg acgagcattc ctaggggtct ttcccctctc gccaaaggaa tgcaaggtct   1500
gttgaatgtc gtgaaggaag cagttcctct ggaagcttct tgaagacaaa caacgtctgt   1560
agcgaccctt tgcaggcagc ggaacccccc acctggcgac aggtgcctct gcggccaaaa   1620
gccacgtgta taagatacac ctgcaaaggc ggcacaaccc cagtgccacg ttgtgagttg   1680
gatagttgtg gaaagagtca aatggctctc ctcaagcgta ttcaacaagg ggctgaagga   1740
tgcccagaag gtaccccatt gtatgggatc tgatctgggg cctcggtgca catgctttac   1800
atgtgtttag tcgaggttaa aaaacgtcta ggccccccga accacgggga cgtggttttc   1860
ctttgaaaaa cacgatgata agcttgccac aaccttgggc caccatgggc tctgagctgg   1920
agacggcgat ggagaccctc atcaacgtgt tccacgccca ctcgggcaaa gagggggaca   1980
agtacaagct gagcaagaag gagctgaaag agctgctgca gacggagctc tctggcttcc   2040
tggatgccca gaaggatgtg gatgctgtgg acaaggtgat gaaggagcta gacgagaatg   2100
gagacgggga ggtggacttc caggagtatg tggtgcttgt ggctgctctc acagtggcct   2160
gtaacaattt cttctgggag aacagttgag cggccgcatc gataccgtcg actagagctc   2220
gctgatcagc ctcgactgtg ccttctagtt gccagccatc tgttgtttgc ccctcccccg   2280
tgccttcctt gaccctggaa ggtgccactc ccactgtcct ttcctaataa aatgaggaaa   2340
ttgcatcgca ttgtctgagt aggtgtcatt ctattctggg gggtggggtg gggcaggaca   2400
gcaaggggga ggattgggaa gacaatagca ggcgataagg atcttcctag agcatggcta   2460
cgtagataag tagcatggcg ggttaatcat taactacaag gaacccctag tgatggagtt   2520
```

ggccactccc tctctgcgcg ctcgctcgct cactgaggcc gggcgaccaa aggtcgcccg 2580
acgcccgggc tttgcccggg cggcctcagt gagcgagcga gcgcgcag 2628

<210> SEQ ID NO 13
<211> LENGTH: 208
<212> TYPE: PRT
<213> ORGANISM: Homo sapiens

<400> SEQUENCE: 13

Met Gly Asn Ala Gln Glu Arg Pro Ser Glu Thr Ile Asp Arg Glu Arg
1 5 10 15

Lys Arg Leu Val Glu Thr Leu Gln Ala Asp Ser Gly Leu Leu Leu Asp
20 25 30

Ala Leu Leu Ala Arg Gly Val Leu Thr Gly Pro Glu Tyr Glu Ala Leu
35 40 45

Asp Ala Leu Pro Asp Ala Glu Arg Arg Val Arg Arg Leu Leu Leu Leu
50 55 60

Val Gln Gly Lys Gly Glu Ala Ala Cys Gln Glu Leu Leu Arg Cys Ala
65 70 75 80

Gln Arg Thr Ala Gly Ala Pro Asp Pro Ala Trp Asp Trp Gln His Val
85 90 95

Gly Pro Gly Tyr Arg Asp Arg Ser Tyr Asp Pro Pro Cys Pro Gly His
100 105 110

Trp Thr Pro Glu Ala Pro Gly Ser Gly Thr Thr Cys Pro Gly Leu Pro
115 120 125

Arg Ala Ser Asp Pro Asp Glu Ala Gly Gly Pro Glu Gly Ser Glu Ala
130 135 140

Val Gln Ser Gly Thr Pro Glu Glu Pro Glu Pro Glu Leu Glu Ala Glu
145 150 155 160

Ala Ser Lys Glu Ala Glu Pro Glu Pro Glu Pro Glu Pro Glu Leu Glu
165 170 175

Pro Glu Ala Glu Ala Glu Pro Glu Pro Glu Leu Glu Pro Glu Pro Asp
180 185 190

Pro Glu Pro Glu Pro Asp Phe Glu Glu Arg Asp Glu Ser Glu Asp Ser
195 200 205

<210> SEQ ID NO 14
<211> LENGTH: 94
<212> TYPE: PRT
<213> ORGANISM: Homo sapiens

<400> SEQUENCE: 14

Met Gly Ser Glu Leu Glu Thr Ala Met Glu Thr Leu Ile Asn Val Phe
1 5 10 15

His Ala His Ser Gly Lys Glu Gly Asp Lys Tyr Lys Leu Ser Lys Lys
20 25 30

Glu Leu Lys Glu Leu Leu Gln Thr Glu Leu Ser Gly Phe Leu Asp Ala
35 40 45

Gln Lys Asp Val Asp Ala Val Asp Lys Val Met Lys Glu Leu Asp Glu
50 55 60

Asn Gly Asp Gly Glu Val Asp Phe Gln Glu Tyr Val Val Leu Val Ala
65 70 75 80

Ala Leu Thr Val Ala Cys Asn Asn Phe Phe Trp Glu Asn Ser
85 90

<210> SEQ ID NO 15
<211> LENGTH: 627
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:

-continued

<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (567)..(567)

<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t

<400> SEQUENCE: 15
atgggcaacn nccaggagcg gcccagcgag accatcgacc gggagcggaa gcggctggtg 60
gagaccctgc aggccgacag cggcctgctg ctggacgccc tgctggcccg gggcgtgctg 120
nccggccccg agtacgaggc cctggacgcc ctgcccgacg ccgagcggcg ggtgcggcgg 180
ctgctgctgc tggtgcagng caagggcgag gccgcctgcc aggagctgct gcngtgcgcc 240
cagcggaccg ccngngcccc cgaccccgcc tgggactggc agcacgtggg cnccggctac 300
cgggancgga gctnngacnc cncctgcncc ggccactgga cccccgaggc ccccggcagc 360
ngcaccacct gccccgnnct gccccgggcc nncgacnncg ncgagnccgg cgnccccgnn 420
ggcagcgagg ccgnncagag cggcanccnn gaggagcccg ancccgagct ggaggccgnn 480
gccnnnnnnn nnnnngagcn ngagnncgag cccnagnnng anctggagcc cgagnccgag 540
gccgagcccg agcccgagct ggagcnngag cccgancccg agcccgagcc cgacntngag 600
gnnngngacg agagcgagga cagctga 627

<210> SEQ ID NO 16
<211> LENGTH: 615
<212> TYPE: DNA
<213> ORGANISM: Canis lupus

<400> SEQUENCE: 16
atgggcaaca gccaggagcg gcccagcgag accatcgacc gggagcggaa gcggctggtg 60
gagaccctgc aggccgacag cggcctgctg ctggacgccc tgctggcccg gggcgtgctg 120
gccggccccg agtacgaggc cctggacgcc ctgcccgacg ccgagcggcg ggtgcggcgg 180
ctgctgctgc tggtgcagag caagggcgag gccgcctgcc aggagctgct gctgtgcgcc 240
cagcggaccg cccgggcccc cgaccccgcc tgggactggc agcacgtggg caccggctac 300
cgggagcgga gctgggacgc cgcctgcgcc ggccactgga cccccgaggc ccccggcagc 360
agcaccacct gccccgagct gccccgggcc gccgactgcg gcgagcccgg cgcccccggc 420
ggcagcgagg ccgcccagag cggcagcctg gaggagcccg accccgagct ggaggccggc 480
gccgagctgg agagcgagcc ccagatggac ctggagcccg agcccgaggc cgagcccgag 540
cccgagctgg agcgggagcc cgagcccgag cccgagcccg acctggaggc cggcgacgag 600
agcgaggaca gctga 615

<210> SEQ ID NO 17
<211> LENGTH: 627
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (91)..(91)

<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:

<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (555)..(555)

-continued

<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t

<400> SEQUENCE: 17
atgggcaacg cncaggagcg gccnnnngag acnatcgacc gngagcggaa ncgnctggtn 60
gagacnctgc aggcngacnn nggnctgctg ntggacgcnc tgctggcncg gggcgtgctn 120
accggnccng agtacgaggc nntggangcn ctgccngang ccgagcgnng ggtgcgncgn 180
ctnctgctgc tggtgcaggg caagggcgag gccgcctgcc aggagctgct ncgntgngcc 240
cagcgnaccg cnggcgcncc ngaccccgcn tgggactggc agcacgtggg nccnggctac 300
cgggaccgna gctangaccc nccntgcccn ggccactgga cnccngaggc ncccggcnnn 360
ggnaccacnt gccccggnnt gcccngngcn nnngacccng acgaggccgg nggcccngag 420
ggcnncgagg cngtgcannn cggnaccccn gaggagccng agccngagct ggangcngag 480
gccnnnaang aggcngancc ngagccngag ccngagccng agctggancc cgaggcngan 540
gcnganccng agccnganct ggagccngan ccngacccng agcccgagcc cgacttcgag 600
ganngggacg agnncganga nnnctga 627

<210> SEQ ID NO 18
<211> LENGTH: 627
<212> TYPE: DNA
<213> ORGANISM: Homo sapiens

<400> SEQUENCE: 18
atgggcaacg cgcaggagcg gccgtcagag actatcgacc gcgagcggaa acgcctggtc 60
gagacgctgc aggcggactc gggactgctg ttggacgcgc tgctggcgcg gggcgtgctc 120
accgggccag agtacgaggc attggatgca ctgcctgatg ccgagcgcag ggtgcgccgc 180
ctactgctgc tggtgcaggg caagggcgag gccgcctgcc aggagctgct acgctgtgcc 240
cagcgtaccg cgggcgcgcc ggaccccgct tgggactggc agcacgtggg tccgggctac 300
cgggaccgca gctatgaccc tccatgccca ggccactgga cgccggaggc acccggctcg 360
gggaccacat gccccgggtt gcccagagct tcagaccctg acgaggccgg gggccctgag 420
ggctccgagg cggtgcaatc cgggaccccg gaggagccag agccagagct ggaagctgag 480
gcctctaaag aggctgaacc ggagccggag ccagagccag agctggaacc cgaggctgaa 540
gcagaaccag agccggaact ggagccagaa ccggacccag agcccgagcc cgacttcgag 600
gaaagggacg agtccgaaga ttcctga 627

<210> SEQ ID NO 19
<211> LENGTH: 285
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (72)..(72)

<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t

<400> SEQUENCE: 19
atgggcnnng agctggagac ngcnatggag accctnatca acgtgttcca cgcccacnnn 60
ggcaangagg gngacaagta caagctgagc aagaaggagc tgaangagct gctgcagacn 120
gagctnnnng gcttcctgga ngcccagaag gangtggang cngtggacaa ggtgatgaag 180
gagctngacg agaanggnga cggngaggtg gacttccagg agtangtggt gctngtggcn 240
gcnctnacng tggcctgnaa caanttcttc tgggagaaca gntga 285

<210> SEQ ID NO 20
<211> LENGTH: 285
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t

<400> SEQUENCE: 20
atgggcagcg agctggagac cgccatggag accctgatca acgtgttcca cgcccacagc 60
ggcaaggagg gcnacaagta caagctgagc aagaaggagc tgaaggagct gctgcagacc 120
gagctgagcg gcttcctgga cgcccagaag gacgnngacg ccgtggacaa ggtgatgaag 180
gagctggacg agaacggcga cggcgaggtg gacttccagg agtacgtggt gctggtggcc 240
gccctgaccg tggcctgcaa caacttcttc tgggagaaca gctga 285

<210> SEQ ID NO 21
<211> LENGTH: 285
<212> TYPE: DNA
<213> ORGANISM: Canis lupus

<400> SEQUENCE: 21
atgggcagcg agctggagac cgccatggag accctgatca acgtgttcca cgcccacagc 60
ggcaaggagg gcaacaagta caagctgagc aagaaggagc tgaaggagct gctgcagacc 120
gagctgagcg gcttcctgga cgcccagaag gacgccgacg ccgtggacaa ggtgatgaag 180
gagctggacg agaacggcga cggcgaggtg gacttccagg agtacgtggt gctggtggcc 240
gccctgaccg tggcctgcaa caacttcttc tgggagaaca gctga 285

AAV CARDIAC GENE THERAPY FOR CARDIOMYOPATHY IN HUMANS

RELATED APPLICATIONS

This application is a national stage filing under 35 U.S.C. 371 of International Patent Application Serial No. PCT/US2020/042663, filed Jul. 17, 2020, entitled "AAV CARDIAC GENE THERAPY FOR CARDIOMYOPATHY IN HUMANS", which claims the benefit under 35 U.S.C. 119(e) of U.S. Provisional Application Ser. No. 62/876,540, filed Jul. 19, 2019, entitled "AAV CARDIAC GENE THERAPY FOR CARDIOMYOPATHY IN HUMANS", the entire contents of each of which are incorporated herein by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 27, 2021, is named U119770160US02-SEQ-EPG and is 46,868 bytes in size.

BACKGROUND

Cardiomyopathy is the second most common cause of heart disease in subjects and medical management of the secondary signs is the only therapeutic option. The prognosis for affected subjects depends on the stage of disease and the breed. Heart function is critically dependent upon calcium-dependent signaling. During heart disease, malfunctioning of calcium channels within cardiac cells promotes calcium cycling abnormalities, further inhibiting heart function. Gene transfer strategies to reduce calcium cycling abnormalities have been shown to ameliorate heart disease in small and large animal models, as well as in human clinical trials.

Dilated cardiomyopathy (DCM) is the most common type of human cardiomyopathy, occurring mostly in adults 20 to 60. DCM affects the heart's ventricles and atria, the lower and upper chambers of the heart, respectively. Most forms of DCM are acquired forms from a number of causes that include coronary heart disease, heart attack, high blood pressure, diabetes, thyroid disease, viral hepatitis and viral infections that inflame the heart muscle. Alcohol abuse and certain drugs, such as cocaine and amphetamines, as well as at least two drugs used to treat cancer (doxorubicin and daunorubicin), can also lead to DCM. In addition, there are a number of genetic forms of DCM, including, but not limited to the DCM associated with Duchenne and Becker muscular dystrophies. In the case of certain forms of Becker muscular dystrophy, as well as in most cases of Duchenne muscular dystrophy, the cardiomyopathy can ultimately limit the patient's survival.

SUMMARY

In humans, dilated cardiomyopathy is the most common type of cardiomyopathy and can stem from a number of acquired as well as genetic conditions. As in dogs and other animal models, while the origins of the disease are rooted in calcium handling dysfunction, the ultimate progression of the disease is driven by mitochondrial dysfunction and/or stretch-induced apoptosis of the cardiomyocytes. While addressing calcium handling alone may be efficacious at early disease stages, addressing the combination of calcium handling, mitochondrial dysfunction, and apoptosis will be necessary to treat all forms of DCM and at all stages of disease progression.

Disclosed herein are gene delivery approaches for treatment of human subjects with cardiomyopathy and congestive heart failure. These approaches comprise the expression of S100A1 to address calcium handling and expression of ARC (Apoptosis Repressor with Caspase Recruitment Domain) to block all sources of apoptosis and normalize mitochondrial function. Expression of S100A1 and ARC transgenes through the disclosed self-complementary AAV vector approach, is rapid (i.e. within hours), which is critical in counteracting the effects of end-stage heart failure and restricted to the heart. Thus, these approaches address all three drivers of DCM onset and progression and thus should be applicable to any form of DCM at any stage of disease progression.

In addition, disclosed herein is a series of transgenes for gene delivery that code for the human-derived proteins ARC and S100A1. These transgenes may comprise cDNA sequences, and these sequences may be delivered and expressed using a recombinant adeno-associated virus (AAV) vector system. The disclosed cDNA sequences may be delivered with any type of gene delivery vector, including but not limited to all forms of AAV, lentiviruses, liposomes and exosomes.

In particular embodiments, these sequences may be expressed using a self-complementary version of AAV vector DNA that comprises i) a wild type or an optimized cDNA encoding human ARC and ii) a wild type or an optimized cDNA encoding human S100A1. The ARC and s100A1 cDNA sequences may be positioned such that ARC comprises the first cDNA and S100A1 comprises the second cDNA in the 5' to 3' direction, or vice versa. In other embodiments, these cDNA sequences may be expressed using two promoters, rather than a promoter and IRES.

Expression of these cDNA sequences may be operably controlled by a cardiac troponin T promoter (cTnT) positioned 5' of the first cDNA, and/or an internal ribosome entry site (IRES) positioned 5' of the second cDNA. The cTnT promoter restricts expression of the two transgenes to cardiomyocytes when AAV is introduced via the circulation into the heart and other tissues, or via direct injection. The resulting expression of ARC prevents apoptosis when expressed in cardiomyocytes and helps normalize the mitochondrial membrane potential, reducing free radical generation and improving mitochondrial function. S100A1 expression leads to improved calcium pumping into the sarcoplasmic reticulum (SR) of cardiomyocytes by the sarco/endoplasmic reticulum $Ca^{2+}$-ATPase (SERCA) pump (e.g., the SERCA isoform 2a pump, or SERCA2a) and decreased calcium leak from the SR via the ryanodine receptor channel. The combination allows the normalization of cardiomyocyte calcium handling and improved systolic and diastolic function in the heart.

The combined effects of an absence of apoptotic effects, improved mitochondrial function, and improved calcium handling slows progression of heart failure and improves cardiac function. The disclosed rAAV vectors may be effective in all forms of human cardiomyopathy and heart failure. As such, the disclosed rAAV vectors may be delivered to subject, e.g., a human subject, suffering from a disease, disorder or condition comprising poor cardiac function, e.g., human cardiomyopathy and heart failure.

Accordingly, some aspects of the present disclosure provide recombinant adeno-associated virus (rAAV) vectors for delivering transgenes into the heart of a subject. In some embodiments, such rAAV vectors include at least two transgenes, one encoding an S100 family protein and one encoding an apoptotic inhibitor. Such rAAV vectors may include, from 5' to 3', in order, a first adeno-associated virus (AAV) inverted terminal repeat (ITR) sequence, a promoter operably linked to the transgenes, and a second AAV inverted terminal repeat (ITR) sequence. In some embodiments, two transgenes are operably linked to the same single promoter. In other embodiments, each transgene is operably linked to a separate promoter. In some embodiments, the rAAV vector also includes at least one polyadenylation signal (e.g., positioned 3' of two transgenes expressed from a single promoter or 3' of one or both transgenes expressed from different promoters). Aspects of the disclosure provide recombinant adeno-associated virus (rAAV) nucleic acid vector for delivering two or more transgenes into the heart of a subject, wherein said vector comprises, from 5' to 3', a first adeno-associated virus (AAV) inverted terminal repeat (ITR) sequence, two or more transgenes and a promoter operably linked to the two or more transgenes, a polyadenylation signal, and a second AAV inverted terminal repeat (ITR) sequence, wherein the two or more transgenes comprise an S100 family protein and an apoptotic inhibitor.

The transgenes of the present disclosure may comprise an S100 family protein and an apoptotic inhibitor. For example, the S100 family protein may comprise cardiac S100 calcium-binding protein A1 (cS100A1), or a variant thereof. In another example, the apoptotic inhibitor may comprise a cardiac Apoptosis Repressor with Caspase Recruitment Domain (cARC) or a variant thereof.

In some embodiments, one or more of the transgenes of the present disclosure are naturally-occurring or wild-type sequences. In some embodiments, one or more transgenes (e.g. the cARC transgene) are codon-optimized for expression in humans.

In various embodiments, provided herein are rAAV vectors comprising a promoter, a polyadenylation (polyA) signal and a polynucleotide comprising two or more transgenes. In some embodiments, a first transgene encodes an S100 family protein (e.g. cS100A1 or variant thereof) and a second transgene encodes a cARC. In particular embodiments, the S100 family protein and cARC transgenes are derived from humans.

In some embodiments, the first transgene (encoding an S100 family protein) of the polynucleotide comprises the nucleotide sequence set forth as SEQ ID NO: 5. Alternatively, the first transgene may comprise the nucleotide sequence set forth as SEQ ID NO: 8.

In some embodiments, the first transgene (encoding an S100 family protein) may comprise a nucleotide sequence that is at least 90%, at least 95%, or at least 99.5% identical to any one of SEQ ID NOs: 19-21. The first transgene may comprise the nucleotide sequence of any one of SEQ ID NOs: 19-21. In particular embodiments, the first transgene may comprise the nucleotide sequence set forth as SEQ ID NO: 21.

The second transgene of the polynucleotide may comprise a nucleotide sequence that is at least 90%, at least 95%, or at least 99.5% identical to SEQ ID NO: 6. Alternatively, the second transgene may comprise a nucleotide sequence that is at least 90%, at least 95%, or at least 99.5% identical to SEQ ID NO: 7. The second transgene may comprise any one of the sequences of SEQ ID NOs: 6 and 7.

In some embodiments, the second transgene (encoding a cARC protein) may comprise a nucleotide sequence that is at least 90%, at least 95%, or at least 99.5% identical to any one of SEQ ID NOs: 15-18. The first transgene may comprise any of the nucleotide sequences set forth as SEQ ID NOs: 15-18. In particular embodiments, the first transgene comprises the sequence of SEQ ID NO: 16.

In some embodiments, an Internal Ribosome Entry Site (IRES) is present between the two or more transgenes (e.g., between the cS100A1 transgene and cARC transgene). In some embodiments, the transgene encoding the S100 family protein is 5' to the transgene encoding the apoptotic inhibitor. In other embodiments, the transgene encoding the apoptotic inhibitor is 5' to the transgene encoding the S100 family protein.

Further provided herein are rAAV particles containing the rAAV vectors disclosed herein, encapsidated in AAV capsids. Other aspects of the present disclosure include compositions containing the rAAV particles described herein. Such compositions may be administered to a subject for gene therapy for heart disease. In some embodiments, the heart disease causes heart failure in the subject. In some embodiments, the heart disease is cardiomyopathy. In other embodiments, the heart disease is hypertrophic cardiomyopathy or dilated cardiomyopathy. In other embodiments, the heart disease is acute ischemia.

The compositions of the present disclosure may be administered to the subject via different routes. In some embodiments, the composition is administered via injection into the heart of the subject. In some embodiments, the administration of the composition results in expression of the transgenes (e.g., two or more transgenes) in the subject's heart. In various embodiments, the step of administering the composition results in improved cardiac function in the subject, such as improved cardiac function in the subject for more than 10 months. In some embodiments, administration results in improved cardiac function for more than 12 months, more than 14 months, more than 16 months, more than 17 months, more than 20 months, more than 22 months, or more than 24 months.

BRIEF DESCRIPTION OF THE DRAWINGS

The following drawings form part of the present specification and are included to further demonstrate certain aspects of the present disclosure. The disclosure may be better understood by reference to the following description taken in conjunction with the accompanying drawings, in which like reference numerals identify like elements:

FIG. 3 depicts systolic MRI imaging from a treated muscular dystrophy dog at baseline and several weeks after gene delivery. The data support stable or slightly improved left ventricular systolic function post treatment, with a mild reduction in systolic volume suggesting improved contractility and an increase in left ventricular cardiac output.

FIG. 13 illustrates a sequence alignment between codon-optimized and native human S100A1 cDNA sequences. Sequences correspond to SEQ ID NOs: 19, 5, and 8 from top to bottom.

FIG. 14 illustrates a sequence alignment between codon-optimized canine S100A1 cDNA sequence and codon-optimized human S100A1 cDNA sequence. Sequences correspond to SEQ ID NOs: 20, 8, and 21 from top to bottom.

DETAILED DESCRIPTION

Figure 1:
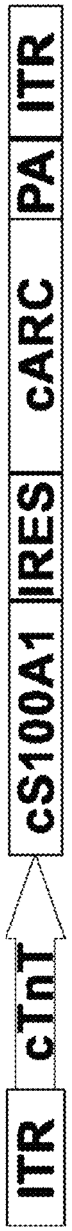
FIG. 1 depicts a diagram of an exemplary AAV construct. A first AAV inverted terminal repeat (ITR) is followed by the cardiac troponin T promoter (cTnT), then a sequence encoding S100 calcium-binding protein A1 (cS100A1), followed by an internal ribosomal entry site (IRES), followed by a sequence encoding Apoptosis Repressor with Caspase Recruitment Domain (cARC), followed by a polyadenylation (PA) sequence, and a second AAV ITR.

The present disclosure relates to compositions and methods of cardiac gene therapy for heart diseases, e.g., cardiomyopathy, in a human subject. The methods of the present disclosure relate to the use of recombinant AAV (rAAV) particles for the concurrent delivery and expression of two or more transgenes. The transgenes of the present disclosure comprise at least two classes of proteins each having specific function to address different aspects of the heart diseases. One class of transgenes regulates the calcium signaling in cardiomyocytes, e.g., the S100 family proteins. The other class of transgenes comprises apoptosis repressors. In some embodiments, the transgenes may be cardiac S100 calcium-binding protein A1 (cS100A1) or a variant thereof, and cardiac Apoptosis Repressor with Caspase Recruitment Domain (cARC) or a variant thereof.

The compositions and methods of the present disclosure are based on, at least in part, the synergistic effects of two transgenes, e.g., S100A1 and ARC, when they are delivered and expressed concurrently in the heart of the subject. The S100A1 protein improves aspects of calcium handling, including normalization of sarcoplasmic reticular calcium transients leading to normalization of contractile function. The ARC protein blocks apoptosis initiated by mitochondrial and non-mitochondrial mechanisms (such as stretch-induced apoptosis), and improves mitochondrial function. In other words, S100A1 and ARC address two separate components of cardiac failure (calcium handling dysfunction and apoptosis) with synergistic benefits, leading to better long-term therapeutic outcomes. Further, the compositions and methods of the present disclosure are effective at any disease stage of heart failure.

Further provided herein are methods of making rAAV particles suitable for delivering transgenes, e.g., S100A1 and ARC or a variant thereof, into the heart of the subject. Such rAAV particles may comprise a recombinant AAV genome, comprising nucleic acid molecules encoding the transgenes, wherein said nucleic acid molecules are encapsidated by AAV capsid proteins. In some embodiments, the rAAV particles include recombinant adeno-associated virus (rAAV) nucleic acid vector. The recombinant AAV genome is a single-stranded DNA that may further comprise sequence elements that facilitate the integration of the AAV genome into the host genome and the expression of the transgenes. For example, the recombinant AAV genome may comprise tissue-specific promoters to ensure the expression of the transgenes in target tissues or organs. Such rAAV particles may be used in a composition for the treatment of heart conditions.

Thus, the present disclosure further provides recombinant adeno-associated virus (rAAV) vectors for delivering transgenes into the heart of a subject. In some embodiments, the disclosed rAAV vectors include at least two transgenes, one encoding an S100 family protein and one encoding an apoptotic inhibitor. These rAAV vectors may include, from 5' to 3', in order, a first adeno-associated virus (AAV) inverted terminal repeat (ITR) sequence, a promoter operably linked to the transgenes, and a second AAV inverted terminal repeat (ITR) sequence. In some embodiments, two transgenes are operably linked to the same single promoter. In other embodiments, each transgene is operably linked to a separate promoter. In some embodiments, the rAAV vector also includes at least one polyadenylation signal (e.g., positioned 3' of two transgenes expressed from a single promoter or 3' of one or both transgenes expressed from different promoters).

The disclosure further provides recombinant adeno-associated virus (rAAV) nucleic acid vector for delivering two or more transgenes into the heart of a subject. In some embodiments, the rAAV vector comprises exactly two transgenes. In some embodiments, the rAAV vector comprises three transgenes. In some embodiments, said vector comprises, from 5' to 3', a first adeno-associated virus (AAV) inverted terminal repeat (ITR) sequence, two or more transgenes and a promoter operably linked to the two or more transgenes, a polyadenylation signal, and a second AAV inverted terminal repeat (ITR) sequence. In particular embodiments, the two or more transgenes comprise a first transgene comprising an S100 family protein and a second transgene comprising an apoptotic inhibitor.

A "transgene", as used herein, refers to a gene or genetic material that has been transferred naturally, or by any of a number of genetic engineering techniques from one organism to another. A transgene may be a protein or polypeptide of interest (e.g., S100A1, ARC) or an RNA of interest (e.g., a siRNA or microRNA). In some embodiments, one rAAV vector may comprise the coding sequence for one or more transgenes. For example, one rAAV vector may comprise the coding sequence for 1, 2, 3, 4, 5, 6, 7, 8, 9, or 10 transgenes. In some embodiments, the rAAV vectors of the present disclosure comprise the coding sequence of both S100A1 and ARC or variants thereof. In some embodiments, the rAAV vector further comprises a region encoding a Rep protein. The transgenes of the present disclosure comprise two classes of proteins each having specific function to address different aspects of one or more heart conditions. One class of transgenes may regulate the calcium signaling in cardiomyocytes, e.g., the S100 family proteins. Another class of transgenes may comprise apoptosis repressors.

As used herein, the term "variant" refers to a nucleic acid having characteristics that deviate from what occurs in nature, e.g., a "variant" is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type nucleic acid. For instance, a transgene variant is a nucleic acid comprising one or more substitutions in the nucleotides of a transgene, as compared to the wild type sequence thereof. These substitutions may be silent, i.e. they do not modify the amino acid sequence of any encoded protein (or otherwise result in a variant amino acid sequence). Alternatively, these substitutions may result in modifications to the amino acid sequence of an encoded protein, resulting in an encoded protein having one or more amino acid substitutions (e.g., having 1, 2, 3, 4, 5, 6, 7, 8, 9, 10, 10-15, or 15-20 amino acid substitutions) relative to the wild type protein sequence. These substitutions include chemical modifications as well as truncations. This term further embraces functional fragments of a wild type nucleic acid sequence. These modifications of the reference sequence may occur at the 5' or 3' ends of the reference sequence or anywhere between those positions, interspersed either individually among nucleotides in the reference sequence or in one or more contiguous groups within the reference sequence.

As a practical matter, whether any particular nucleic acid molecule is at least 80%, 85%, 90%, 95%, 96%, 97%, 98%, or 99% identical to, for instance, the nucleotide sequence of a transgene, can be determined conventionally using known computer programs. A preferred method for determining the best overall match between a query sequence (e.g., a sequence of the present disclosure) and a subject sequence, also referred to as a global sequence alignment, can be determined using the FASTDB or blastn computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Whether a nucleotide is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. For subject sequences truncated at the 5' and/or 3' ends, relative to the query sequence, the percent identity is corrected by calculating the number of nucleotides of the query sequence that are positioned 5' to or 3' to the query sequence, which are not matched/aligned with a corresponding subject nucleotide, as a percent of the total bases of the query sequence.

S100 family proteins that may be used in accordance to the present disclosure include, without limitation, S100A1, S100A2, S100A3, S100A4, S100A5, S100A6, S100A7 (e.g., psoriasin), S100A8 (e.g., calgranulin A), S100A9 (e.g., calgranulin B), S100A10, S100A11, S100A12 (e.g., calgranulin C), S100A13, S100A14, S100A15 (e.g., koebnerisin), S100A16, S100B, S100P, and S100Z, or variants thereof.

In some embodiments, the S100 family protein may be S100 calcium-binding protein A1 (S100A1). In some embodiments, the S100A1 is cardiac S100A1 (cS100A1) or a variant thereof. The cS100A1 protein is a regulator of myocardial contractility. cS100A1 protein levels are reduced in right ventricular hypertrophied tissue in a model of pulmonary hypertension. Further, S100A1 is a regulator of the genetic program underlying cardiac hypertrophy, in that S100A1 inhibits alpha1 adrenergic stimulation of hypertrophic genes, including MYH7, ACTA1 and S100B.

In cardiomyocytes, S100A1 regulates the calcium-controlled network of SR, sarcomeric, and mitochondrial function through modulation of ryanodine receptor 2 (RYR2), sarco/endoplasmic reticulum $Ca^{2+}$-ATPase (SERCA), titin, and mitochondrial F1-ATPase activity. As a result, cardiomyocytes and hearts with increased S100A1 expression show increased systolic and diastolic performance, a result of improved $Ca^{2+}$, transient amplitudes resulting from augmented SR $Ca^{2+}$ load and subsequent systolic $Ca^{2+}$ release together with decreased diastolic SR $Ca^{2+}$ leak and enhanced $Ca^{2\prime}$ re-sequestration. Concurrently, S100A1 increases mitochondrial high-energy phosphate production and thus coordinates the energy supply with the increased adenosine 5'-triphosphate (ATP) demand by the enhanced cardiomyocyte $Ca^{2+}$ turnover. Reduced S100A1 expression in cardiomyocytes is associated with reduced contractile function, corroborating the pathophysiological significance of this protein.

In some embodiments, the S100A1 cDNA (transgene) sequence of the polynucleotides of any of the disclosed rAAV vectors has 100% identity to a naturally-occurring human-derived S100A1 sequence. In other embodiments, the S100A1 cDNA sequence has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to a naturally-occurring S100A1 sequence.

In some embodiments, the S100A1 cDNA sequence is codon-optimized for expression in human cells. In some embodiments, the S100A1 cDNA (transgene) sequence comprises a sequence having 100% identity to SEQ ID NO: 5 or SEQ ID NO: 8. In other embodiments, the S100A1 cDNA sequence has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 5 or SEQ ID NO: 8.

In other embodiments, the S100A1 cDNA sequence is codon-optimized for expression in canine cells. In some embodiments, the rAAV vector comprises an S100A1 cDNA sequence that has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 21. In some embodiments, the rAAV vector comprises SEQ ID NO: 21.

Non-limiting examples of S100A1 cDNA sequences are described below.

native S100A1 (*homo sapiens*)
(SEQ ID NO: 5)

ATGGGCTCTGAGCTGGAGACGGCGATGGAGACCCTCATCAACGTGTTCCA

CGCCCACTCGGGCAAAGAGGGGGACAAGTACAAGCTGAGCAAGAAGGAGC

TGAAAGAGCTGCTGCAGACGGAGCTCTCTGGCTTCCTGGATGCCCAGAAG

GATGTGGATGCTGTGGACAAGGTGATGAAGGAGCTAGACGAGAATGGAGA

-continued

CGGGGAGGTGGACTTCCAGGAGTATGTGGTGCTTGTGGCTGCTCTCACAG

TGGCCTGTAACAATTTCTTCTGGGAGAACAGTTGA optimized S100A1 (*homo sapiens*)
(SEQ ID NO: 8)

ATGGGCAGCGAGCTGGAGACCGCCATGGAGACCCTGATCAACGTGTTCCA

CGCCCACAGCGGCAAGGAGGGCGACAAGTACAAGCTGAGCAAGAAGGAGC

TGAAGGAGCTGCTGCAGACCGAGCTGAGCGGCTTCCTGGACGCCCAGAAG

GACGTGGACGCCGTGGACAAGGTGATGAAGGAGCTGGACGAGAACGGCGA

CGGCGAGGTGGACTTCCAGGAGTACGTGGTGCTGGTGGCCGCCCTGACCG

TGGCCTGCAACAACTTCTTCTGGGAGAACAGCTGA

A nucleotide sequence alignment between a codon-optimized human and a native human S100A1 cDNA sequences (SEQ ID NOs: 8 and 5, respectively) is shown in FIG. 13.

For reference, certain non-limiting examples of animal-derived S100A1 cDNA sequences are described below. A nucleotide sequence alignment between a codon-optimized canine S100A1 cDNA sequence and a codon-optimized human S100A1 cDNA sequence (SEQ ID NOs: 21 and 8, respectively) is shown in FIG. 14.

S100A1 (*canis lupus familiaris*)
(NCBI Reference Sequence: XM_005622816.2)
(SEQ ID NO: 1)

ATGGGCTCTGAGCTGGAGACAGCGATGGAGACTCTCATCAATGTGTTCCA

TGCCCACTCGGGCAAGGAGGGAAACAAGTACAAGCTGAGCAAGAAGGAGC

TAAAGGAGCTGCTGCAGACTGAGCTCTCCGGCTTCCTGGACGCCCAGAAG

GATGCGGATGCTGTGGACAAGGTGATGAAAGAGCTAGATGAGAATGGAGA

TGGGGAGGTGGACTTCCAGGAGTATGTGGTGCTGGTGGCTGCCCTCACAG

TGGCCTGTAACAACTTCTTCTGGGAAAACAGTTGA

S100A1 (*felis catus*)
(NCBI Reference Sequence: XM_003999773.3)
(SEQ ID NO: 2)

ATGGGCTCAGAGCTGGAGACGGCGATGGAGACTCTCATCAACGTGTTCCA

CGCCCACTCGGGCAAGGAGGGAGACAAGTACAAGCTGAGCAAGAAGGAGC

TAAAAGAGCTGCTGCAGACCGAGCTCTCTGGCTTCCTGGACGCCCAGAAG

GATGCCGACGCTGTGGACAAGGTGATGAAAGAGCTAGACGAGAATGGAGA

TGGGGAGGTGGACTTCCAAGAGTATGTGGTGCTGGTGGCTGCCCTCACAG

TGGCCTGTAACAACTTTTTCTGGGAGAACAGTTGA

Aspects of the present disclosure provide compositions and methods that include the delivery of a transgene encoding an apoptotic inhibitor (e.g., an anti-apoptotic agent). Illustrative examples of apoptotic inhibitors include fink, p35, crmA, Bcl-2, Bcl-XL, Mcl-1, E1B-19K from adenovirus, as well as antagonists of pro-apoptotic agents (e.g., antisense, ribozymes, antibodies, etc.). In some embodiments, the apoptotic inhibitor is cardiac Apoptosis Repressor with Caspase Recruitment Domain (ARC), or a variant thereof. In other embodiments, the apoptotic inhibitor is cardiac ARC or a variant thereof. In some embodiments, it may be desirable to deliver an S100 family protein and the apoptotic inhibitor separately. In certain embodiments, a transgene encoding the S100 family protein is delivered concurrently or sequentially with one or more small molecule apoptotic inhibitors. Other exemplary small-molecule apoptotic inhibitors include c-Myc inhibitors, Bax inhibitors, p53 inhibitors, tBid inhibitors, caspase inhibitors, and inhibitors of pro-apoptotic BCL-2 family members.

The cARC is an apoptotic regulatory protein expressed almost exclusively in myogenic cells. It contains a caspase recruitment domain (CARD) through which it blocks the activation of some initiator caspases. ARC also blocks caspase-independent events associated with apoptosis. Apoptosis caused by acute ischemia and subsequent ventricular remodeling is implicated as a mediator of heart failure. Although post-ischemic heart failure may have multiple causes, recent attention has been directed toward understanding the contribution of apoptosis or programmed cell death. Apoptosis is characterized by preservation of mitochondrial and sarcolemmal membranes, nuclear chromatin condensation, and phagocytosis by macrophages or neighboring cells without triggering an inflammatory response. The activation of apoptosis is known to occur through mechanisms involving caspases, a family of cysteine proteases that are synthesized as inactive precursors and proteolytically cleaved into their active form. ARC is able the block the activation of apoptosis by blocking the caspases.

Accordingly, in some aspects, provided herein are rAAV vectors (or rAAV nucleic acid vectors) comprising a polynucleotide that comprises a sequence is at least 90%, at least 95%, or at least 99.5% identical to any one of the nucleotide sequences of SEQ ID NOs: 6-8, 16, and 21. In some embodiments, the polynucleotide sequence differs from the sequence of any one of SEQ ID NOs: 6-8, 16, and 21 by 1, 2, 3, 4, 5, 6, 7, 8, 9, 10, 11, 12, or more than 12 nucleotides. In particular embodiments, any of the disclosed rAAV vectors comprise a polynucleotide that comprises any of SEQ ID NOs: 6-8, 16, and 21.

In some embodiments, the disclosed cARC and S100 transgene sequences comprise truncations at the 5' or 3' end relative to the wild-type sequences. In some embodiments, the disclosed transgene sequences comprise truncations at the 5' or 3' end relative to SEQ ID NO: 5-8 and 15-21. In some embodiments, the transgene comprises a nucleotide sequence that differs from the sequence of any one of SEQ ID NOs: 5-8 and 15-21 by 1, 2, 3, 4, 5, 6, 7, 8, 9, 10, 11, 12, or more than 12 nucleotides.

In some embodiments, the cardiac ARC cDNA (or transgene) sequence of the polynucleotides of the disclosed rAAV vectors has 100% identity to a naturally-occurring human-derived cARC sequence. In other embodiments, the cARC cDNA sequence has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to a naturally-occurring human-derived cARC sequence.

In particular embodiments, the cARC cDNA sequence is codon-optimized for expression in human cells. In some embodiments, the cARC cDNA (transgene) sequence comprises a sequence having 100% identity to SEQ ID NO: 6 or SEQ ID NO: 7. In other embodiments, the cARC cDNA sequence has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 6 or SEQ ID NO: 7.

In other embodiments, the cARC cDNA sequence is codon-optimized for expression in canine cells. In some embodiments, the rAAV vector comprises a cARC cDNA sequence that has at least about 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 16. In some embodiments, the rAAV vector comprises SEQ ID NO: 16.

Non-limiting examples of cARC cDNA sequences are described below.

```
optimized ARC (homo sapiens)
                                         (SEQ ID NO: 6)
ATGGGCAACGCCCAGGAGCGGCCCAGCGAGACCATCGACCGGGAGCGGAA

GCGGCTGGTGGAGACCCTGCAGGCCGACAGCGGCCTGCTGCTGGACGCCC

TGCTGGCCCGGGGCGTGCTGACCGGCCCCGAGTACGAGGCCCTGGACGCC

CTGCCCGACGCCGAGCGGCGGGTGCGGCGGCTGCTGCTGCTGGTGCAGGG

CAAGGGCGAGGCCGCCTGCCAGGAGCTGCTGCGGTGCGCCCAGCGGACCG

CCGGCGCCCCCGACCCCGCCTGGGACTGGCAGCACGTGGGCCCCGGCTAC

CGGGACCGGAGCTACGACCCCCCCTGCCCCGGCCACTGGACCCCCGAGGC

CCCCGGCAGCGGCACCACCTGCCCCGGCCTGCCCCGGGCCAGCGACCCCG

ACGAGGCCGGCGGCCCCGAGGGCAGCGAGGCCGTGCAGAGCGGCACCCCC

GAGGAGCCCGAGCCCGAGCTGGAGGCCGAGGCCAGCAAGGAGGCCGAGCC

CGAGCCCGAGCCCGAGCCCGAGCTGGAGCCCGAGGCCGAGGCCGAGCCCG

AGCCCGAGCTGGAGCCCGAGCCCGACCCCGAGCCCGAGCCCGACTTCGAG

GAGCGGGACGAGAGCGAGGACAGCTGA

optimized ARC (homo sapiens)
                                         (SEQ ID NO: 7)
ATGGGGAATGCCCAAGAAAGGCCTTCTGAGACTATAGACCGCGAGCGCAA

GAGGCTTGTAGAAACCTTGCAGGCGGACTCTGGTCTCTTGCTGGACGCTC

TGCTTGCGCGGGGTGTTCTGACTGGACCGGAGTACGAAGCATTGGATGCC

CTTCCTGATGCAGAGAGACGAGTTAGACGCCTGTTGCTTCTTGTGCAAGG

CAAGGGTGAAGCCGCCTGTCAAGAGCTCCTGAGGTGTGCTCAACGAACCG

CCGGGGCGCCAGATCCGGCATGGGATTGGCAACATGTGGGGCCCGGCTAT

CGGGACCGGAGCTACGATCCACCATGCCCGGGTCATTGGACGCCGGAGGC

TCCAGGATCTGGTACAACATGCCCAGGACTCCCAAGAGCCAGTGACCCCG

ATGAAGCTGGAGGCCCCGAGGGCAGTGAAGCCGTACAGAGCGGTACCCCA

GAAGAACCAGAACCGGAGCTGGAGGCTGAAGCTAGTAAAGAGGCGGAACC

TGAACCCGAACCGGAGCCTGAGCTCGAGCCAGAGGCTGAGGCCGAGCCAG

AGCCTGAACTCGAACCCGAACCTGATCCAGAACCAGAGCCCGACTTCGAG

GAACGGGATGAGTCAGAGGATTCTTGA
```

Figure 12:
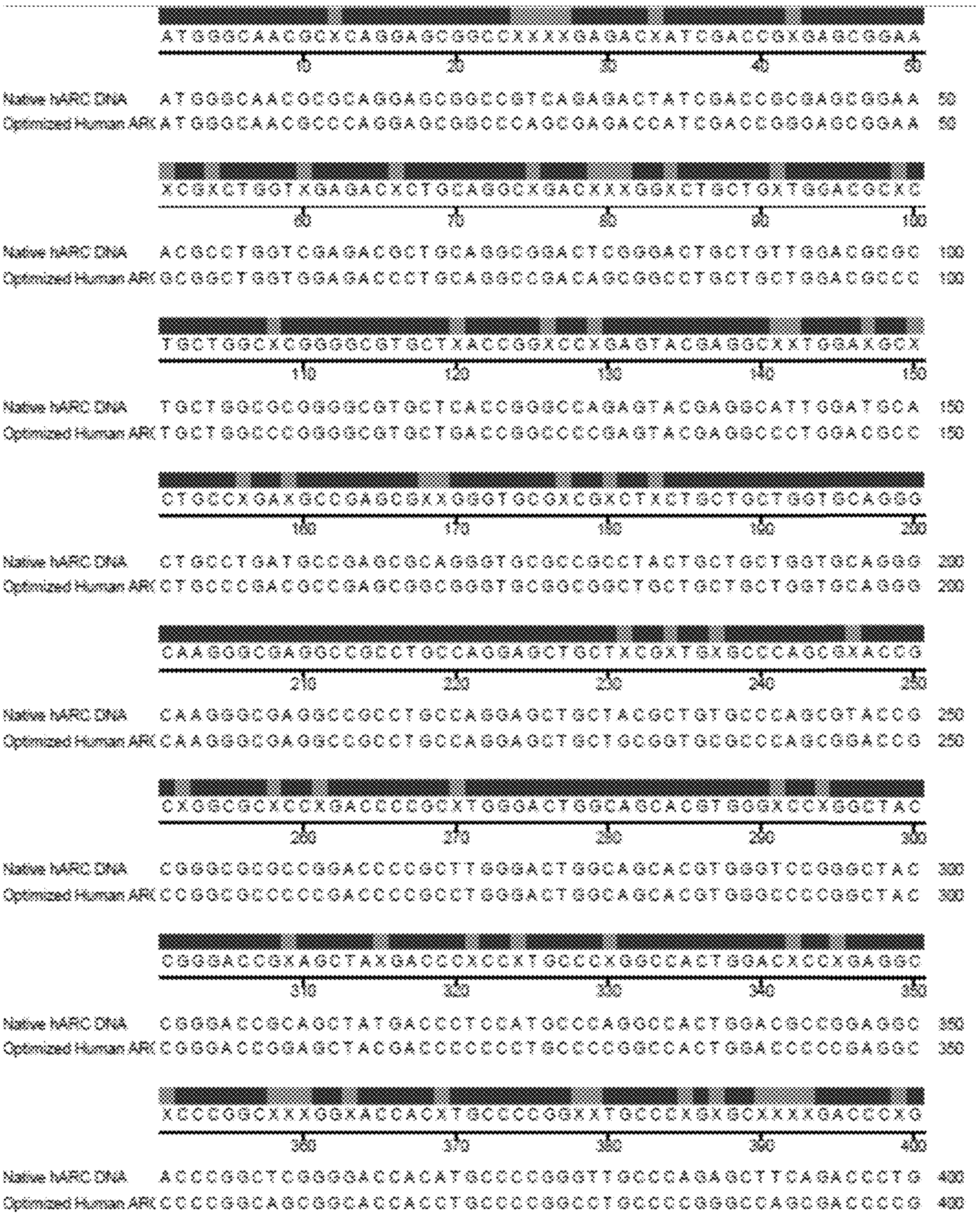
FIG. 12 illustrates a sequence alignment between codon-optimized and native human ARC cDNA sequences. Sequences correspond to SEQ ID NOs: 17, 18, and 6 from top to bottom.
Figure 12:
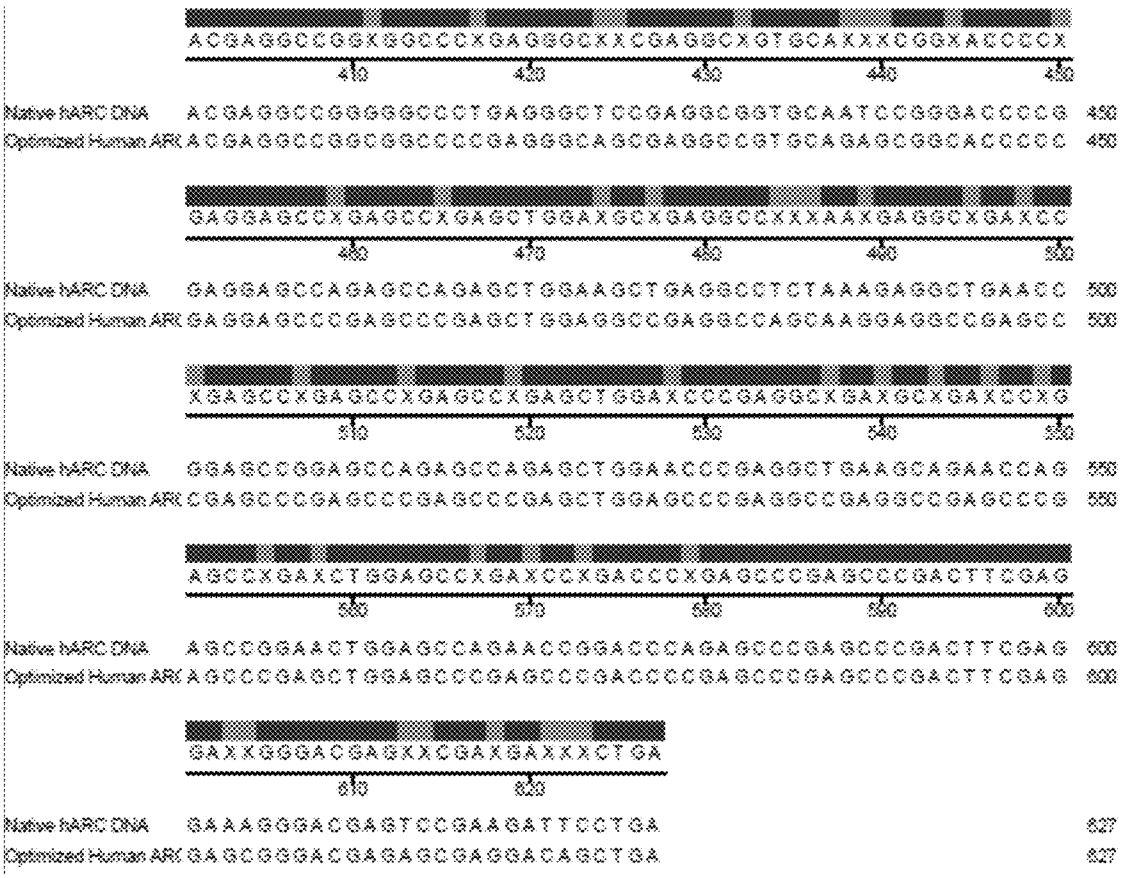

A nucleotide sequence alignment between a codon-optimized human and a native human ARC cDNA sequences (SEQ ID NOs: 6 and 18, respectively) is shown in FIG. 12.

Figure 11:
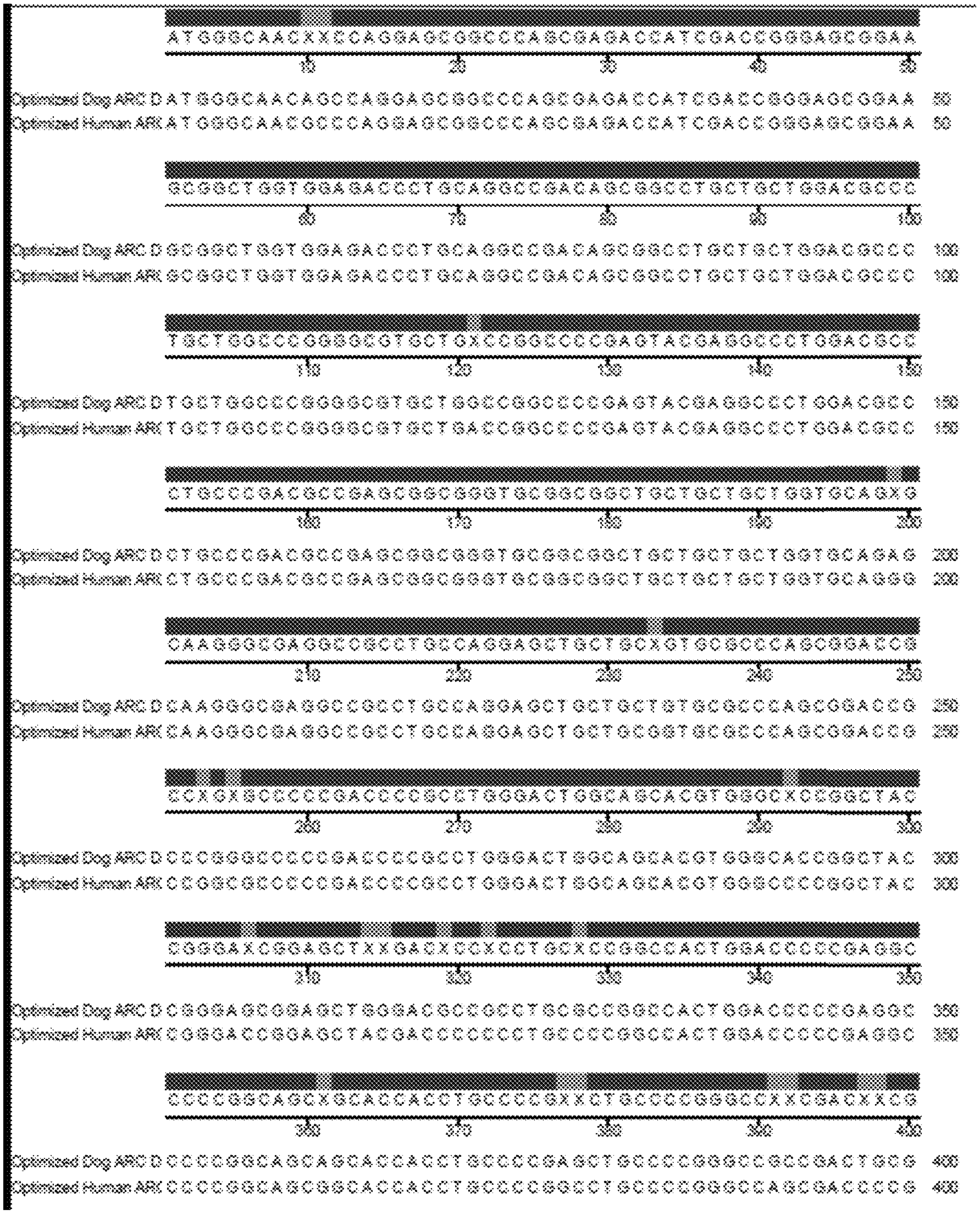
FIG. 11 illustrates a sequence alignment between codon-optimized canine ARC cDNA sequence and codon-optimized human ARC cDNA sequence. Sequences correspond to SEQ ID NOs: 15, 16, and 6 from top to bottom.
Figure 11:
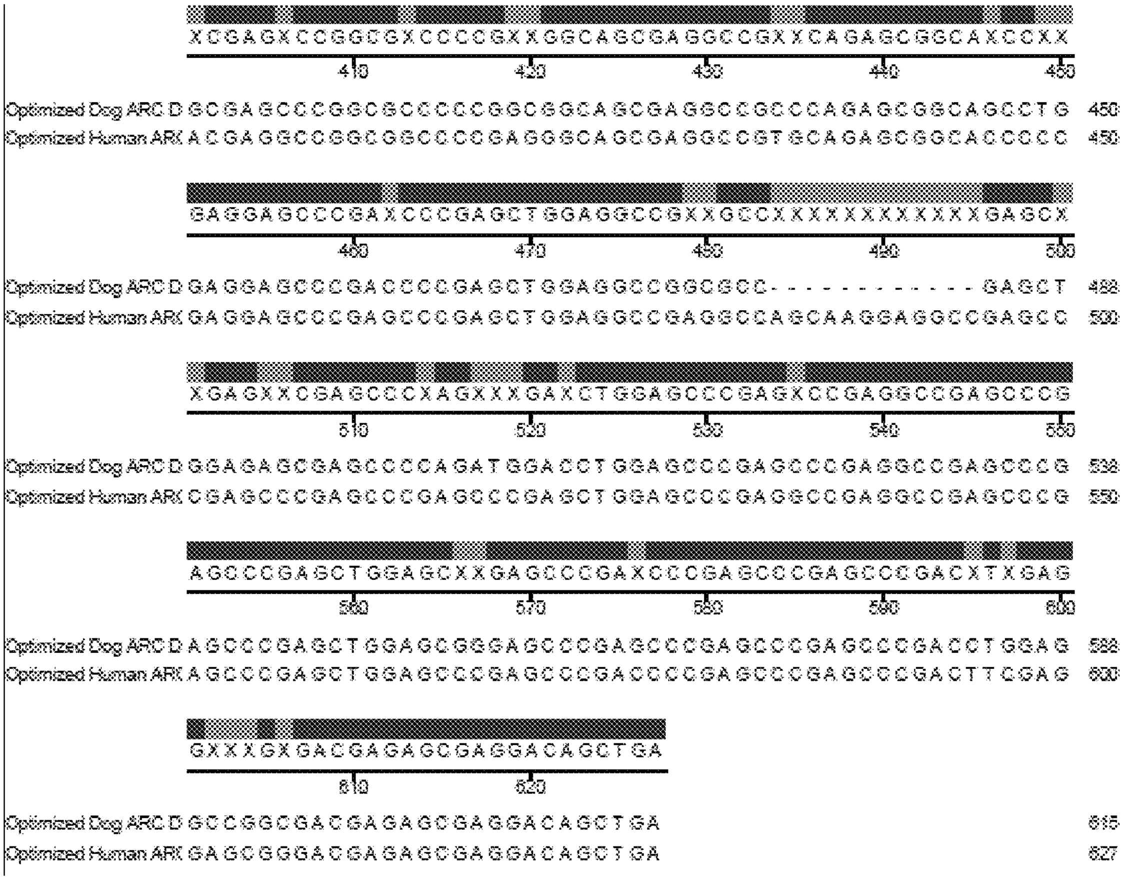

For reference, certain non-limiting examples of animal-derived ARC cDNA sequences are described below. A nucleotide sequence alignment between a codon-optimized canine ARC cDNA sequence and a codon-optimized human ARC cDNA sequence (SEQ ID NOs: 16 and 6, respectively) is shown in FIG. 11.

ARC (*canis lupus familiaris*)
(NCBI Reference Sequence: NM_001048121.1)
(SEQ ID NO: 3)

```
ATGCAGGAAGCGCCAGCCGCGCTGCCCACGGAGCCGGGCCCCAGCCCCGT

GCCTGCCTTCCTCGGCAAGCTGTGGGCGCTGGTGGGCGACCCGGGGACCG

ACCACCTCATCCGCTGGAGCCCGAGCGGGACCAGTTTCCTCGTCAGCGAC

CAGAGCCGCTTCGCCAAGGAAGTGCTGCCCCAGTACTTCAAGCACAGCAA

CATGGCGAGCTTCGTGCGGCAGCTCAACATGTACGGTTTTCGGAAGGTGG

TGAGCATCGAGCAGGGCGGCCTGCTCAGGCCGGAGCGCGACCACGTCGAG

TTCCAGCACCCGAGCTTCGTCCGCGGCCGAGAGCAACTCCTGGAGCGCGT

GCGGCGCAAGGTGCCCGCGCTGCGCAGCGACGACGGCCGCTGGCGCCCCG

AGGACCTGGGCCGGCTGCTGGGCGAGGTGCAGGCTTTGCGGGGAGTGCAG

GAGATCACCGAGGCGCGGCTGCGGGAGCTCAGGCAGCAGAACGAGATCTT

ATGGAGGGAGGTGGTGACTCTGCGGCAGAGCCACGGTCAGCAGCATCGCG

TCATTGGCAAGCTGATCCAGTGCCTCTTTGGGCCACTTCAGACAGGGTCC

AGCGGCGCAGGAGCTAAGAGAAAGCTGTCTCTGATGCTGGATGAGGGGAG

CTCATGCCCAACACCGGCCAAATTCAACACCTGTCCTTTACCTGGTGCCC

TCTTGCAGGATCCCTACTTTATCCAGTCGCCCCTCCCAGAGACCACCTTG

GGCCTCAGCAGCTCTCATAGGACCAGGGGCCCTATCATCTCTGACATCCA

TGAAGACTCTCCCTCCCCTGATGGGACCAGGCTTTCTCCTTCCAGTGGTG

GCAGGAGGGAGAAGGGCCTGGCACTGCTCAAAGAAGAGCCGGCCAGCCCA

GGGGGGGAAGGCGAGGCCGGGCTGGCCCTGGCCCCAAACGAGTGTGACTT

CTGCGTGACAGCCCCCCCCCACTGTCCGTGGCTGTGGTGCAGGCCATCC

TGGAAGGGAAGGGGAACTTCAGCCCCGAGGGGCCCAGGAATGCCCAACAG

CCTGAACCAAGGGGTCCCAGGGAGGTACCTGACAGGGGGACTCTGGGCCT

GGACAGGGGGGCACGAAGCCCAGAGAATCTGCTGCCTCCCATGCTGCTTC

GGGCCCCCCCTGAAAGTGTGGAGCCTGCAGGGCCCCTGGATGTGCTGGGC

CCCAGCCATCAAGGGCGAGAATGGACCCTGATGGACTTGGACATGGAGCT

GTCCCTGATGCAGCCCTTGGGTCCAGAGAGGAGTGAGACTGAGCTGGCGG

TCAAGGGGTTAAATTCTCCGGGGCCAGGGAAGGACTCCACACTTGGGGCA

CCACTCCTGCTCGATGTCCAAGCGGCTTTGGGAGGCCCAGCTCTCAGCCT

TCCTGGAGCTTTAACCATTTACAGCACCCCTGAGAGCCGAGCCAACTACC

TAGGCCCAGGGGCCAATCCCTCCCCCTGA
```

ARC (*felis catus*)
(NCBI Reference Sequence: XM_006941587.2)
(SEQ ID NO: 4)

```
ATGGGCAATGCGCAGGAGCGGCCCTCAGAGACGATCGATCGCGAGCGGAA

ACGCCTAGTGGAGACGCTGCAGGACGACTCCGGGCTGCTGCTGGATGCAC

TGCTGGCGCGCGGCGTGCTCACCGGGCCTGAGTATGAGGCGTTGGACGCG

CTGCCTGATGCCGAGCGCAGGGTGCGTCGCCTGCTGCTGCTGGTACAAAG

CAAGGGCGAGGCCGCCTGCCAGGAGCTGCTGCACTGCGCCCAGCGTACTA
```

-continued

```
CGCGCGCGCCAGACCCGGCCTGGGACTGGCAGCACGTGGGCACTGGCTAC

CGGGAACGCAGCTACGACTCTCCATGCCCTGGCCACTGGACGCCTGAGGC

ACCTGACTTGAGGACCGCTTGCCCCGAAACGCCCAGAGCTTCAGACTGCG

ACGAGGCTGGGGTTTCAGGGGGCTCGGAGGCAGTATCCGGAACCCTCGAG

GAACTCGATCCGGAAGTGGAAGCTGAAGTCTCTGAAGGGGCTGAGCCAGA

GCCAGAGCCAGAGCCCGACTTTGAGGCGGGTGATGAGTCTGAAGATTCC
```

In other aspects, the two or more transgenes of any of the disclosed rAAV vectors comprise a transgene comprising a dominant negative form of Phospholamban (or dn-PLN). Phospholamban (PLN) is an endogenous inhibitor of the sarco/endoplasmic reticulum $Ca^{2+}$ ATPase 2a (SERCA2a) pump, which mediates calcium ion reuptake into the sarcoplasmic reticulum (SR) of cardiomyocytes. The dominant negative form is a pseudophosphorylated form that competes for binding SERCA2a with native phospholamban, and thereby reduces its inhibitory effect on SERCA2a (see Bish, et al. *Hum Gene Ther.* 2011; 22(8): 969-977, herein incorporated by reference). Accordingly, in some embodiments, the second transgene of the disclosed rAAV vectors comprises dn-PLN. In some embodiments, the disclosed rAAV vectors may comprise any of the disclosed S100A1 transgenes (e.g., a human codon-optimized S100A1 sequence) and a dn-PLN transgene. In some embodiments, the disclosed rAAV vectors may encode, and thereby deliver into a cell, a S100A1 protein and a dn-PLN protein.

In further aspects, any of the disclosed rAAV vectors may comprise three or more transgenes. In some embodiments, the rAAV vectors encode three transgenes. In some embodiments, the third transgene is a dn-PLN sequence. Said three transgenes may comprise a first transgene encoding S100A1 (e.g., a human codon-optimized S100A1 sequence), a second transgene encoding cARC (e.g., a human codon-optimized cARC sequence), and a third transgene encoding dn-PLN.

In some embodiments, the disclosed rAAV vectors do not encode a protein derived from a canine or feline. In some embodiments, any of the disclosed vectors does not comprise a native canine or feline S100A1-encoding or ARC-encoding nucleotide sequence. In some embodiments, the disclosed rAAV vectors do not comprise SEQ ID NO: 1 or 2. In some embodiments, the disclosed rAAV vectors do not comprise SEQ ID NO: 3 or 4, or any of SEQ ID NOs: 1-4.

Recombinant AAV (rAAV) Vectors

Aspects of the present disclosure relate to recombinant AAV vectors that may be used for gene therapy for heart diseases. As used herein, the term "vector" may refer to a nucleic acid vector (e.g., a plasmid or recombinant viral genome), a wild-type AAV genome, or a virus that comprises a viral genome. In some embodiments, the term "vector" may refer to a viral particle, such as an AAV viral particle.

The wild-type AAV genome is a single-stranded deoxyribonucleic acid (ssDNA), either positive- or negative-sensed. The genome comprises two inverted terminal repeats (ITRs), one at each end of the DNA strand, and two open reading frames (ORFs): rep and cap between the ITRs. The rep ORF comprises four overlapping genes encoding Rep proteins required for the AAV life cycle. The cap ORF comprises overlapping genes encoding capsid proteins: VP1, VP2 and VP3, which interact together to form the viral capsid. VP1, VP2 and VP3 are translated from one mRNA transcript, which can be spliced in two different manners.

Either a longer or shorter intron can be excised resulting in the formation of two isoforms of mRNAs: a ~2.3 kb- and a ~2.6 kb-long mRNA isoform. The capsid forms a supramolecular assembly of approximately 60 individual capsid protein subunits into a non-enveloped, T-1 icosahedral lattice capable of protecting the AAV genome. A mature AAV capsid is composed of VP1, VP2, and VP3 (molecular masses of approximately 87, 73, and 62 kDa respectively) in a ratio of about 1:1:10.

Recombinant AAV (rAAV) particles may comprise a recombinant nucleic acid vector (hereafter referred to as "rAAV vector"), which may comprise at a minimum: (a) one or more heterologous nucleic acid regions comprising a sequence encoding a transgene; and (b) one or more regions comprising sequences that facilitate the integration of the heterologous nucleic acid region (optionally with the one or more nucleic acid regions comprising a sequence that facilitates expression) into the genome of the subject. In some embodiments, the sequences facilitating the integration of the heterologous nucleic acid region (optionally with the one or more nucleic acid regions comprising a sequence that facilitates expression) into the genome of the subject are inverted terminal repeat (ITR) sequences (e.g., wild-type ITR sequences or engineered ITR sequences) flanking the one or more nucleic acid regions (e.g., heterologous nucleic acid regions).

In some embodiments, the rAAV nucleic acid vector comprises one or more transgenes comprising a sequence encoding a protein or polypeptide of interest operably linked to a promoter, wherein the one or more transgenes are flanked on each side with an ITR sequence. In some embodiments, the nucleic acid vector further comprises a region encoding a Rep protein as described herein, either contained within the region flanked by ITRs or outside the region or nucleic acid) operably linked to a promoter. The ITR sequences may be derived from any AAV serotype (e.g., 1, 2, 3, 4, 5, 6, 7, 8, 9, or 10) or may be derived from more than one serotype. In some embodiments, the ITR sequences are derived from AAV2 or AAV6 serotypes. In some embodiments, a first serotype provided herein is not an AAV2 or AAV8 serotype. In some embodiments, the ITR sequences of the first serotype are derived from AAV3, AAV5 or AAV6. In some embodiments, the ITR sequences are derived from AAV2, AAV3, AAV5 or AAV6. In some embodiments, the ITR sequences are the same serotype as the capsid (e.g., AAV6 ITR sequences and AAV6 capsid, etc.). In some embodiments, the ITR sequences are derived from AAVrh.10 serotype.

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, et al. *Proc Natl Acad Sci USA.* 1996 Nov. 26; 93(24): 14082-7; and Curtis A. Machida. Methods in Molecular Medicine™. Viral Vectors for *Gene Therapy Methods and Protocols.* 10.1385/1-59259-304-6:201© Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). In some embodiments, the rAAV comprises a pTR-UF-11 plasmid backbone, which is a plasmid that contains AAV2 ITRs. This plasmid is commercially available from the American Type Culture Collection (ATCC MBA-331).

In some embodiments, the rAAV vectors of the present disclosure comprise both the cS100A1 transgene and the cARC transgene, for their concurrent delivery and expression in a subject. The transgene encoding the S100 family protein (e.g., a cS100A1) may be positioned 5' to the transgene encoding the apoptotic inhibitor (e.g., a cARC) within the herein-described rAAV nucleic acid vectors. Alternatively, the transgene encoding the apoptotic inhibitor may be positioned 5' to the transgene encoding the S100 family protein within the described rAAV nucleic acid vectors.

Thus, in some embodiments, the rAAV vector comprises one or more regions comprising a sequence that facilitates expression of the transgene (e.g., the heterologous nucleic acid), e.g., expression control sequences operably linked to the nucleic acid. Numerous such sequences are known in the art. Non-limiting examples of expression control sequences include promoters, insulators, silencers, response elements, introns, enhancers, initiation sites, internal ribosome entry sites (IRES) termination signals, and poly(A) signals. Any combination of such control sequences is contemplated herein (e.g., a promoter and a poly(A) signal). In some embodiments, the rAAV vectors comprise a promoter that is operably linked to the coding sequence of the transgenes and facilitates expression of the transgenes.

A "promoter", as used herein, refers to a control region of a nucleic acid at which initiation and rate of transcription of the remainder of a nucleic acid sequence are controlled. A promoter drives transcription of the nucleic acid sequence that it regulates, thus, it is typically located at or near the transcriptional start site of a gene. A promoter may have, for example, a length of 100 to 1000 nucleotides. In some embodiments, a promoter is operably linked to a nucleic acid, or a sequence of a nucleic acid (nucleotide sequence). A promoter is considered to be "operably linked" to a sequence of nucleic acid that it regulates when the promoter is in a correct functional location and orientation relative to the sequence such that the promoter regulates (e.g., to control ("drive") transcriptional initiation and/or expression of) that sequence.

Promoters that may be used in accordance with the present disclosure may comprise any promoter that can drive the expression of the transgenes in the heart of the subject. In some embodiments, the promoter may be a tissue-specific promoter. A "tissue-specific promoter", as used herein, refers to promoters that can only function in a specific type of tissue, e.g., the heart. Thus, a "tissue-specific promoter" is not able to drive the expression of the transgenes in other types of tissues. In some embodiments, the promoter that may be used in accordance with the present disclosure is a cardiac-restricted promoter. For example, promoter is a cardiac-restricted promoter selected from cardiac troponin C, cardiac troponin I, and cardiac troponin T (cTnT).

Alternatively, the promoter may be, without limitation, a promoter from one of the following genes: α-myosin heavy chain gene, 6-myosin heavy chain gene, myosin light chain 2v (MLC-2v) gene, myosin light chain 2a gene, CARP gene, cardiac a-actin gene, cardiac m2 muscarinic acetylcholine gene, ANF, cardiac troponin C, cardiac troponin I, cardiac troponin T(cTnT), cardiac sarcoplasmic reticulum Ca-ATPase gene, skeletal α-actin; or an artificial cardiac promoter derived from MLC-2v gene.

In some embodiments of the disclosed rAAV vectors, the two or more transgenes are operably controlled by a single promoter. In other embodiments, each of the two or more transgenes are operably controlled by a distinct promoter.

In some embodiments, the rAAV vectors of the present disclosure further comprise an Internal Ribosome Entry Site (IRES). An IRES is a nucleotide sequence that allows for translation initiation in the middle of a messenger RNA (mRNA) sequence as part of the greater process of protein synthesis. Usually, in eukaryotes, translation can be initiated only at the 5' end of the mRNA molecule, since 5' cap recognition is required for the assembly of the initiation complex. In some embodiments, the IRES is located between the transgenes. In such embodiments, the proteins encoded by different transgenes are translated individually (i.e., versus translated as a fusion protein).

In some embodiments, the rAAV vectors of the present disclosure further comprise a polyadenylation (pA) signal. Eukaryotic mRNAs are typically transcribed as a precursor mRNA. The precursor mRNA is processed to generate the mature mRNA, including a polyadenylation process. The process of polyadenylation begins as the transcription of a gene terminates. The 3'-most segment of the newly made precursor mRNA is first cleaved off by a set of proteins. These proteins then synthesize the poly(A) tail at the RNA's 3' end. The cleavage site typically contains the polyadenylation signal, e.g., AAUAAA. The poly(A) tail is important for the nuclear export, translation, and stability of mRNA.

In some embodiments, the rAAV vectors of the present disclosure comprise at least, in order from 5' to 3', a first adeno-associated virus (AAV) inverted terminal repeat (ITR) sequence, a promoter operably linked to a first transgene, an IRES operably linked to a second transgene, a polyadenylation signal, and a second AAV inverted terminal repeat (ITR) sequence.

In some embodiments, the rAAV is circular. In some embodiments, the rAAV vector is linear. In some embodiments, the rAAV vector is single-stranded. In some embodiments, the rAAV vector is double-stranded. In some embodiments, the rAAV vector is a self-complementary rAAV vector. Any rAAV vector described herein may be encapsidated by a viral capsid, such as an AAV6 capsid or any other serotype (e.g., a serotype that is of the same serotype as the ITR sequences).

Described below are exemplary rAAV vectors of the present disclosure. The vectors illustrated below comprise the linearized plasmid sequences set forth as SEQ ID NOs: 9-12. The vectors of the disclosure may comprise nucleotide sequences that have at least 70% identity, at least about 80% identity, at least about 90% identity, at least about 95% identity, at least about 96% identity, at least about 97% identity, at least about 98% identity, at least about 99% identity, at least about 99.5% identity, or at least about 99.9% identity to the sequences set forth as SEQ ID NOs: 9-12. These sequences are annotated in the keys that follow.

In some embodiments, any of the disclosed rAAV nucleic acid vector sequences comprise truncations at the 5' or 3' end relative to the sequences of any one of SEQ ID NOs: 9-12. In some embodiments, any of the rAAV vectors comprise a nucleotide sequence that differs from the sequence of any one of SEQ ID NOs: 9-12 by 1, 2, 3, 4, 5, 6, 7, 8, 9, 10, 11, 12, 13, 14, 15, 16, 17, 18, or more than 18 nucleotides.

pAAVsc.cTnT.Opt.hARC_Opt.hS100A1

(SEQ ID NO: 9)

*ctgcgcgctcgctcgctcactgaggccgcccgggcaaagcccgggcgtcgggcgacctttggtcgcccggcctcagtgagcgag*

*cgagcgcgcagagagggagtg*tagccatgctctaggaagatcaattcaattcacgcgtggaattcgcccttaacgggccccccctc gaggtcgggataaaagcagtctgggctttcacatgacagcatctggggctgcggcagagggtcgggtccgaagcgctgccttatcag cgtccccagccctgggaggtgacagctggctggcttgtgtcagcccctcgggcactcacgtatctccgtccgacgggtttaaaatagc aaaactctgaggccacacaatagcttgggcttatatgggctcctgtgggggaagggggagcacggagggggccggggccgctgct gccaaaatagcagctcacaagtgttgcattcctctctgggcgccgggcacattcctgctggctctgcccgccccggggtgggcgccg gggggaccttaaagcctctgcccccccaaggagcccttcccagacagccgccggcacccaccgctccgtgggacgatccccgaagc tctagaggatccagccttaaggctagagtacttaatacgactcactataggctagcgccacc*ATGGGGAATGCCCAAGA*

*GCGGACTCTGGTCTCTTGCTGGACGCTCTGCTTGCGCGGGGTGTTCTGACTGGACC*

*GGAGTACGAAGCATTGGATGCCCTTCCTGATGCAGAGAGACGAGTTAGACGCCTG*

*TTGCTTCTTGTGCAAGGCAAGGGTGAAGCCGCCTGTCAAGAGCTCCTGAGGTGTG*

*CTCAACGAACCGCCGGGGCGCCAGATCCGGCATGGGATTGGCAACATGTGGGGCC*

*CGGCTATCGGGACCGGAGCTACGATCCACCATGCCCGGGTCATTGGACGCCGGAG*

*GCTCCAGGATCTGGTACAACATGCCCAGGACTCCCAAGAGCCAGTGACCCCGATG*

*AAGCTGGAGGCCCCGAGGGCAGTGAAGCCGTACAGAGCGGTACCCCAGAAGAACC*

-continued

*AGAACCGGAGCTGGAGGCTGAAGCTAGTAAAGAGGCGGAACCTGAACCCGAACCG*

*GAGCCTGAGCTCGAGCCAGAGGCTGAGGCCGAGCCAGAGCCTGAACTCGAACCCG*

*AACCTGATCCAGAACCAGAGCCCGACTTCGAGGAACGGGATGAGTCAGAGGATTC*

*TTGA*actagtgcgtaccaggtcccctctccctcccccccccctaacgttactggccgaagccgcttggaataaggccggtgtgcgtt tgctatatgttattttccaccatattgccgtcttttggcaatgtgagggcccggaaacctggccctgtcttcttgacgagcattcctagggg tctttcccctctcgccaaaggaatgcaaggtctgttgaatgtcgtgaaggaagcagttcctctggaagcttcttgaagacaaacaacgtct gtagcgaccctttgcaggcagcggaaccccccacctggcgacaggtgcctctgcggccaaaagccacgtgtataagatacacctgc aaaggcggcacaaccccagtgccacgttgtgagttggatagttgtggaaagagtcaaatggctctcctcaagcgtattcaacaagggg ctgaaggatgcccagaaggtaccccattgtatgggatctgatctggggcctcggtgcacatgctttacatgtgtttagtcgaggttaaaa aacgtctaggccccccgaaccacggggacgtggttttcctttgaaaaacacgatgataagcttgccacaaccttgggccaccATG

GGCAGCGAGCTGGAGACCGCCATGGAGACCCTGATCAACGTNTTCCACGCC

CACAGCGGCAAGGAGGGCGACAAGTACAAGCTGAGCAAGAAGGAGCTGAA

GGAGCTGCTGCAGACCGAGCTGAGCGGCTTCCTGGACGCCCAGAAGGACGT

NGACGCCGTNGACAAGGTNATGAAGGAGCTGGACGAGAACGGCGACGGCG

AGGTNGACTTCCAGGAGTACGTNGTNCTGGTNGCCGCCCTGACCGTNGCCT

GCAACAACTTCTTCTGGGAGAACAGCTGAgcggccgcatcgataccgtcgactagagctcgctgatc agcctcgactgtgccttctagttgccagccatctgttgtttgcccctcccccgtgccttccttgaccctggaaggtgccactcccactgtcc tttcctaataaaatgaggaaattgcatcgcattgtctgagtaggtgtcattctattctggggggtggggtggggcaggacagcaagggg gaggattgggaagacaatagcaggcgataaggatcttcctagagcatggctacgtagataagtagcatggcgggttaatcattaacta caaggaacccctagtgatggagttggccactccctctctgcgcgctcgctcgctcactgaggccgggcgaccaaaggtcgcccgac gcccgggctttgcccgggcggcctcagtgagcgagcgagcgcgcag Key:
ITR
cTnT Promoter
*hARC_Opt*

IRES hS100A1_Opt
BGH PolyA Signal pAAVsc.cTnT.Opt.hS100A1_Opt.hARC (SEQ ID NO: 10)

*ctgcgcgctcgctcgctcactgaggccgcccgggcaaagcccgggcgtcgggcgacctttggtcgcccggcctcagtgagcgag*

*cgagcgcgcagagagggagtg*tagccatgctctaggaagatcaattcaattcacgcgtggaattcgcccttaacgggcccccctc gaggtcgggataaaagcagtctgggctttcacatgacagcatctggggctgcggcagagggtcgggtccgaagcgctgccttatcag cgtccccagccctgggaggtgacagctggctggcttgtgtcagcccctcgggcactcacgtatctccgtccgacgggtttaaaatagc aaaactctgaggccacacaatagcttgggcttatatgggctcctgtgggggaagggggagcacggagggggccggggccgctgct gccaaaatagcagctcacaagtgttgcattcctctctgggcgccgggcacattcctgctggctctgcccgccccggggtgggcgccg gggggaccttaaagcctctgccccccaaggagcccttcccagacagccgccggcacccaccgctccgtgggacgatccccgaagc -continued tctagaggatccagccttaaggctagagtacttaatacgactcactataggctagcgccaccATGGGCAGCGAGCTG

GAGACCGCCATGGAGACCCTGATCAACGTNTTCCACGCCCACAGCGGCAAG

GAGGGCGACAAGTACAAGCTGAGCAAGAAGGAGCTGAAGGAGCTGCTGCA

GACCGAGCTGAGCGGCTTCCTGGACGCCCAGAAGGACGTNGACGCCGTNGA

CAAGGTNATGAAGGAGCTGGACGAGAACGGCGACGGCGAGGTNGACTTCCA

GGAGTACGTNGTNCTGGTNGCCGCCCTGACCGTNGCCTGCAACAACTTCTT

CTGGGAGAACAGCTGAactagtgcgtaccaggtcccctctccctcccccccccctaacgttactggccgaagccgct tggaataaggccggtgtgcgtttgtctatatgttattttccaccatattgccgtcttttggcaatgtgagggcccggaaacctggccctgtct tcttgacgagcattcctaggggtctttcccctctcgccaaaggaatgcaaggtctgttgaatgtcgtgaaggaagcagttcctctggaag cttcttgaagacaaacaacgtctgtagcgaccctttgcaggcagcggaaccccccacctggcgacaggtgcctctgcggccaaaagc cacgtgtataagatacacctgcaaaggcggcacaaccccagtgccacgttgtgagttggatagttgtggaaagagtcaaatggctctc ctcaagcgtattcaacaaggggctgaaggatgcccagaaggtaccccattgtatgggatctgatctggggcctcggtgcacatgcttta catgtgtttagtcgaggttaaaaaacgtctaggccccccgaaccacggggacgtggttttcctttgaaaaacacgatgataagcttgcca caaccttgggccacc

*ATGGGGAATGCCCAAGAAAGGCCTTCTGAGACTATAGACCGCGAGCGCAAGAGGC*

*TTGTAGAAACCTTGCAGGCGGACTCTGGTCTCTTGCTGGACGCTCTGCTTGCGCGG*

*GGTGTTCTGACTGGACCGGAGTACGAAGCATTGGATGCCCTTCCTGATGCAGAGA*

*GACGAGTTAGACGCCTGTTGCTTCTTGTGCAAGGCAAGGGTGAAGCCGCCTGTCA*

*AGAGCTCCTGAGGTGTGCTCAACGAACCGCCGGGGCGCCAGATCCGGCATGGGAT*

*TGGCAACATGTGGGGCCCGGCTATCGGGACCGGAGCTACGATCCACCATGCCCGG*

*GTCATTGGACGCCGGAGGCTCCAGGATCTGGTACAACATGCCCAGGACTCCCAAG*

*AGCCAGTGACCCCGATGAAGCTGGAGGCCCCGAGGGCAGTGAAGCCGTACAGAGC*

*GGTACCCCAGAAGAACCAGAACCGGAGCTGGAGGCTGAAGCTAGTAAAGAGGCGG*

*AACCTGAACCCGAACCGGAGCCTGAGCTCGAGCCAGAGGCTGAGGCCGAGCCAGA*

*GCCTGAACTCGAACCCGAACCTGATCCAGAACCAGAGCCCGACTTCGAGGAACGG*

*GATGAGTCAGAGGATTCTTGA*gcggccgcatcgataccgtcgactagagctcgctgatcagcctcgactgtgcctt ctagttgccagccatctgttgtttgcccctcccccgtgccttccttgaccctggaaggtgccactcccactgtcctttcctaataaaatgag gaaattgcatcgcattgtctgagtaggtgtcattctattctggggggtggggtggggcaggacagcaagggggaggattgggaagac aatagcaggcgataaggatcttcctagagcatggctacgtagataagtagcatggcgggttaatcattaactacaaggaacccctagtg -continued atggagttggccactccctactgcgcgctcgctcgctcactgaggccgggcgaccaaaggtcgcccgacgcccgggattgcccg ggcggcctcagtgagcgagcgagcgcgcag Key:
ITR
cTnT Promoter
hS100A1_Opt
IRES

*hARC_Opt*

BGH Poly A Signal pAAVsc.cTnT.hS100A1.hARC_opt (SEQ ID NO: 11)

*ctgcgcgctcgctcgctcactgaggccgcccgggcaaagcccgggcgtcgggcgacctttggtcgcccggcctcagtgagcgag*

*cgagcgcgcagagagggagtg*tagccatgctctaggaagatcaattcaattcacgcgtggaattcgcccttaacgggcccccctc gaggtcgggataaaagcagtctgggctttcacatgacagcatctggggctgcggcagagggtcgggtccgaagcgctgccttatcag cgtccccagccctgggaggtgacagctggctggcttgtgtcagcccctcgggcactcacgtatctccgtccgacgggtttaaaatagc aaaactctgaggccacacaatagcttgggcttatatgggctcctgtgggggaagggggagcacggagggggccggggccgctgct gccaaaatagcagctcacaagtgttgcattcctctctgggcgccgggcacattcctgctggctctgcccgccccggggtgggcgccg gggggaccttaaagcctctgcccccaaggagcccttcccagacagccgccggcacccaccgctccgtgggacgatccccgaagc tctagaggatccagccttaaggctagagtacttaatacgactcactataggctagcgccaccatgggctctgagctggagacggcga tggagaccctcatcaacgtgttccacgcccactcgggcaaagagggggacaagtacaagctgagcaagaaggagctgaaa gagctgctgcagacggagctctctggcttcctggatgcccagaaggatgtggatgctgtggacaaggtgatgaaggagctag acgagaatggagacggggaggtggacttccaggagtatgtggtgcttgtggctgctctcacagtggcctgtaacaatttcttct gggagaacagttgaactagtgcgtaccaggtcccctctccctcccccccccctaacgttactggccgaagccgcttggaataaggcc ggtgtgcgtttgtctatatgttattttccaccatattgccgtcttttggcaatgtgagggcccggaaacctggccctgtcttcttgacgagcat tcctaggggtctttcccctctcgccaaaggaatgcaagtctgttgaatgtcgtgaaggaagcagttcctctggaagcttcttgaagaca aacaacgtctgtagcgaccctttgcaggcagcggaaccccccacctggcgacaggtgcctctgcggccaaaagccacgtgtataag atacacctgcaaaggcggcacaaccccagtgccacgttgtgagttggatagttgtggaaagagtcaaatggctctcctcaagcgtattc aacaaggggctgaaggatgcccagaaggtaccccattgtatgggatctgatcggggcctcggtgcacatgctttacatgtgtttagtc gaggttaaaaaacgtctaggccccccgaaccacggggacgtggttttcctttgaaaaacacgatgataagcttgccacaaccttgggc cacc*ATGGGGAATGCCCAAGAAAGGCCTTCTGAGACTATAGACCGCGAGCGCAAGA*

*GGCTTGTAGAAACCTTGCAGGCGGACTCTGGTCTCTTGCTGGACGCTCTGCTTGCG*

*CGGGGTGTTCTGACTGGACCGGAGTACGAAGCATTGGATGCCCTTCCTGATGCAG*

*AGAGACGAGTTAGACGCCTGTTGCTTCTTGTGCAAGGCAAGGGTGAAGCCGCCTG*

*TCAAGAGCTCCTGAGGTGTGCTCAACGAACCGCCGGGGCGCCAGATCCGGCATGG*

*GATTGGCAACATGTGGGGCCCGGCTATCGGGACCGGAGCTACGATCCACCATGCC*

*CGGGTCATTGGACGCCGGAGGCTCCAGGATCTGGTACAACATGCCCAGGACTCCC*

-continued

*AAGAGCCAGTGACCCCGATGAAGCTGGAGGCCCCGAGGGCAGTGAAGCCGTACAG*

*AGCGGTACCCCAGAAGAACCAGAACCGGAGCTGGAGGCTGAAGCTAGTAAAGAGG*

*CGGAACCTGAACCCGAACCGGAGCCTGAGCTCGAGCCAGAGGCTGAGGCCGAGCC*

*AGAGCCTGAACTCGAACCCGAACCTGATCCAGAACCAGAGCCCGACTTCGAGGAA*

*CGGGATGAGTCAGAGGATTCTTGA*gcggccgcatcgataccgtcgactagagctcgctgatcagcctcgactgt gccttctagttgccagccatctgttgtttgcccctcccccgtgccttccttgaccctggaaggtgccactcccactgtcctttcctaataaaa tgaggaaattgcatcgcattgtctgagtaggtgtcattctattctggggggtggggtggggcaggacagcaagggggaggattggga agacaaagcaggcgataaggatcttcctagagcatggctacgtagataagtagcatggcgggttaatcattaactacaaggaacccct agtgatggagttggccactccctctctgcgcgctcgctcgctcactgaggccgggcgaccaaaggtcgcccgacgcccgggctttgc ccgggcggcctcagtgagcgagcgagcgcgcag Key:
ITR
cTnT Promoter
hS100A1
IRES

*hARC_Opt*

BGH PolyA Signal pAAVsc.cTnT.hARC_Opt.hS100A1

(SEQ ID NO: 12)

*ctgcgcgctcgctcgctcactgaggccgcccgggcaaagcccgggcgtcgggcgacctttggtcgcccggcctcagtgagcgag*

*cgagcgcgcagagagggagtg*tagccatgctctaggaagatcaattcaattcacgcgtggaattcgcccttaacgggccccccctc gaggtcgggataaaagcagtctgggctttcacatgacagcatctggggctgcggcagagggtcgggtccgaagcgctgccttatcag cgtccccagccctgggaggtgacagctggctggcttgtgtcagcccctcgggcactcacgtatctccgtccgacgggtttaaaatagc aaaactctgaggccacacaatagcttgggcttatatgggctcctgtgggggaagggggagcacggagggggccggggccgctgct gccaaaatagcagctcacaagtgttgcattcctctctgggcgccgggcacattcctgctggctctgcccgccccggggtgggcgccg gggggaccttaaagcctctgcccccccaaggagcccttcccagacagccgccggcacccaccgctccgtgggacgatccccgaagc tctagaggatccagccttaaggctagagtacttaatacgactcactataggctagcgccacc*ATGGGGAATGCCCAAGA*

*AAGGCCTTCTGAGACTATAGACCGCGAGCGCAAGAGGCTTGTAGAAACCTTGCAG*

*GCGGACTCTGGTCTCTTGCTGGACGCTCTGCTTGCGCGGGGTGTTCTGACTGGACC*

*GGAGTACGAAGCATTGGATGCCCTTCCTGATGCAGAGAGACGAGTTAGACGCCTG*

*TTGCTTCTTGTGCAAGGCAAGGGTGAAGCCGCCTGTCAAGAGCTCCTGAGGTGTG*

*CTCAACGAACCGCCGGGGCGCCAGATCCGGCATGGGATTGGCAACATGTGGGGCC*

*CGGCTATCGGGACCGGAGCTACGATCCACCATGCCCGGGTCATTGGACGCCGGAG*

*GCTCCAGGATCTGGTACAACATGCCCAGGACTCCCAAGAGCCAGTGACCCCGATG*

*AAGCTGGAGGCCCCGAGGGCAGTGAAGCCGTACAGAGCGGTACCCCAGAAGAACC*

-continued

*AGAACCGGAGCTGGAGGCTGAAGCTAGTAAAGAGGCGGAACCTGAACCCGAACCG*

*GAGCCTGAGCTCGAGCCAGAGGCTGAGGCCGAGCCAGAGCCTGAACTCGAACCCG*

*AACCTGATCCAGAACCAGAGCCCGACTTCGAGGAACGGGATGAGTCAGAGGATTC*

*TTGA*actagtgcgtaccaggtcccctctccctcccccccccctaacgttactggccgaagccgcttggaataaggccggtgtgcgtt tgtctatatgttattttccaccatattgccgtcttttggcaatgtgagggcccggaaacctggccctgtcttcttgacgagcattcctagggg tctttcccctctcgccaaaggaatgcaaggtctgttgaatgtcgtgaaggaagcagttcctctggaagcttcttgaagacaaacaacgtct gtagcgaccctttgcaggcagcggaaccccccacctggcgacaggtgcctcgcggccaaaagccacgtgtataagatacacctgc aaaggcggcacaaccccagtgccacgttgtgagttggatagttgtggaaagagtcaaatggctctcctcaagcgtattcaacaagggg ctgaaggatgcccagaaggtaccccattgtatgggatctgatctggggcctcggtgcacatgctttacatgtgtttagtcgaggttaaaa aacgtctaggccccccgaaccacggggacgtggttttcctttgaaaaacacgatgataagcttgccacaaccttgggccaccatgggc tctgagctggagacggcgatggagaccctcatcaacgtgttccacgcccactcgggcaaagagggggacaagtacaagctg agcaagaaggagctgaaagagctgctgcagacggagctctctggcttcctggatgcccagaaggatgtggatgctgtggaca aggtgatgaaggagctagacgagaatggagacggggaggtggacttccaggagtatgtggtgcttgtggctgctctcacagt ggcctgtaacaatttcttctgggagaacagttgagcggccgcatcgataccgtcgactagagctcgctgatcagcctcgactgtgc cttctagttgccagccatctgttgtttgcccctcccccgtgccttccttgaccctggaaggtgccactcccactgtcctttcctaataaaatg aggaaattgcatcgcattgtctgagtaggtgtcattctattctggggggtggggtggggcaggacagcaagggggaggattgggaag acaatagcaggcgataaggatcttcctagagcatggctacgtagataagtagcatggcgggttaatcattaactacaaggaacccctag tgatggagttggccactccctctctgcgcgctcgctcgctcactgaggccgggcgaccaaaggtcgcccgacgcccgggctttgccc gggcggcctcagtgagcgagcgagcgcgcag Key:
ITR
cTnT Promoter
*hARC_Opt*

IRES hS100A1
BGH PolyA Signal

Recombinant AAV (rAAV) Particles

Further provided herein are rAAV viral particles or rAAV preparations containing such particles. The rAAV particles comprise a viral capsid and an rAAV vector as described herein, which is encapsidated by the viral capsid. Methods of producing rAAV particles are known in the art and are commercially available (see, e.g., Zolotukhin et al. Production and purification of serotype 1, 2, and 5 recombinant adeno-associated viral vectors. *Methods* 28 (2002) 158-167; and U.S. Patent Application Publication Numbers US 2007/0015238 and US 2012/0322861, which are incorporated herein by reference; and plasmids and kits available from ATCC and Cell Biolabs, Inc.). For example, a plasmid containing the rAAV vector may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

The rAAV particles or particles within an rAAV preparation disclosed herein, may be of any AAV serotype, including any derivative or pseudotype (e.g., 1, 2, 3, 4, 5, 6, 7, 8, 9, 10, 2/1, 2/5, 2/8, 2/9, 3/1, 3/5, 3/8, or 3/9). As used herein, the serotype of an rAAV an rAAV particle refers to the serotype of the capsid proteins of the recombinant virus. In some embodiments, the rAAV particle is rAAV6 or rAAV9. Non-limiting examples of derivatives and pseudotypes include AAVrh.10, AAVrh.74, AAV2/1, AAV2/5, AAV2/6, AAV2/8, AAV2/9, AAV2-AAV3 hybrid, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV- HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In particular embodiments, the capsid of any of the herein disclosed rAAV particles is of the AAVrh.10 serotype. In some embodiments, the capsid is of the AAV2/6 serotype. In some embodiments, the rAAV particle is a pseudotyped rAAV particle, which comprises (a) an rAAV vector comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). Methods for producing and using pseudotyped rAAV vectors are known in the art (see, e.g., Duan et al., *J. Virol.,* 75:7662-7671, 2001; Halbert et al., *J. Virol.,* 74:1524-1532, 2000; Zolotukhin et al., *Methods,* 28:158-167, 2002; and Auricchio et al., *Hum. Molec. Genet.,* 10:3075-3081, 2001).

rAAV Gene Therapy for Heart Diseases

The present disclosure is also directed to compositions comprising one or more of the disclosed rAAV particles or preparations. In some embodiments, the rAAV preparation comprises an rAAV particle comprising a rAAV vector containing ITRs of a first serotype (e.g., AAV3, AAV5, AAV6, or AAV9) and capsid proteins encapsidating the rAAV vector. In some embodiments, the capsid proteins are of the first serotype (e.g., AAV3, AAV5, AAV6, or AAV9). In some embodiments, the preparation has at least a four-fold higher transduction efficiency (e.g., in a human hepatocellular carcinoma cell line, such as Huh7) compared to a preparation prepared using a rAAV vector containing AAV2 ITRs.

As described herein, such compositions may further comprise a pharmaceutical excipient, buffer, or diluent, and may be formulated for administration to host cell ex vivo or in situ in an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a human subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions which result in diseases or disorders as described herein.

The rAAV vectors, rAAV particles, or the composition comprising the rAAV particles of the present disclosure, may be used for gene therapy for heart diseases in a human subject in need thereof. Examples of heart disease that may be treated using the methods and compositions of the present disclosure include, but are not limited to, cardiomyopathy and acute ischemia. In some embodiments, the heart cardiomyopathy is hypertrophic cardiomyopathy or dilated cardiomyopathy. Heart failure caused by cardiomyopathy or other heart diseases, comprise two components, calcium handling dysfunction and apoptosis. The rAAV vectors, particles, and compositions comprising the rAAV particles may be used for treatment of such heart failures when administered to a subject in need thereof, e.g., via vascular delivery into the coronary arteries and/or direct injection to the heart. The rAAV vectors, particles, and compositions comprising the rAAV particles drive the concurrent expression of cS100A1 protein and ARC proteins in the cardiomyocytes of the subject. S100A1 improves aspects of calcium handling, including normalization of sarcoplasmic reticular calcium transients leading to normalization of contractile function. ARC will block apoptosis initiated by mitochondrial and nonmitochondrial mechanisms (such as stretch-induced apoptosis), as well as improve mitochondrial function. Thus, the synergistic benefits of the two proteins expressed by the transgenes of the present disclosure can lead to better long-term therapeutic outcomes by targeting both aspects of cardiomyopathy.

The amino acid sequences of the human-derived S100A1 and ARC proteins are described below.

```
Human ARC:
                                        (SEQ ID NO: 13)
MGNAQERPSETIDRERKRLVETLQADSGLLLDALLARGVLTGPEYEALDA

LPDAERRVRRLLLLVQGKGEAACQELLRCAQRTAGAPDPAWDWQHVGPGY

RDRSYDPPCPGHWTPEAPGSGTTCPGLPRASDPDEAGGPEGSEAVQSGTP

EEPEPELEAEASKEAEPEPEPEPELEPEAEAEPEPELEPEPDPEPEPDFE

ERDESEDS

Human S100A1:
                                        (SEQ ID NO: 14)
MGSELETAMETLINVFHAHSGKEGDKYKLSKKELKELLQTELSGFLDAQK

DVDAVDKVMKELDENGDGEVDFQEYVVLVAALTVACNNFFWENS
```

In some aspects, the disclosed rAAV vectors encode a protein comprising an amino acid sequence at least 90%, at least 95%, or at least 99.5% identical to SEQ ID NO: 13 or 14. In some aspects, the disclosed rAAV vectors encode a first protein comprising an amino acid sequence at least 90%, at least 95%, or at least 99.5% identical to SEQ ID NO: 13 and a second protein comprising an amino acid sequence at least 90%, at least 95%, or at least 99.5% identical to SEQ ID NO: 14. In some embodiments, the rAAV vector encodes a protein that comprises SEQ ID NO: 13. In some embodiments, the rAAV vector encodes a protein that comprises SEQ ID NO: 14. In particular embodiments, the rAAV vector encodes a first protein that comprises SEQ ID NO: 13 and a second protein that comprises SEQ ID NO: 14.

In some embodiments, any of the disclosed rAAV vectors encode a first protein sequence that differs from the sequence of either of SEQ ID NO: 13 or 14 by 1, 2, 3, 4, 5, 6, 7, 8, 9, 10, 11, 12, or more than 12 amino acids. In some embodiments, any of the disclosed rAAV vectors encode proteins that are truncated by 1, 2, 3, or more than 3 amino acids at the N- or C-terminus relative to any of the sequences of SEQ ID NOs: 13 or 14.

Thus, other aspects of the present disclosure related to administering to a subject in need thereof, the rAAV particles of the present disclosure. In some embodiments, the number of rAAV particles administered to a subject may be on the order ranging from about $10^6$ to about $10^{14}$ particles/mL or about $10^3$ to about $10^{13}$ particles/mL, or any values in between for either range, such as for example, about $10^6$, $10^7$, $10^8$, $10^9$, $10^{10}$, $10^{11}$, $10^{12}$, $10^{13}$, or $10^{14}$ particles/mL. In some embodiments, the number of rAAV particles administered to a subject may be on the order ranging from about $10^6$ to about $10^{14}$ vector genomes(vgs)/mL or $10^3$ to $10^{15}$ vgs/mL, or any values in between for either range, such as for example, about $10^6$, $10^7$, $10^8$, $10^9$, $10^{10}$, $10^{11}$, $10^{12}$, $10^{13}$, or $10^{14}$ vgs/mL. The rAAV particles can be administered as a single dose, or divided into two or more administrations as may be required to achieve therapy of the particular disease or disorder being treated. In some embodiments, doses ranging from about 0.0001 mL to about 10 mLs are delivered to a subject.

If desired, rAAV particles and rAAV vectors may be administered in combination with other agents as well, such as, e.g., proteins or polypeptides or various pharmaceutically-active agents, including one or more administrations of therapeutic polypeptides, biologically active fragments, or variants thereof. In fact, there is virtually no limit to other components that may also be included, as long as the additional agents do not cause a significant adverse effect upon contact with the target cells or host tissues. The rAAV particles or preparations may thus be delivered along with various other pharmaceutically acceptable agents as required in the particular instance. Such compositions may be purified from host cells or other biological sources, or alternatively may be chemically synthesized as described herein.

Formulations comprising pharmaceutically-acceptable excipients and/or carrier solutions are well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle or preparation, and/or rAAV vector) or more, although the percentage of the active ingredient(s) may, of course, be varied and may conveniently be between about 1 or 2% and about 70% or 80% or more of the weight or volume of the total formulation. Naturally, the amount of therapeutic agent(s) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art when preparing such pharmaceutical formulations. Additionally a variety of dosages and treatment regimens may be desirable.

In certain circumstances, it will be desirable to deliver the rAAV particles or preparations, and/or rAAV vectors in suitably formulated pharmaceutical compositions disclosed herein; either subcutaneously, intravascularly, intracardially, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells (e.g., cardiomyocytes and/or other heart cells), tissues, or organs. In some embodiments, the rAAV particles or compositions comprising the rAAV particles of the present disclosure are administered intravascularly into the coronary arteries. In other embodiments, the disclosed rAAV particles or compositions are administered by direct injection to the heart of the subject. Direct injection to the heart may comprise injection into one or more of the myocardial tissues, the cardiac lining, or the skeletal muscle surrounding the heart, e.g., using a needle catheter.

The pharmaceutical formulations of the compositions suitable for injectable use include sterile aqueous solutions or dispersions. In some embodiments, the formulation is sterile and fluid to the extent that easy syringability exists. In some embodiments, the form is stable under the conditions of manufacture and storage, and is preserved against the contaminating action of microorganisms, such as bacteria and fungi. The carrier may be a solvent or dispersion medium containing, for example, water, saline, ethanol, polyol (e.g., glycerol, propylene glycol, and liquid polyethylene glycol, and the like), suitable mixtures thereof, vegetable oils or other pharmaceutically acceptable carriers such as those that are Generally Recognized as Safe (GRAS) by the United States Food and Drug Administration. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle or preparation, and/or rAAV vectors is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions may also be employed as liquid carriers.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see, for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles or preparations, Rep proteins, and/or rAAV vectors, in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the other ingredients from those enumerated above. In the case of sterile powders for the preparation of sterile injectable solutions, the preferred methods of preparation are vacuum-drying and freeze-drying techniques, which yield a powder of the active ingredient plus any additional desired ingredient from a previously sterile-filtered solution thereof.

The amount of rAAV particle or preparation, and/or rAAV vector compositions and time of administration of such compositions will be within the purview of the skilled artisan having benefit of the present teachings. It is likely, however, that the administration of therapeutically-effective amounts of the compositions of the present disclosure may be achieved by a single administration, such as for example, a single injection of sufficient numbers of infectious particles to provide therapeutic benefit to the patient undergoing such treatment. Alternatively, in some circumstances, it may be desirable to provide multiple or successive administrations of the rAAV particle or preparation, and/or rAAV vector compositions, either over a relatively short, or a relatively prolonged period of time, as may be determined by the medical practitioner overseeing the administration of such compositions.

The compositions of the present disclosure may include rAAV particles or preparations, and/or rAAV vectors, either alone or in combination with one or more additional active ingredients, which may be obtained from natural or recombinant sources or chemically synthesized. In some embodiments, rAAV particles or preparations are administered in combination, either in the same composition or administered as part of the same treatment regimen, with a proteasome inhibitor, such as Bortezomib, or hydroxyurea.

To "treat" a disease as the term is used herein, means to reduce the frequency or severity of at least one sign or symptom of a disease or disorder experienced by a subject. The compositions described above are typically administered to a subject in an effective amount, which is an amount capable of producing a desired result. The desired result will depend upon the active agent being administered. For example, an effective amount of a rAAV particle may be an amount of the particle that is capable of transferring a heterologous nucleic acid to a host organ, tissue, or cell.

Toxicity and efficacy of the compositions utilized in methods of the present disclosure may be determined by standard pharmaceutical procedures, using either cells in culture or experimental animals to determine the $LD_{50}$ (the dose lethal to 50% of the population). The dose ratio between toxicity and efficacy the therapeutic index and it may be expressed as the ratio $LD_{50}/ED_{50}$. Those compositions that exhibit large therapeutic indices are preferred. While compositions that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Other aspects of the present disclosure relate to methods and preparations for use with a subject, such as human or non-human subjects, a host cell in situ in a subject, or a host cell derived from a subject. In some embodiments, the subject is a mammal. In some embodiments, the subject is a companion animal. "A companion animal", as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a miniature pig, or mini-pig. In some embodiments, the subject is a human subject.

In some embodiments, the subject has or is suspected of having a heart disease that may be treated with gene therapy. In some embodiments, the subject is in any stages of heart failure. In some embodiments, the heart failure is caused by cardiomyopathy. In some embodiments, the heart failure is caused by hypertrophic cardiomyopathy or dilated cardiomyopathy.

The following examples are intended to be illustrative of certain embodiments of the present disclosure and are intended to be non-limiting. The entire contents of all of the references (including literature references, issued patents, published patent applications, and co pending patent applications) cited throughout this application are hereby expressly incorporated by reference.

EXAMPLES

Example 1: Therapeutically Targeting Multiple Aspects of Heart Failure

In some aspects, the present disclosure provides compositions and methods that are useful in treating one or more heart conditions (e.g., cardiomyopathy, hypertrophic cardiomyopathy, dilated cardiomyopathy, heart failure, heart disease, etc.). In some embodiments, compositions provided by the disclosure are administered intravascularly into coronary arteries. In some embodiments, compositions can be provided to a subject via multiple direct injections into the heart. An exemplary AAV construct that could be provided to a subject is depicted in FIG. 1. In certain embodiments, such an exemplary construct is encapsidated by a recombinant AAV (e.g., AAVrh.10 or AAV6) and comprises coding sequences of S100 calcium-binding protein A1 (S100A1) and Apoptosis Repressor with Caspase Recruitment Domain (ARC) to address two separate aspects of one or more heart conditions (e.g., cardiomyopathy). Both transgenes of the exemplary construct in FIG. 1 are driven by the cardiac TnT promoter and thus will only express in cardiomyocytes.

S100A1 improves aspects of calcium handling, including normalization of sarcoplasmic reticular calcium transients leading to normalization of contractile function. ARC will block apoptosis initiated by mitochondrial and non-mitochondrial mechanisms (e.g., stretch-induced apoptosis), as well as improve mitochondrial function. These two separate components of cardiac failure (calcium handling dysfunction and apoptosis) are addressed separately, but never together. As such, the synergistic benefits of such an approach provide therapeutic options that may result in improved long-term outcomes. By targeting both aspects of cardiomyopathy, compositions and methods provided by the present application may be used to address multiple heart conditions (e.g., hypertrophic or dilated cardiomyopathy), and will be beneficial at any stage of heart failure.

All publications, patents and sequence database entries mentioned in the specification herein are hereby incorporated by reference in their entirety as if each individual publication or patent was specifically and individually indicated to be incorporated by reference. In case of conflict, the present application, including any definitions herein, will control.

Example 2: Gene Therapy of Dilated Cardiomyopathy in Dogs

Dilated cardiomyopathy (DCM) is the second most common cause of acquired heart disease in dogs, most commonly affecting large breed dogs such as Doberman pinschers, great Danes and Irish Wolfhounds. In humans affected with this disease, there are surgical options such as cardiac transplantation and left ventricular assist devices. However in veterinary medicine the only therapeutic option is medical management of signs associated with heart failure. The prognosis for an affected dog depends on the stage of disease and the breed. For example, most Doberman pinschers live less than 6 months after the development of congestive heart failure (CHF). In contrast other breeds such as cocker spaniels tend to survive longer. As heart disease progresses, malfunctioning of channels that regulate calcium movement within cardiac cells promotes calcium cycling abnormalities, further dysregulating contraction and relaxation of the heart. Notably, calcium transport abnormalities have been recognized in dogs with naturally occurring DCM5 and also occur with heart failure secondary to many different etiologies.

Gene transfer strategies designed to normalize calcium cycling abnormalities ameliorate heart disease in small and large animal models with various forms of heart disease. In fact, clinical trials are already underway in humans to test this therapeutic approach to cardiomyopathy and preliminary results are encouraging. A pilot study is evaluating the efficacy of gene delivery designed to normalize calcium handling in Doberman pinschers affected with DCM and exhibiting CHF. Doberman pinschers are utilized because DCM is widespread in this breed and the disease tends to progress quickly and uniformly in this breed once CHF has developed. Novel modalities to address DCM will have significant impact on all canine breeds predisposed to this idiopathic disease including Doberman pinschers, boxers, great Danes, German shepherds, golden retrievers, etc. Notably, previous investigations into myocardial protein levels in samples from dogs with the most common forms of naturally occurring heart disease (canine degenerative valve disease and DCM) found multiple protein (including S100A1) levels were abnormal (S100A1 was decreased).

These findings suggest that gene delivery targeting S100A1 may effectively treat DCM as well myocardial failure developing secondary to degenerative valve disease. Additionally, apoptosis (programmed cell death) is more common in diseased myocardium and ARC is a potent and multifunctional inhibitor of apoptosis. Currently, the standard of care for veterinary heart failure is the medical management of fluid overload and congestion. Gene delivery techniques directed at abnormal myocardial regulatory molecules offer a mechanistic target that may allow the veterinary clinician to specifically address the myocardial disease process for the first time. Moreover, the cost associated with current vector production techniques and intramyocardial gene delivery of vector make the cost of this therapy within reach for many owners with costs expected to decrease over time.

A minimally invasive method of gene transfer using AAV 2/6 vectors resulted in transduction of >75% of myocardial cells in normal dogs (see Bish L T, Sleeper M M, Brainard B, et al. Percutaneous transendocardial delivery of self-complementary adeno-associated virus 6 achieves global cardiac gene transfer in canines. *Mol. Ther.* 16, 1953-9 (2008)). Six normal mongrel dogs were treated with either an AAV2 or an AAV6 vector encoding a dominant negative form of Phospholamban (dn-PLN) (a pseudophosphorylated form that competes with the native phospholamban therefore reducing its inhibitory effect on SERCA2a) (n=4) or AAV2/6 dn-PLN and S100A1 (n=2). All dogs remained healthy with normal cardiovascular function over 2 years post treatment, indicating that therapy did not cause myocarditis or significantly alter cardiac function, thus supporting the safety of this therapeutic approach. Cardiac function may be measured by ejection fraction, or any other method known in the art.

Indeed, over 40 normal and diseased dogs (see below) have been injected, and results to date indicate that the injection technique is well-tolerated. In addition, 20 random canine cases at the Matthew J. Ryan Veterinary Hospital of the University of Pennsylvania were sampled for antibodies to rAAV2/6 and found titers were within the acceptable range for treatment in 19 of the 20 dogs, indicating that prior immune responses will not exclude a significant proportion of therapeutic candidates. To determine if this therapeutic approach was efficacious for treatment of DCM, Portuguese water dogs with a severe form of rapidly progressing juvenile DCM were then treated. Notably, dogs injected with AAV2/6 dn-PLN exhibited a marked decrease in phosphorylated PLN, supporting the potential ability of this approach to normalize calcium cycling in this disease model. Moreover, gene delivery with a vector containing both dn-PLN and S100A1 slowed the development of CHF secondary to DCM to a greater degree than did delivery of a vector containing dn-PLN alone. The combination vector delayed onset of CHF by an average of 4 weeks as compared to dn-PLN therapy alone. For this reason, the combined vector approach is utilized in a pilot study to determine if gene therapy is effective in prolonging the life of Dobermans affected with adult-onset DCM and congestive heart failure.

The study has a blinded, placebo controlled design. Based on the last 12 Doberman pinscher cases of DCM and CHF that have been treated, there was a mean survival of 148 days (standard deviation of 160 days). Using a power of 0.8, alpha (2 sided) of 0.05 and a ratio of cases to controls of 1, a sample size of 13 dogs in each group are required to detect a difference in 6 month survival. This calculation was determined using a parametric sample size test. Twenty six Doberman pinschers with DCM and controlled CHF are enrolled. In order to be eligible for enrollment, the dog must have a circulating neutralizing antibody titer to AAV2/6 of less than 1:20 and be clear of extra-cardiac disease. Additionally, dogs with concomitant congenital heart disease or evidence of primary mitral valvular disease are excluded. At baseline (time of enrollment) an antibody titer, CBC, and chemistry panel is used for screening purposes. Dogs undergo a 3-minute electrocardiogram (ECG) and a complete echocardiogram (ECHO) and owners complete a previously validated quality of life questionnaire. The ECG is evaluated for interval duration and the presence of arrhythmias. The ECHO includes 2D, M-mode and Doppler studies (including tissue Doppler). Thoracic radiographs are used to stage the disease (dogs are clinically compensated with a history of congestive heart failure).

Dogs fulfilling the requirements for enrolment are randomly assigned to the placebo arm (cardiac injection with saline) or the gene therapy group (cardiac injection with AAV2/6-ARC-s100a1). Standard medical management for DCM and congestive heart failure continues throughout the study in all dogs (pimobendan, angiotensin inhibitor and diuretic therapy). Saline instead of empty capsid is used as the sham therapy so that control dogs can undergo gene delivery if the treatment group demonstrates a significant improvement compared to the placebo group. At 2, 4, 6, 9, and 12 months following therapy ECG, ECHO, a quality of life questionnaire and laboratory analyses are repeated. Statistical analysis is performed at bi-monthly intervals.

Figure 2:
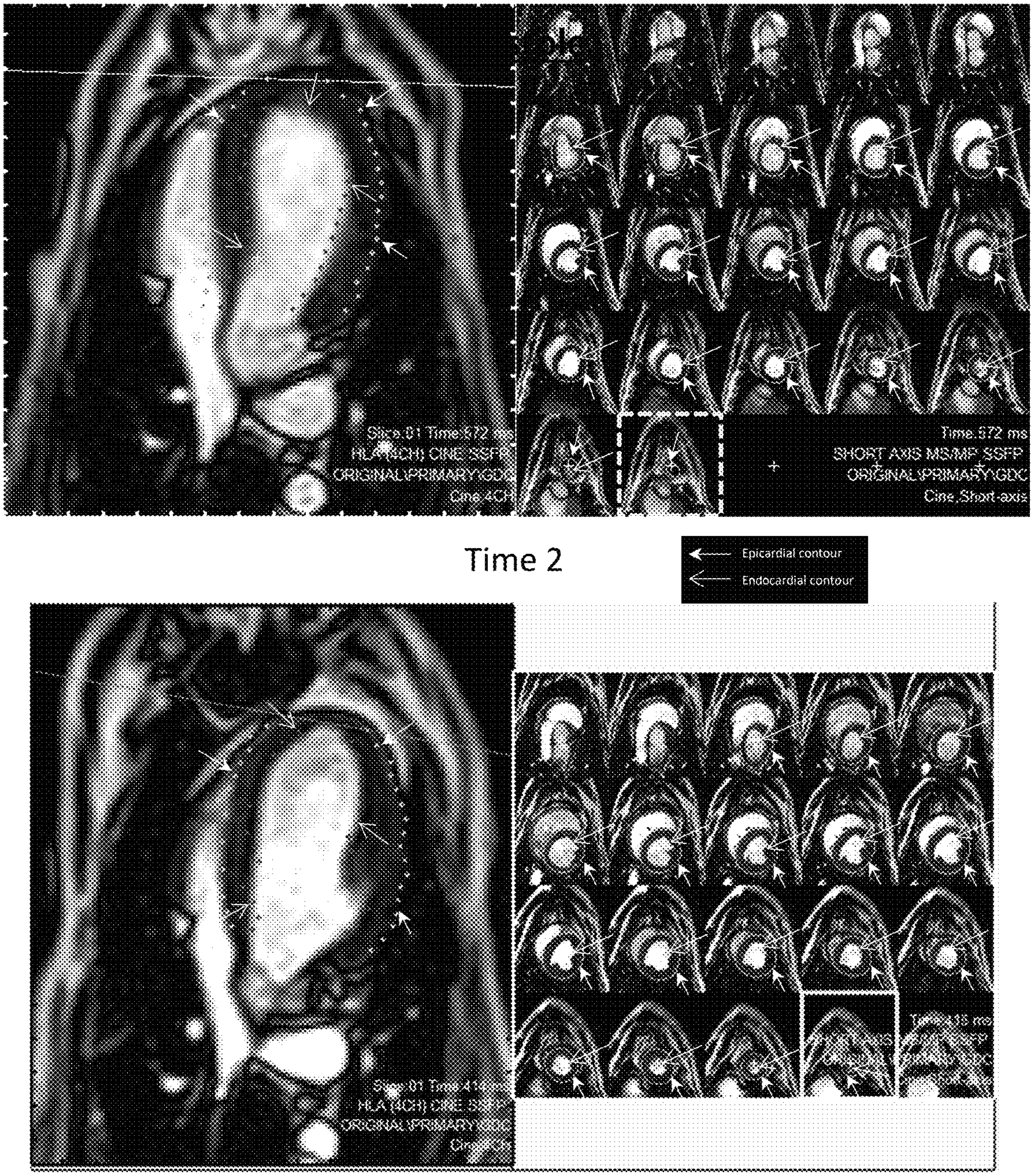
FIG. 2 depicts diastolic MRI imaging from a treated muscular dystrophy dog at baseline and several weeks after gene delivery. The data support stable or slightly improved cardiac remodeling with a mild decrease in the diastolic left ventricular volume.

FIGS. 2 and 3 depict diastole (relaxation) and systole (contraction) data, respectively, in a treated muscular dystrophy dog. The endocardial and epicardial contours can be seen in each of the figures. The data indicates stable or slightly improved function post treatment over several weeks as seen in Table 1. Table 1, below, shows the left ventricular mass (LVM [g]), end diastolic volume (EDV [ml]), end systolic volume (ESV [ml]), stroke volume (SV [ml]), ejection fraction (EF [%]), and cardiac output (CO [l/min]) results for the data taken at times 1 (pre-treatment) and time 2 (post-treatment).

TABLE 1

| Acquisition Date | LVM [g] | EDV [ml] | ESV [ml] | SV [ml] | EF [%] | CO [l/min] |
|---|---|---|---|---|---|---|
| Time 2 | 91.395035 | 54.22289 | 24.595001 | 29.627889 | 54.640926 | 3.940509 |
| Time 1 | 87.251524 | 57.471229 | 25.660014 | 31.811215 | 55.351548 | 3.117499 |

Example 3: Assessment of Dystrophy Phenotypes Following Vector Delivery into Mice and Dogs Cardiac AAV gene delivery of the S100A1/ARC self-complementary vector was assessed in mouse and dog models of Duchenne muscular dystrophy (dystrophin-deficiency). Earlier, the AAV8 (including multiple variants thereof), AAV9, and AAVrh.10 serotypes were compared in their ability to infect canine hearts, and AAVrh.10 was found to be the most efficient. For this reason, AAVrh.10 was used for all experiments described in this Example.

Figure 4:
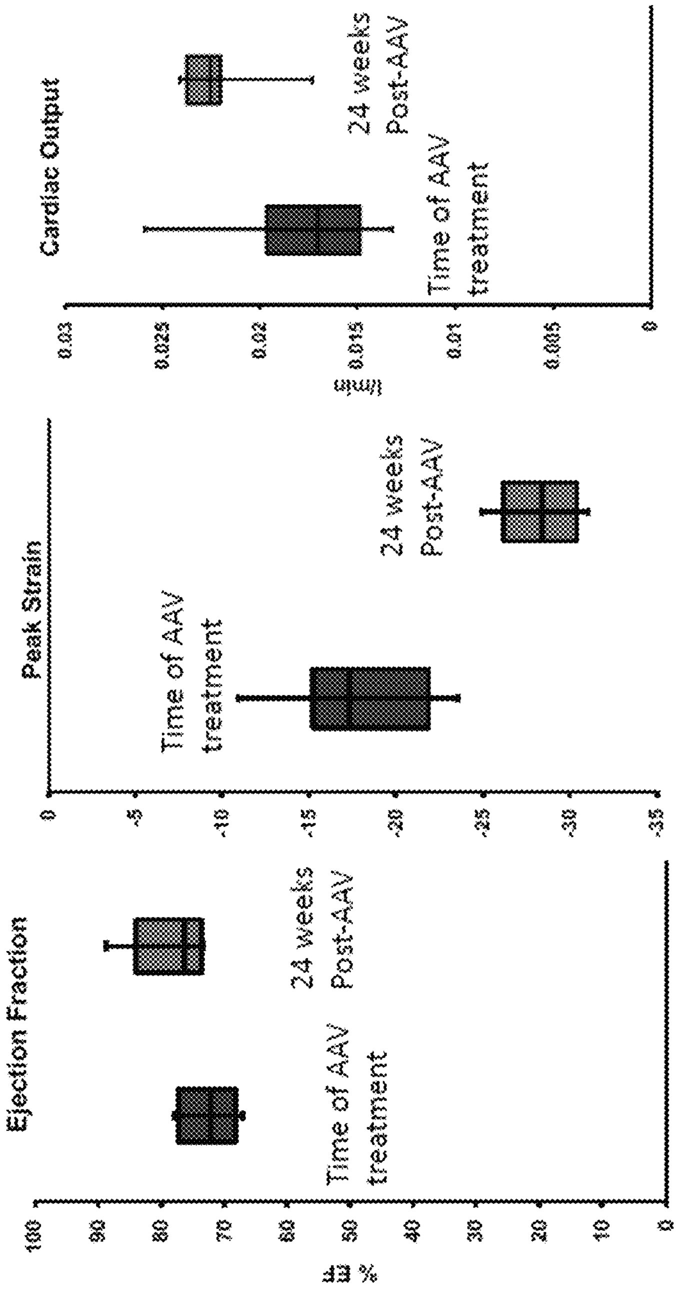
FIG. 4 shows ejection fraction, peak strain, and cardiac output of D2.mdx mice after AAVrh.10-S100A1/ARC treatment. Over a 24 week period, mice injected with the therapeutic AAV had better maintained ejection fractions, strain development, and cardiac output as compared to sham injected mice.
Figure 5:
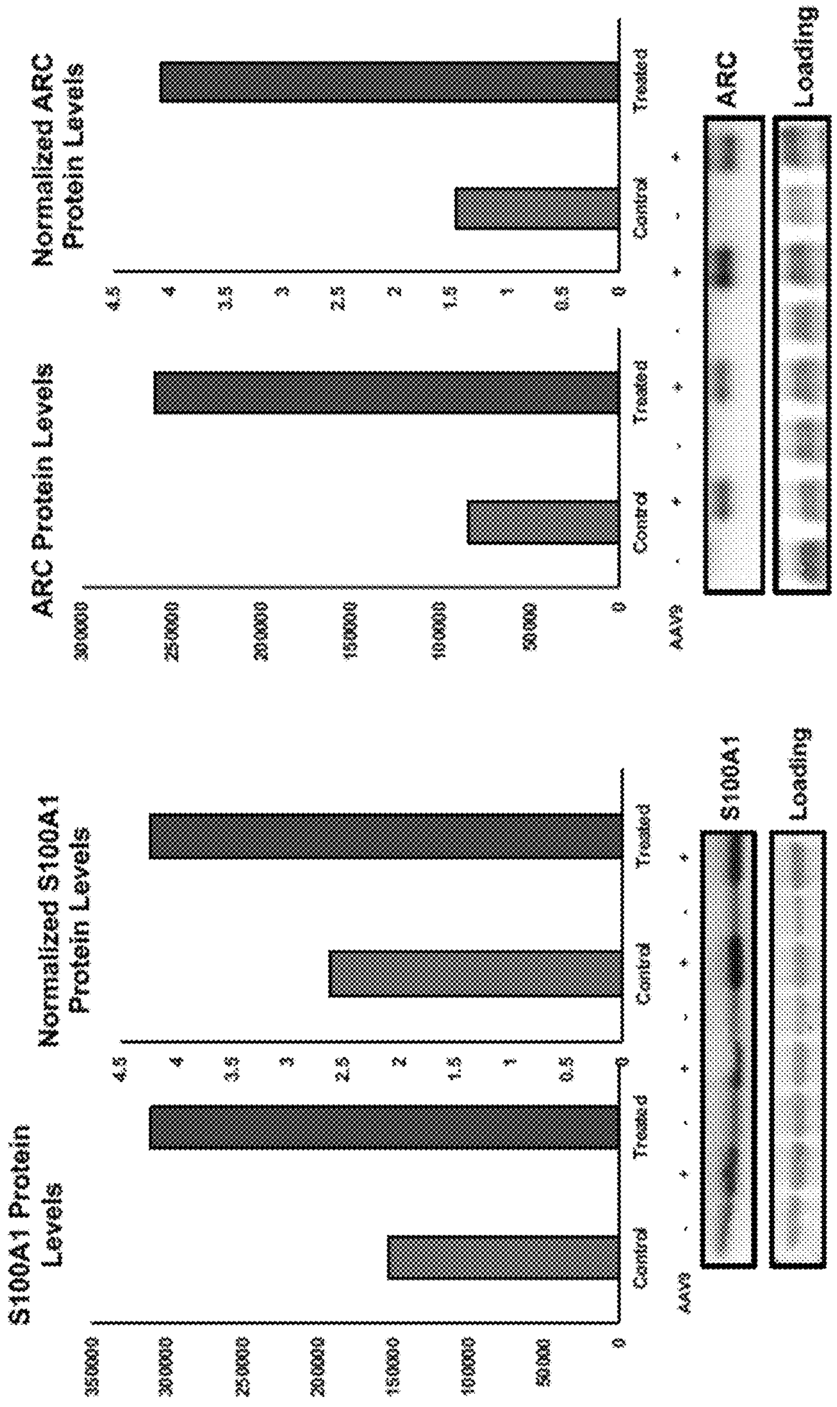
FIG. 5 shows S100A1 and ARC expression levels in mice treated with recombinant AAVrh.10-S100A1/ARC vector and control mice. Protein analysis (Western blots) confirmed that both S100A1 and ARC levels were elevated in the treated tissues as compared to controls (sham injected).
Figure 6:
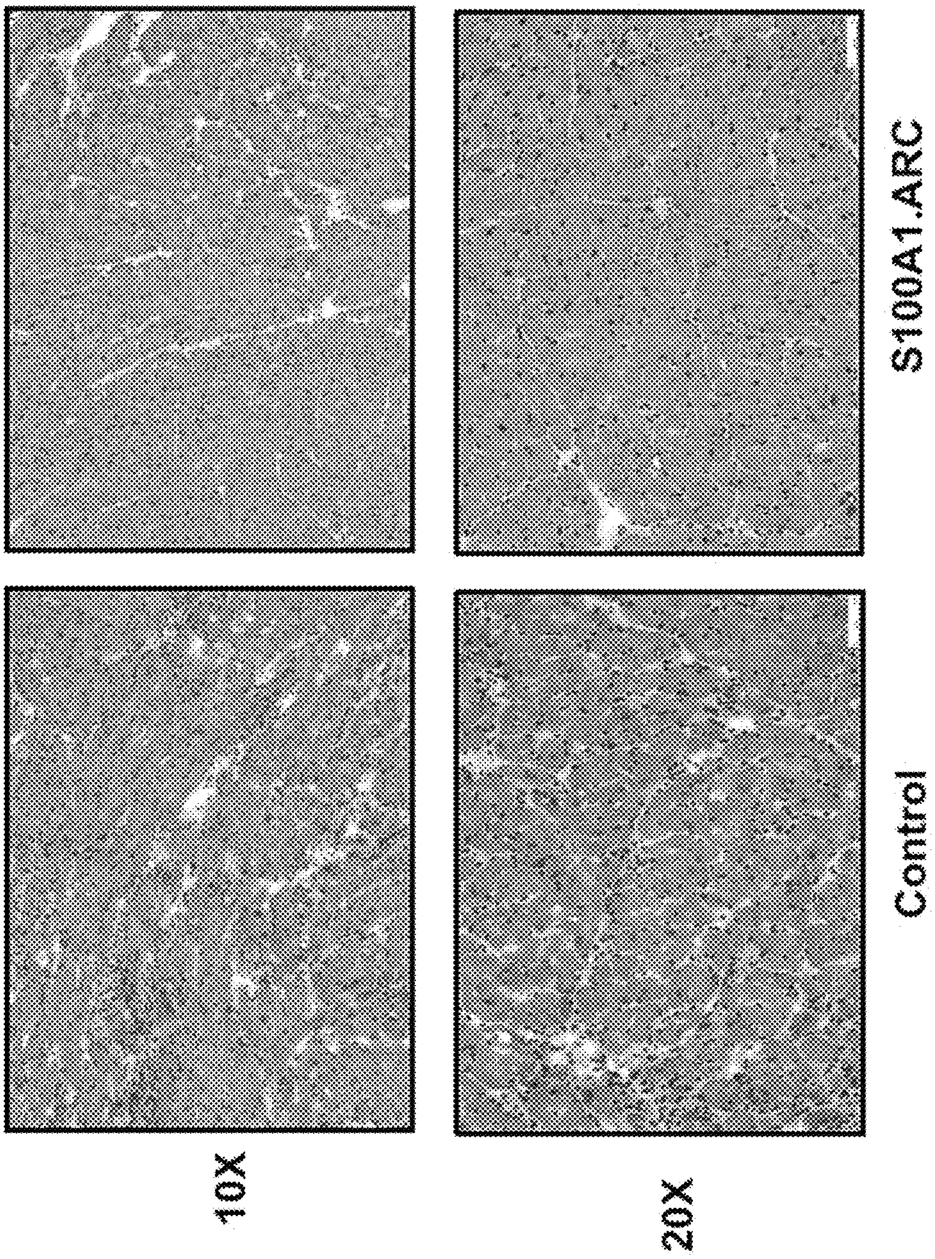
FIG. 6 shows cardiomyocytes of control and treated mice under 10× and 20× magnification. Cardiac histology data indicates that the treated mice exhibited less DMD pathology as compared to control hearts.

Mdx (dystrophin-deficient) mice on the DBA/2J background ("D2.mdx") were injected at 4 weeks of age with recombinant AAVrh.10-S100A1/ARC vector (referred to below as the "therapeutic AAV") and sacrificed 24 weeks later. D2.mdx mice recapitulate several human characteristics of Duchenne muscular dystrophy myopathy, such as reduced lower hind limb muscle mass, atrophied myofibers, increased fibrosis and inflammation, and muscle weakness. Over this 24 week period, the mice injected with the therapeutic AAV had better maintained ejection fractions, strain development, and cardiac output as compared to sham injected mice (see FIG. 4), as measured by cardiac MRI. Protein analysis (Western blots) confirmed that both S100A1 and ARC levels were elevated in the treated tissues as compared to controls (sham injected) (see FIG. 5). Furthermore, cardiac histology demonstrated that the treated hearts demonstrated much less pathology as compared to control hearts (see FIG. 6).

Figure 18:
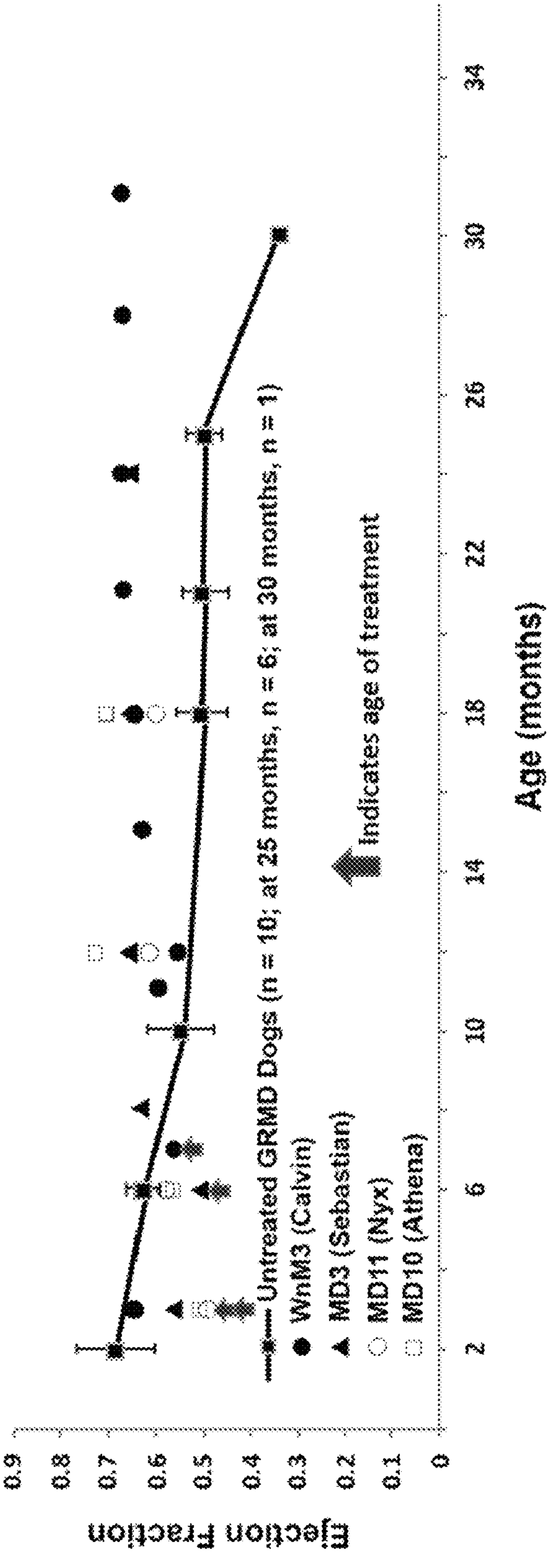
FIG. 18 shows ejection fraction changes with age in the colony's untreated GRMD dogs (n=10), and the ejection fraction changes in individual GRMD dogs that received treatment with the AAVrh.10-S100A1/ARC vector at the ages indicated by the red arrows (between 3 and 7 months of age). In all four of the treated dogs, the ejection fraction improved after the treatment and has been stable thereafter.

Two GRMD (dystrophin-deficient) dogs, the dog model of human Duchenne muscular dystrophy, were injected with the therapeutic vector at the time of first decrease in their cardiac ejection fractions via catheter delivery into the coronary arteries. Cardiac ejection fractions represent constitute a symptom indicating onset of cardiomyopathy. Earlier findings from a natural history study of dog subjects indicated that, as soon as ejection fractions begin to fall, they continue to fall progressively over the next year (FIG. 18). Dogs typically do not survive longer than 8-12 months after the ejection fraction begins this steady decrease.

Figure 7:
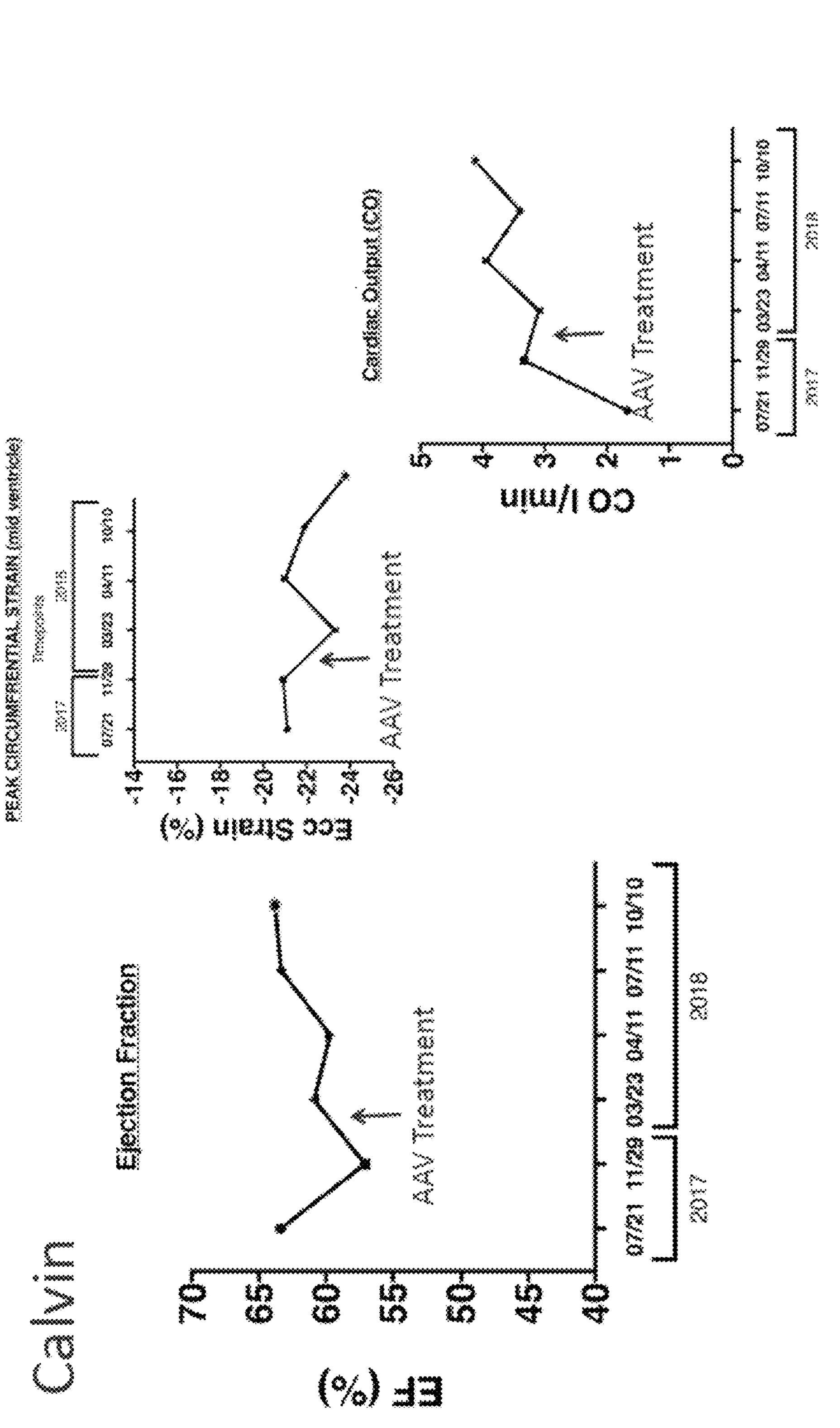
FIG. 7 shows that the first (of two) dystrophin-deficient dogs (GRMD dogs), named Calvin, showed improved cardiac function (measured by ejection fraction) after recombinant AAVrh.10-S100A1/ARC treatment. Both injected dogs exhibited improvements in ejection fraction and other cardiac parameters following treatment, measured by cardiac MRI and confirmed by echo data.
Figure 8:
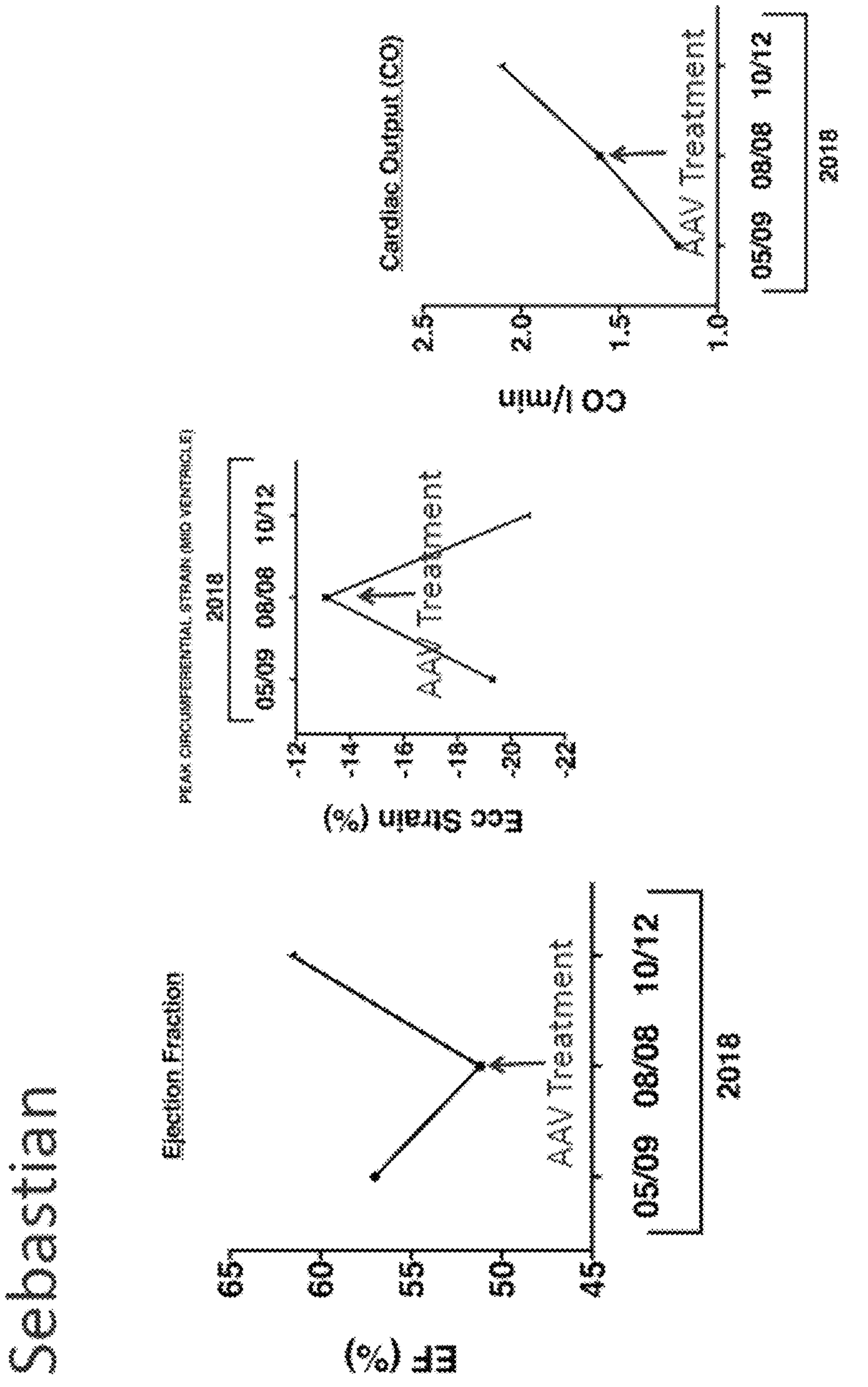
FIG. 8 shows data that the second GRMD dog, named Sebastian, showed improved cardiac function after AAVrh.10-S100A1/ARC treatment.

As shown in FIGS. 7 and 8, both subjects showed improvements in ejection fraction and other cardiac parameters several months after treatment with AAVrh.10-S100A1/ARC, as measured by cardiac MRI and confirmed by echo measurements. Nearly 12 months after treatment, the first subject exhibited a steady ejection fraction within the normal range. Likewise, nearly 7 months after treatment, the second subject exhibited a steady, normal ejection fraction.

Figure 9A:
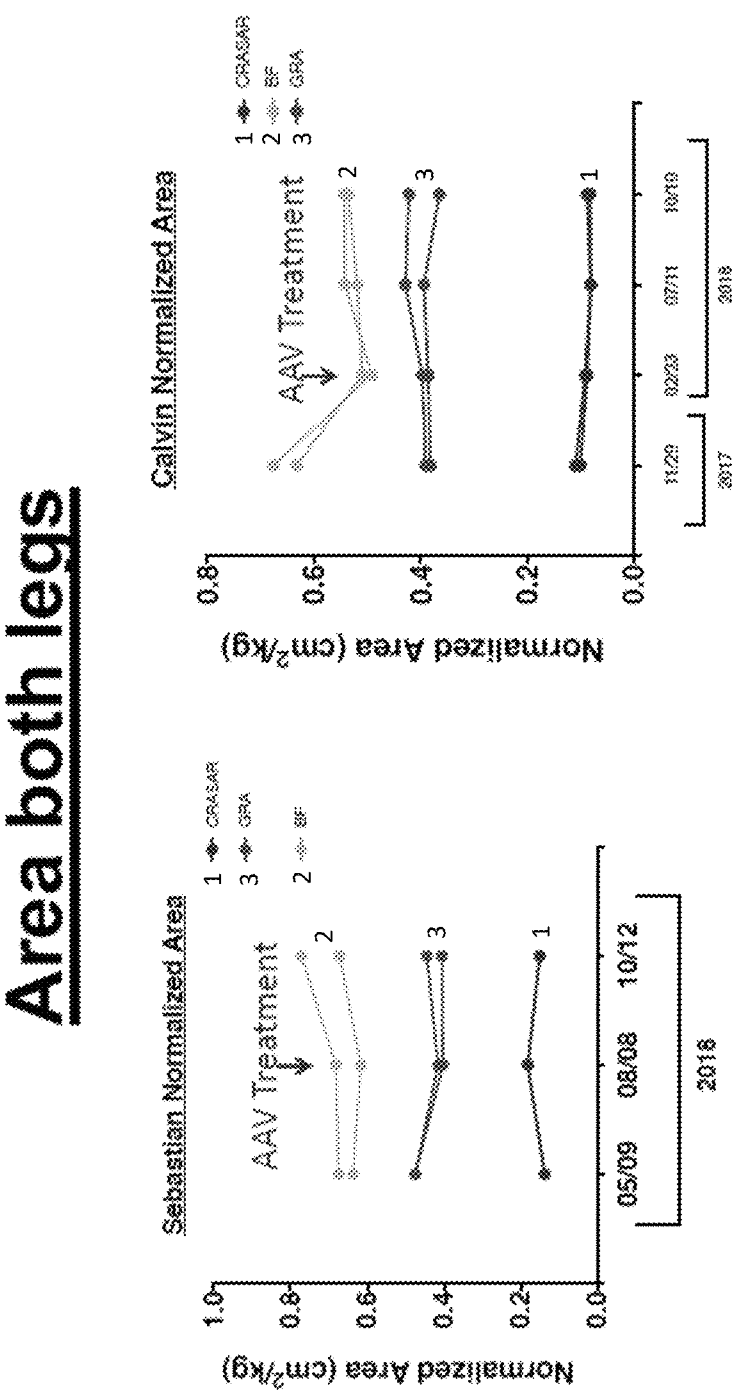
FIGS. 9A to 9C show that AAV-S100A1/ARC treatment decreased serum creatine kinase (CK) levels and prevented muscle atrophy in the GRMD dogsMRI measurements of limb muscle mass, as measured by the area of both legs (FIG. 9A), maximum cross-sectional area (CSA) (FIG. 9B), and volume of both legs (FIG. 9C). The results demonstrate that skeletal muscle mass had either increased or remained unchanged following cardiac treatment.
Figure 9B:
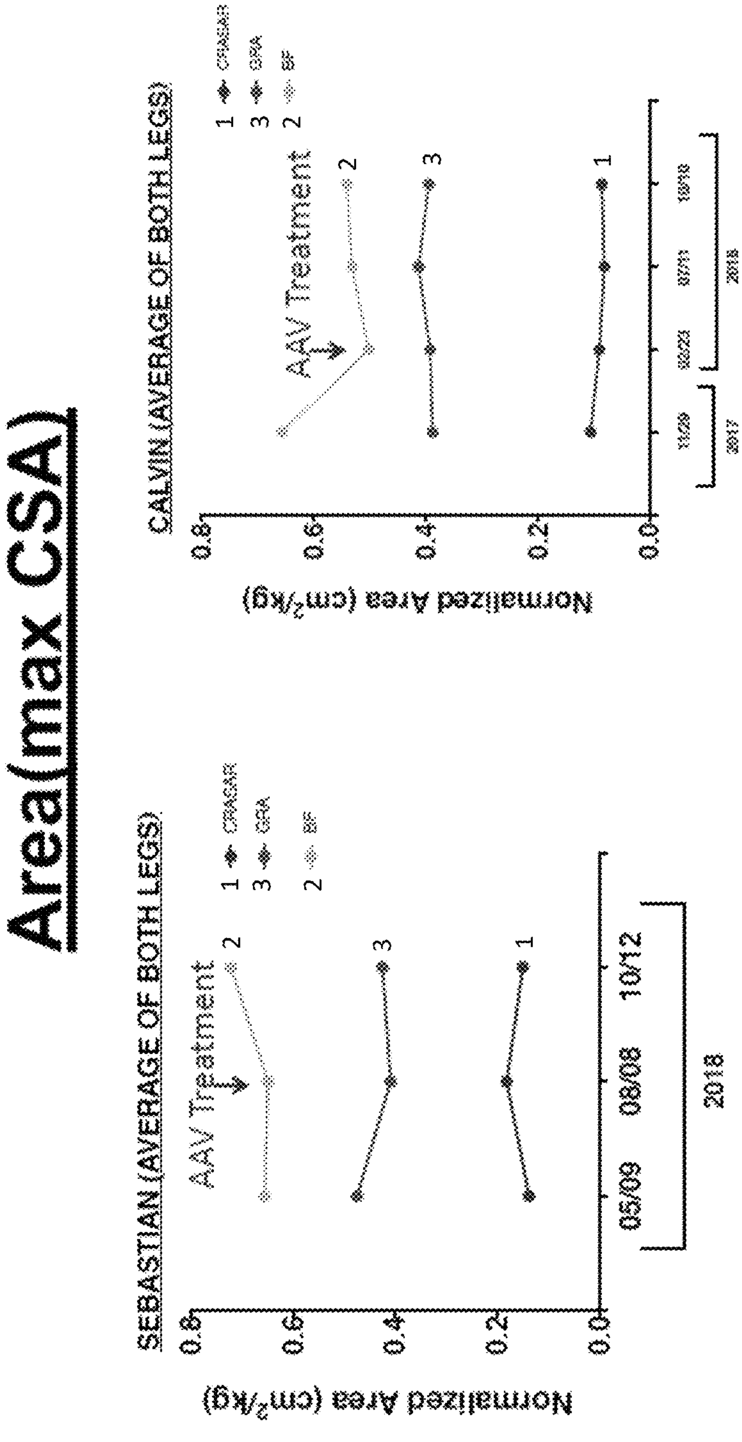
Figure 9C:
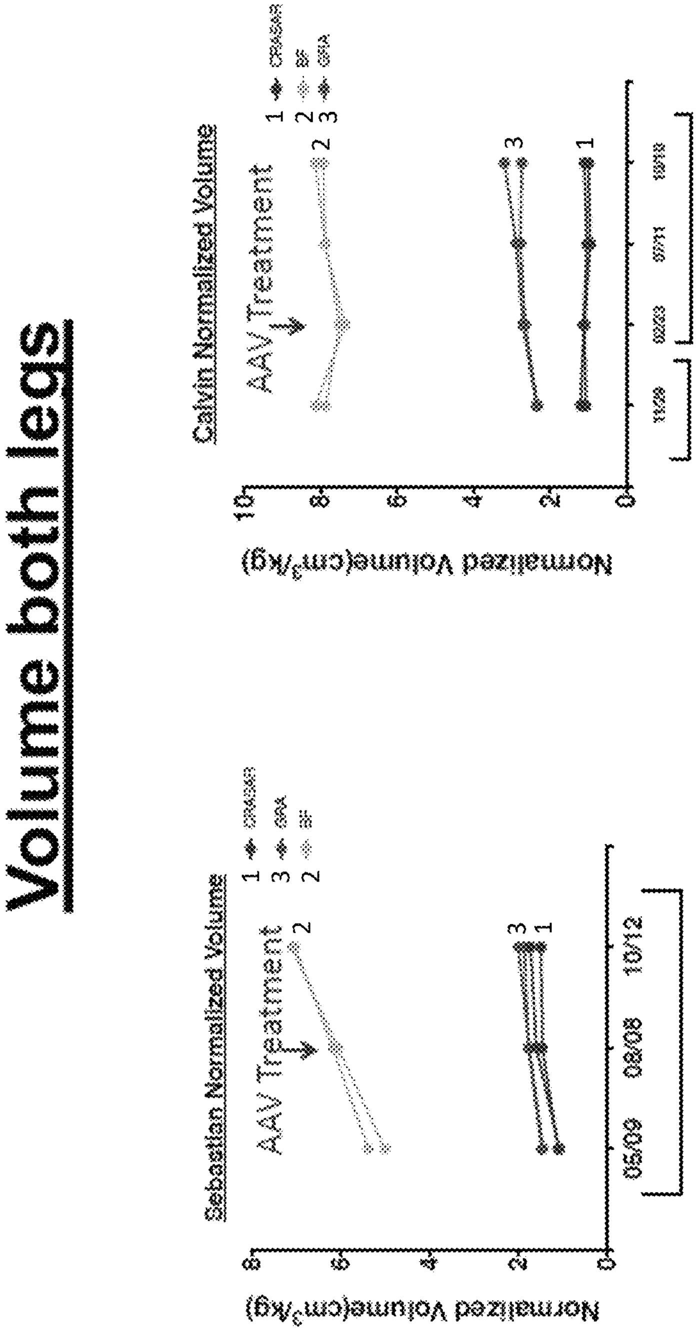
Figure 10:
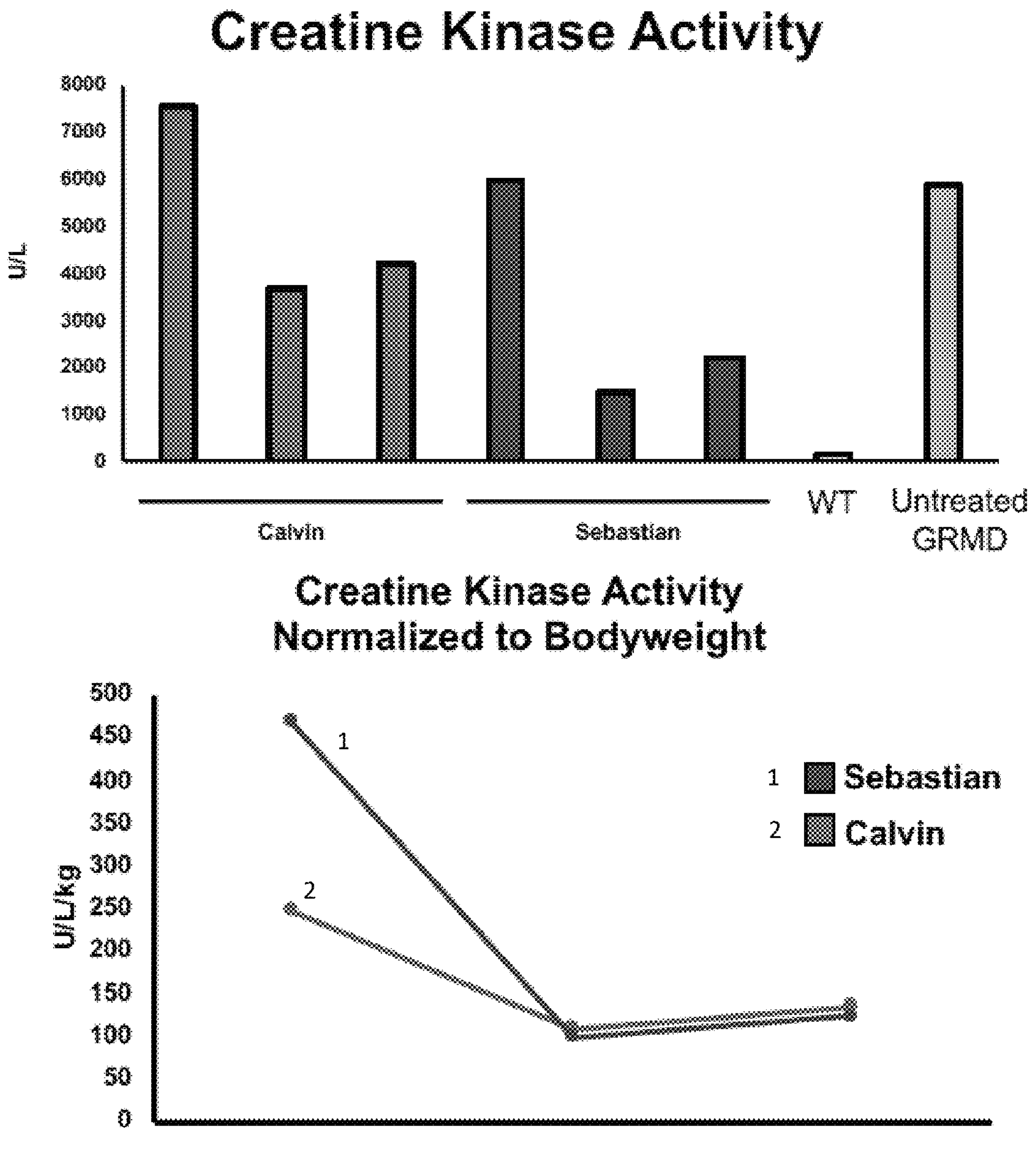
FIG. 10 shows that circulating creatine kinase levels (CK) levels in skeletal muscle of the GRMD subjects were reduced after AAVrh.10-S100A1/ARC injection, indicating a reduction in ongoing muscle damage.

Not only was cardiac function improved, but there was also a constant improvement in the exercise capacity of the dogs, as evaluated qualitatively by filming the subjects during exercise. Consistent with this improved exercise capacity, MRI measurements of the subjects' limbs demonstrated that skeletal muscle mass was either augmented or unchanged following AAV treatment (FIGS. 9A to 9C). In addition, circulating creatine kinase levels (CK) levels in skeletal muscle was reduced post-treatment (FIG. 10), indicating that a reduction in ongoing muscle damage.

Example 4: Treatment of DCM Dog Subjects

Doberman pinschers have the highest incidence of DCM of any dog breed. The genetic bases of this are known for only a subset of the dogs. This provides a large animal model of DCM and heart failure, without any other genetic complications. Only dogs that are in late stage heart failure are being treated with the same AAV.S100A1.ARC vector that is being used in the GRMD dogs. The goal of the treatment is to both improve cardiac function and prolong life.

Two Doberman pinscher subjects have been treated with AAVrh.10-S100A1/ARC via catheter delivery into the coronary arteries to date, wherein both dogs had experienced heart failure at the time of treatment. Both dogs showed rapid improvement following treatment. Each dog was assessed by two rounds of echocardiographs after treatment to evaluate cardiac structural and functional parameters, including (but not limited to) ventricular volumes, wall thickness and chamber diameters in diastole and systole, as well as fractional shortening and ejection fraction.

The first dog was treated with an ejection fraction of only 10%, and was thus close to death at the time of treatment. Within 24 hours post-treatment, the ejection fraction improved to 25%. At the dog's first follow up visit at 4 months post-treatment the ejection fraction had held steady at 26%. At the second follow up at 6 months, its ejection fraction was 32%. The dog died from congestive heart failure at 8 months of age. Thus, the treatment appeared to prolong life, but cardiac function was already too compromised at treatment to allow long-term survival.

The second treated Doberman pinscher had an ejection fraction of 32% prior to treatment—a fraction that is low, but not in immediate danger of death. The dog's ejection fraction improved to 49% within 24 hours following treatment, which is within normal range. At the 4 months post treatment exam the dog's ejection fraction was 52%, and at the 8-month exam, the ejection fraction was 50%. Prior to return for a one-year exam, the dog was diagnosed with lung cancer and died two months later. Its cause of death was unrelated to heart failure.

Based on these findings, AAVrh.10-S100A1/ARC treatment is able to restore cardiac function in canines to normal range.

Example 5: Evaluation of Vectors Comprising Human-Derived cDNA Sequences

Plasmids comprising human-derived ARC ("hARC") and S100A1 ("hS100A1") cDNA sequences were constructed for evaluation in mice. The native human cARC and S100A1 genes were codon-optimized for expression in human cells.

These plasmids comprise the nucleotide sequences of SEQ ID NOs: 9-12. Each of these plasmids comprises cARC and S100A1 cDNA sequences operably controlled by a cTnT promoter, as well as an IRES between these two sequences. All four plasmids comprise a codon-optimized human cARC (hARC) sequence. The plasmids set forth in SEQ ID NOs: 9 and 10 further comprise a codon-optimized hS100A1 sequences; and the plasmids set forth in SEQ ID NOs: 11 and 12 further comprise a wild-type hS100A1 sequence.

Each of these four plasmids was cloned into a self-complementary AAVrh.10 vector and subsequently encapsidated into an rAAV particle. The rAAVrh.10 particles comprising these vectors were administered to mice.

Expression levels of ARC and S100A1 in the mice were evaluated. Dystrophy phenotypes and cardiac function, including cardiac ejection fraction, were monitored and evaluated.

Example 6: Long-Term Mouse and Dog Studies

Dystrophic Mouse Studies

Figure 15:
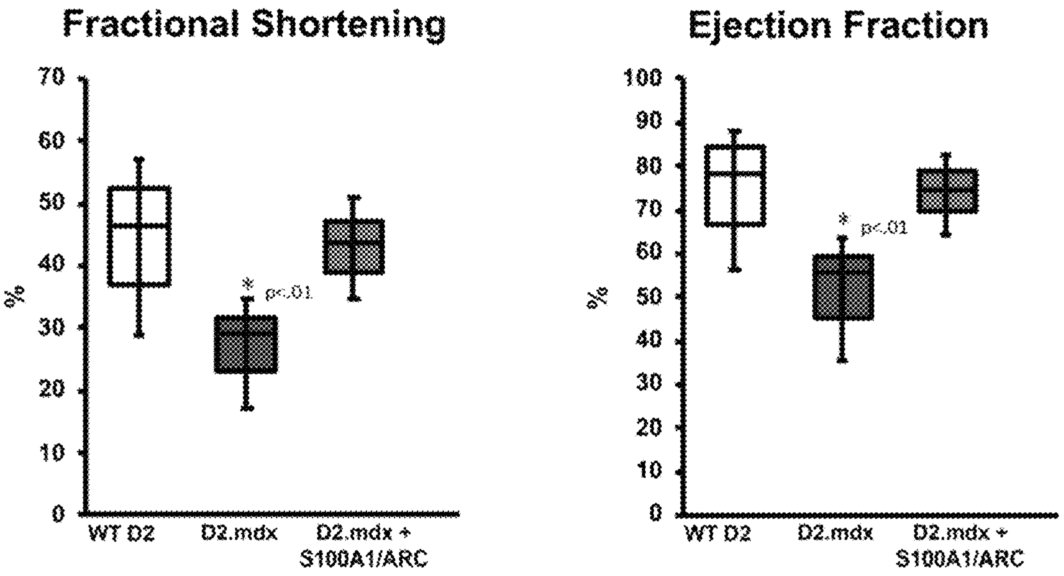
FIG. 15 shows fractional shortening and ejection fraction D2.mdx mice (n=12) at 10 months of age, following AAVrh.10-S100A1/ARC treatment at 1 month of age. Both the fractional shortening and ejection fraction were not significantly different from wild type D2 mice in the AAVrh.10-S100A1/ARC treated mice, while the untreated D2.mdx mice had significant reductions in function.
Figure 16:
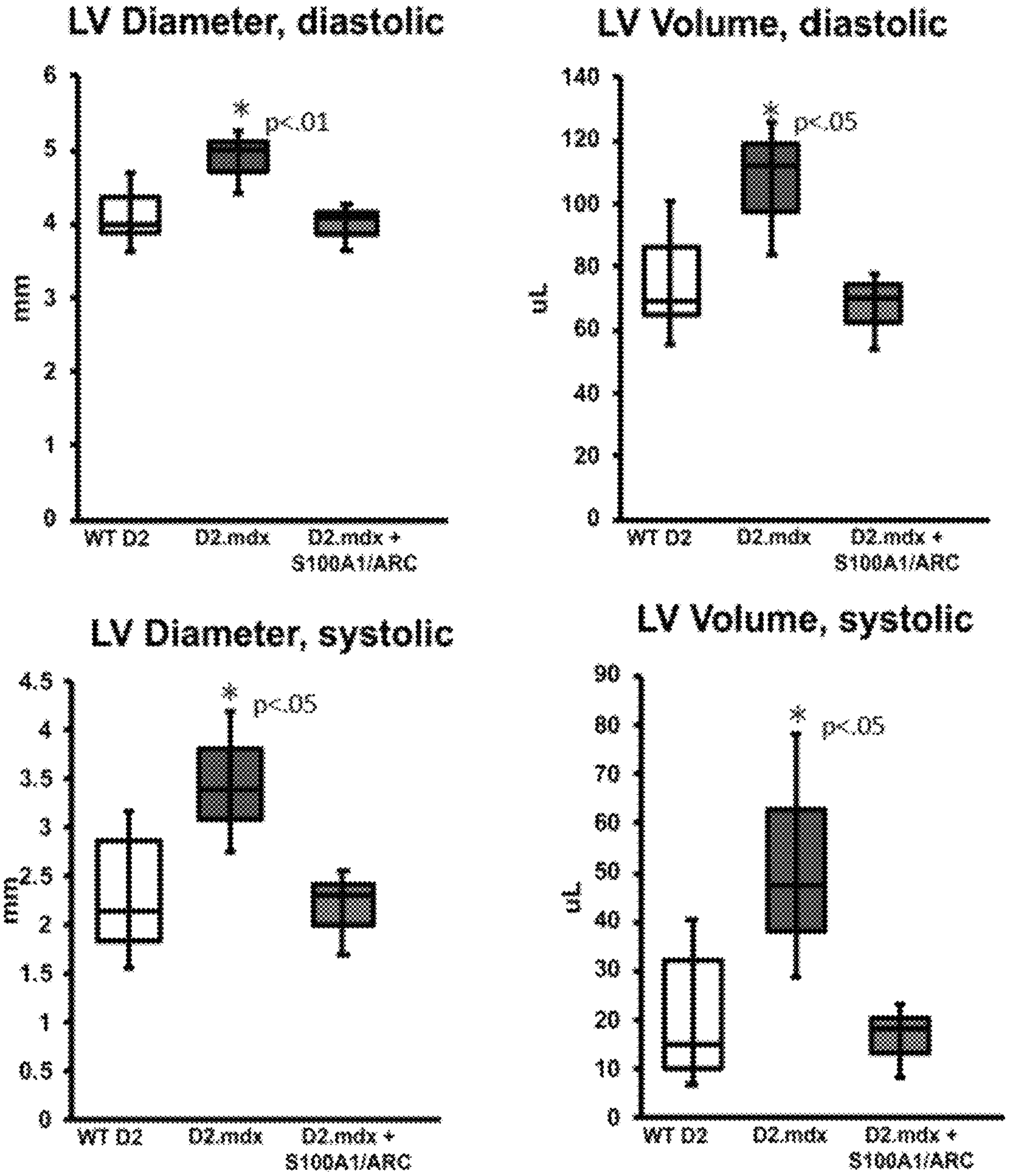
FIG. 16 shows left ventricular volumes and diameters of D2.mdx mice (n=12) at 10 months of age, following AAVrh.10-S100A1/ARC treatment at 1 month of age. Increased volume and diameters during both diastole and systole are indicative of dilated cardiomyopathy. Both the volume and diameter were not significantly different from wild type D2 mice in the AAVrh.10-S100A1/ARC treated mice, while the untreated D2.mdx mice had significant increases in both parameters.
Figure 17:
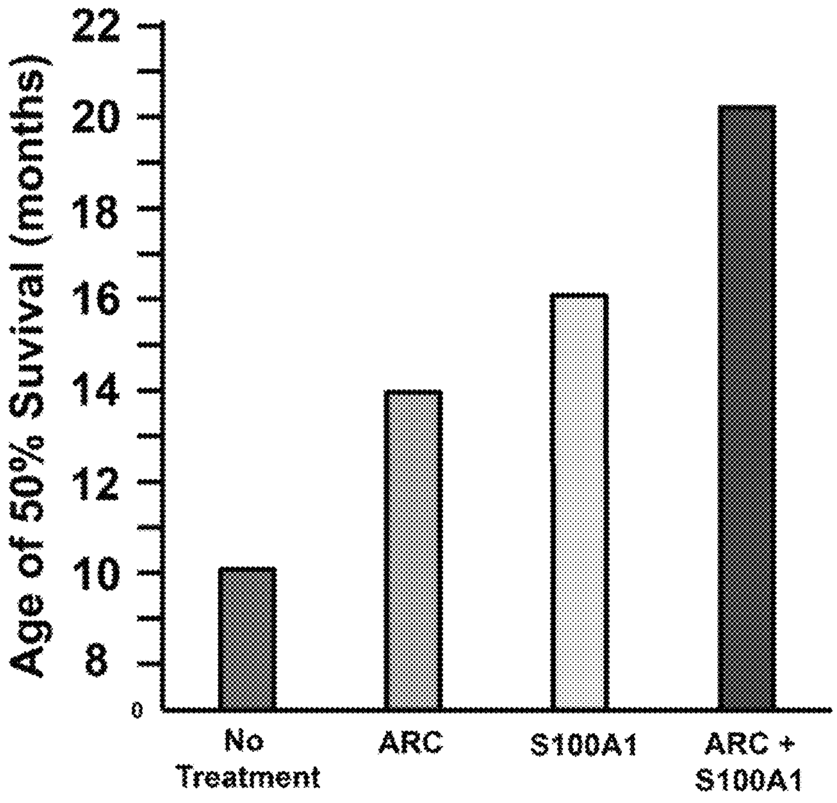
FIG. 17 shows the age of 50% survival of D2.mdx.sk_utrophin mice (n=12 per group at study initiation) that were allowed to begin exercising at 6 weeks of age, but did not receive treatment until 6 months of age. In the control group that received no treatment, median survival was 10 months of age. The group receiving AAVrh.10-ARC had a median survival of 14 months, the group receiving AAVrh.10-S100A1 had a 16-month median survival, and the group receiving AAVrh.10-S100A1/ARC had a median survival of 20 months.

AAV Cardiac Gene Delivery of S100A1 and ARC Leads to Preservation of Cardiac Function In addition to mouse studies previously provided (FIGS. 4-6), two types of longer-term studies were conducted, the results of which are summarized in FIGS. 15-17. Shown in FIGS. 15 and 16 are data from dystrophin-deficient mice on a severely fibrotic background, the DBA/2J (also referred to as "D2") mouse, thus creating what is referred to as the D2.mdx mouse. These mice were treated with AAV containing the dual transgene (S100A1 and ARC) cassette, operably controlled by the cardiac troponin T (cTnT) promoter, at the age of 1 month. The mice were housed in a sedentary environment until 10 months of age, at which time their cardiac status was evaluated.

Superiority of AAV Cardiac Gene Delivery of S100A1 and ARC Compared to Either Transgene Alone In parallel with these studies, a survival study was also conducted in D2.mdx mice in which there was transgenic rescue of only the skeletal muscle by expression of utrophin under control of the skeletal muscle alpha-actin promoter (see Rafael J A, et al. Skeletal muscle-specific expression of a utrophin transgene rescues utrophin-dystrophin deficient mice. *Nat Genet.* 19:79-82, 1998), which are referred to as D2.mdx.sk_utrophin mice. The point was to create a mouse that had a pure dilated cardiomyopathy, leading to heart failure and death, without any disease of the pulmonary musculature, or skeletal musculature in general. This allowed for the mice to be exercised by housing them individually with running wheels. The exercise creates additional load and stress on the hearts, leading to an acceleration of the development of the cardiomyopathy and heart failure. In order to better model the clinical situation in which individuals would not receive treatment prior to the onset of measurable cardiac disease, the mice were treated at 6 months of age, at which time fibrosis is present and cardiac functional abnormalities begin to emerge.

To assess the potential superiority of delivery of S100A1+ARC together in the same construct, relative to delivery of ARC or S100A1 alone, either no transgene (control) was delivered, or an rAAV vector containing the same cardiac promoter used in the dual transgene construct was delivered, but driving either the same S100A1 or ARC cDNA used in the dual cassette, but alone and not in combination. Thus the ability of either ARC alone, S100A1 alone, or the combination of S100A1 and ARC was compared to prolong life in this heart failure model.

As shown in FIG. 17, either transgene alone was able to significantly extend lifespan, ARC by 4 months and S100A1 by 5 months. However, the combination of transgenes, S100A1 and ARC, extended lifespan by 10 months, to 20 months of age. The wild type D2 mice only have a lifespan of ~23 months, so this represented a remarkably strong rescue of the heart. The combination of the transgenes into a dual rAAV construct provided synergistic efficacy. Because administration of the vector extended the lifespan of D2 mice to approximately wild-type lifespan and extended lifespan relative to single-transgene vectors by between 4 and 5 months, these results represent a statistically significant improvement relative to single-vector therapies.

Dystrophic Dog Studies

Figure 19:
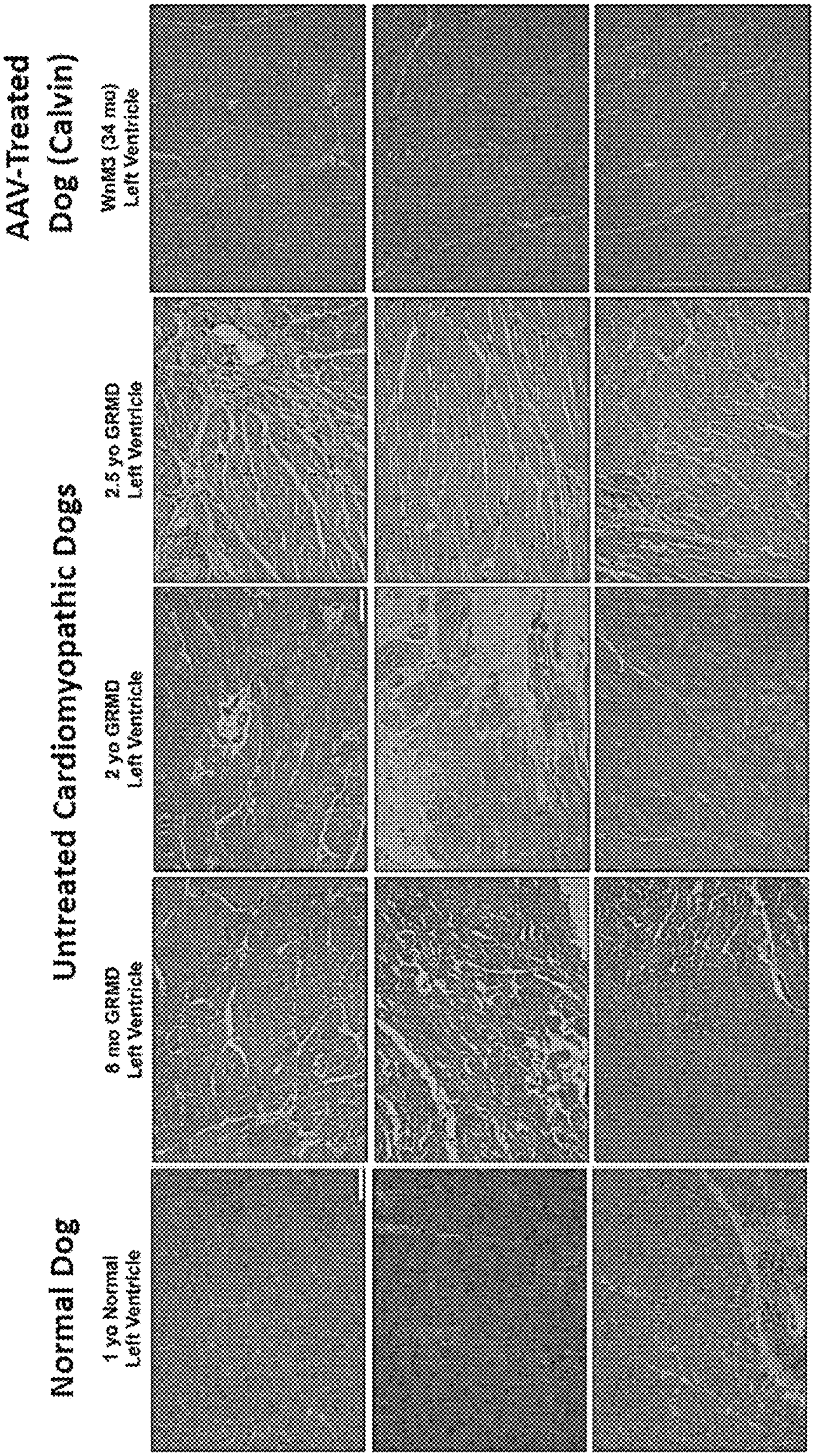
FIG. 19 shows left ventricle histology (H & E stain) of a normal 1 year-old Golden Retriever (far left panel) and a GRMD dog (WnM3/Calvin) that received treatment with the AAVrh.10-S100A1/ARC vector at 7 months of age (far right panel). The treated dog died at 34 months of age due to aspiration pneumonia, even though his cardiac function was still in the normal range (FIG. 18). The middle three panels show left ventricle histology from untreated GRMD dogs at 8, 24, and 30 months of age. There is apparent and progressive fibrosis that replaces the muscle tissue. Note that in the treated dog panels on the far right, the histology is not discernably different from that of a normal dog, and markedly less fibrotic and more intact than an untreated GRMD dog.

Next, a study to extend the results of the mouse treatments to a GRMD dogs was conducted. The study under way in GRMD dogs (four dogs to date) entails treatment with AAVrh.10-S100A1/ARC (dog transgene sequences) when cardiac function, as assessed by ejection fraction, drops below the levels of those of the untreated dog's natural history. Frequent echocardiographs and/or MRIs to assess cardiac structural and functional parameters are used to follow the dogs' cardiac status. The first dog treated (WnM3/Calvin) was followed for more than 2 years, during which its cardiac function improved and was stable. This dog died due to complications associated with aspiration pneumonia at 34 months of age, but his cardiac function was still stable and in the normal range through that age. The other three dogs all improved following the initial treatment and have displayed stable cardiac function for greater than a year. This data is depicted in FIG. 18. The death of Calvin from pneumonia allowed assessment of his cardiac histology, which is shown in FIG. 19. Remarkably, the histology of the left ventricle, which without treatment is highly fibrotic at 8 months of age (one month after WnM3 received treatment), appears nearly indistinguishable from that of a normal dog (FIG. 19). This is evidence for nearly total cardiac rescue in a large animal model of DCM that progresses to heart failure and death between one and two years of age. There has never been an untreated dog that has survived longer than 30 months of age in this colony (FIG. 18), and the typical cause of death is heart failure.

Example 7: Immune Response Studies

Four miniature pigs of 45-70 kgs in weight are treated with the rAAV vectors of this disclosure. Two of the pigs receive the high dose of $2\times10^{14}$ genome copies and the other two receive the lower dose of $2\times10^{13}$ genome copies. In each case, two-thirds of the virus is delivered to the left heart, and one-third of the dose is delivered to the right heart. Pigs are screened for antibodies against AAV-rh10 prior to enrollment in the study. Synchrony provide blood for this purpose.

Blood is collected in a red top tube, allowing blood to clot for approximately 30 minutes, and is spun down at 1000×G for 15 minutes and serum is aliquoted into 200 ul aliquots and frozen prior to the screen. The serum is used for analysis of pre-existing antibodies.

Immune Suppression Regimen

Starting 1 day prior to gene transfer, subjects receive 1 mg/kg of glucocorticoid (or prednisone equivalent) daily for 60 days after the infusion. At 60 days post gene transfer, a tapering dose of glucocorticoid is implemented and liver enzymes is monitored for immune response. In the event of an immune response, glucocorticoid dose and regimen is administered again at the discretion of a physician.

Throughout the glucocorticoid administration, prophylactic antibiotics are administered as a precaution.

Delivery of rAAV Particles to Pig Hearts

- Introducer placed in carotid or femoral artery
- Pigtail angiocatheter advanced into left ventricle for coronary angiogram to roadmap the coronary arteries on digital fluoroscopy
- Coronary catheters (each) flushed with heparinized saline with 1 cc of subject's blood and advanced into aortic root and left and right coronary orifices (Judkins R or L in size dependent on size of animal).
- Adenosine CRI (1 mg/kg/min) started intravenously. Vector delivered into coronary after 15 seconds of adenosine CRI. Vector administered over 5-10 seconds and CRI continued 30 seconds after delivery of vector is complete.
- 2/3 vector administered into left coronary and 1/3 vector administered into right coronary.

Pig subjects are monitored by weekly blood draws (serum chemistries, CBC, AAVrh10 antibodies (done by sponsor), Elis spot response) for 2 months following AAV delivery. Two months following delivery, pigs are sacrificed and hearts and other tissues (see below list) are prepared (samples taken for formalin fixative and fresh frozen) and tissues are made available.

Blood Draws Needed:

- serum chemistries 1 red top tube
- CBC panel 1 EDTA purple top tube
- Anti-AAVrh10 ELISA assay 1 red top tube
- ELISPOT at a minimum 1 10 mL EDTA purple top tube Postmortem Procedures Special Procedures Fresh frozen Tissue Collection and Formalin Fixed Paraffin Embedded Tissues

| Muscle/Organ | Abbreviation | Left/Right |
|---|---|---|
| Tibialis Anterior | R/L TA | Both |
| Extensor Digitorum Longus | R/L EDL | Both |
| Soleus | R/LSOL | Both |
| Bicep | R/L BIC | Both |
| Tricep | R/L TRI | Both |
| Heart | HRT | — |
| Lung | LUNG | — |
| Kidney | KIDNEY | — |
| Liver | LIV | — |
| Spleen | SPLN | — |
| Gonad | GND | — |
| Pancreas | PANC | — |
| Popliteal Lymph Node | POPLN | — |
| Inguinal Lymph Node | ING LN | — |
| Mesenteric Lymph Node | MES LN | — |
| Femoral Artery | R/L FEM ART | Both |
| Sural Artery | R/L SUR ART | Both |
| Bladder | BLADDER | — |
| Diaphragm | DIA | — |
| Stomach | STMCH | — |
| Brain | BRAIN | — |
| Spinal Cord | SPN CORD | — |
| Nerve | NERVE | — |
| Sural Nerve | SUR | L/R |
| Porta-Vein | Port al Vein | — |
| Aorta | Aorta | — |
| Inferior Vena Cava | IVC | — |
| Hepatic Port al Vein | HPV | — |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Multiple embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. An rAAV vector for delivering two or more transgenes into the heart of a subject, wherein said vector comprises a polynucleotide that comprises two or more transgenes, wherein a first transgene encodes an S100 family protein, wherein the S100 family protein is cardiac S100 calcium-binding protein A1 (cS100A1), and a second transgene encodes a cardiac Apoptosis Repressor with Caspase Recruitment Domain (cARC), and wherein the first transgene comprises the nucleotide sequence of SEQ ID NO: 8, and the second transgene comprises the nucleotide sequence of SEQ ID NO: 6.

2. The rAAV vector of claim 1, wherein an Internal Ribosome Entry Site (IRES) is present between the cS100A1 transgene and cARC transgene.

3. The rAAV vector of claim 1, wherein the first transgene or the second transgene is operably linked to a cardiac-restricted promoter selected from cardiac troponin C, cardiac troponin I, and cardiac troponin T (cTnT).

4. The rAAV vector of claim 1, wherein the first transgene or the second transgene is operably linked to a cardiac-restricted promoter derived from a gene selected from the group consisting of: α-myosin heavy chain gene, 6-myosin heavy chain gene, myosin light chain 2v gene, myosin light chain 2a gene, CARP gene, cardiac α-actin gene, cardiac m2 muscarinic acetylcholine gene, ANF, cardiac sarcoplasmic reticulum Ca-ATPase gene, and skeletal α-actin; or is an artificial cardiac promoter derived from MLC-2v gene.

5. The rAAV vector of claim 1, wherein the rAAV vector is self-complementary.

6. An rAAV particle comprising the rAAV vector of claim 1 encapsidated in an AAV capsid.

7. The rAAV particle of claim 6, wherein the AAV capsid comprises a capsid protein derived from an AAV1, AAV2, AAV3, AAV6, AAV8, AAVrh.74, AAVrh.10, AAV2/6 or AAV9 serotype.

8. A composition comprising the rAAV particle of claim 6.

9. The rAAV vector of claim 1, wherein the rAAV vector encodes a protein comprising the amino acid sequence of SEQ ID NO: 13 or 14.

10. An rAAV vector for delivering two or more transgenes into the heart of a subject, wherein said vector comprises a polynucleotide that comprises two or more transgenes, wherein a first transgene encodes an S100 family protein, wherein the S100 family protein is cardiac S100 calcium-binding protein A1 (cS100A1), and a second transgene encodes a cardiac Apoptosis Repressor with Caspase Recruitment Domain (cARC), and wherein the first transgene comprises the nucleotide sequence of SEQ ID NO: 8.

11. An rAAV vector for delivering two or more transgenes into the heart of a subject, wherein said vector comprises a polynucleotide that comprises two or more transgenes, wherein a first transgene encodes an S100 family protein, wherein the S100 family protein is cardiac S100 calcium-binding protein A1 (cS100A1), and a second transgene encodes a cardiac Apoptosis Repressor with Caspase Recruitment Domain (cARC), and wherein the second transgene comprises the nucleotide sequence of SEQ ID NO: 6.

* * * * *